(12) United States Patent
Maeda et al.

(10) Patent No.: US 6,989,401 B2
(45) Date of Patent: Jan. 24, 2006

(54) SULFONIC ACID DERIVATIVES OF HYDROXAMIC ACIDS AND THEIR USE AS MEDICINAL PRODUCTS

(75) Inventors: Kazuhiro Maeda, Tokyo (JP); Shuji Sonda, Tokyo (JP); Tadahiro Takemoto, Tokyo (JP); Tomokazu Goto, Kyoto (JP); Fujio Kobayashi, Tokyo (JP); Masahiko Kajii, Tokyo (JP); Naruyasu Komorita, Tokyo (JP); Fumihiro Hirayama, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 38 days.

(21) Appl. No.: 10/333,266

(22) PCT Filed: Jul. 19, 2001

(86) PCT No.: PCT/JP01/06275

§ 371 (c)(1),
(2), (4) Date: Feb. 14, 2003

(87) PCT Pub. No.: WO02/06214

PCT Pub. Date: Jan. 24, 2002

(65) Prior Publication Data

US 2003/0176486 A1 Sep. 18, 2003

(30) Foreign Application Priority Data

Jul. 19, 2000 (JP) .................................. 2000-219034
Jul. 19, 2000 (JP) .................................. 2000-219245

(51) Int. Cl.
*A61K 31/403* (2006.01)
*C07D 207/408* (2006.01)

(52) U.S. Cl. ...................... 514/418; 514/575; 548/477; 548/473

(58) Field of Classification Search ................ 514/575, 514/418; 560/312; 562/621, 623; 548/477, 548/473
See application file for complete search history.

(56) References Cited

U.S. PATENT DOCUMENTS 6,147,114 A * 11/2000 Fujisawa et al. ............ 514/575

FOREIGN PATENT DOCUMENTS

| EP | 0 497 192 | 8/1992 |
| EP | 0 574 758 | 12/1993 |
| EP | 832875 A1 * | 1/1998 |
| JP | 7-157470 | 6/1995 |
| WO | 90/05719 | 5/1990 |
| WO | 92/13831 | 8/1992 |
| WO | 94/10990 | 5/1994 |
| WO | 94/21625 | 9/1994 |

OTHER PUBLICATIONS

Underwood, et al, Am. J. Physiol. Lung Cell. Mol. Physiol., 279, L895–L902, 2000.*

Guha, et al, Journal of Biological Chemistry, 277(35), 32124–32132 (2002).*

R. Bone, "The Pathogenesis of Sepsis", Annals of Internal Medicine, vol. 115, pp. 457–469, 1991.

Fujii et al. Pharmaceutical agent Journal, 34, 1501 (1998) with abridged English translation thereof.

Gou Wakabashi et al., Igaku no Ayumi Bessatsu, 108 (1998) with whole English translation thereof.

Masahiko Hirota et al., Nihon Gekagakkai Zasshi 100: pp. 667–673, 1999.

Gou Wakabayashi et al., Nihon Gekagakkai Zasshi 100: pp. 674–678, 1999.

Kazuyoshi Hanasawa et al., ICU and CCU, 197, 1999.

* cited by examiner

*Primary Examiner*—Joseph K. McKane
*Assistant Examiner*—Rebecca Anderson
(74) *Attorney, Agent, or Firm*—Wenderoth, Lind & Ponack, L.L.P.

(57) ABSTRACT

The present invention relates to a novel sulfonic acid derivative of hydroxamic acid or a pharmacologically acceptable salt thereof. More particularly, the present invention relates to a sulfonic acid derivative of hydroxamic acid or a pharmacologically acceptable salt thereof, which is useful as an inhibitor of lipopolysaccharides (LPS). In addition, the present invention relates to a novel intermediate compound useful for the synthesis of this sulfonic acid derivative of hydroxamic acid.

8 Claims, No Drawings

SULFONIC ACID DERIVATIVES OF HYDROXAMIC ACIDS AND THEIR USE AS MEDICINAL PRODUCTS

This application is a U.S. national stage of International Application No. PCT/JP01/06275 filed Jul. 19, 2001.

TECHNICAL FIELD

The present invention relates to a novel sulfonic acid derivative of hydroxamic acid or a pharmacologically acceptable salt thereof. More particularly, the present invention relates to a sulfonic acid derivative of hydroxamic acid or a pharmacologically acceptable salt thereof, which is useful as an inhibitor of lipopolysaccharides (LPS). Furthermore, the present invention relates to a novel intermediate compound useful for the synthesis of the above-mentioned sulfonic acid derivative of hydroxamic acid.

BACKGROUND ART

Sepsis is defined as a systemic inflammatory response syndrome associated with infection [Bone RC: Ann. Intern. Med. 115, 457 (1991)], and first begins with an excess invasion of Gram-negative bacteria, that are causative bacteria of sepsis, or an endotoxin, which is a cell wall constituent component thereof, from a primary lesion into the blood, and distribution thereof throughout the body via the circulatory system. The endotoxin is a lipopolysaccharide (LPS) present in bacterial outer membrane, which is released by the death of Gram-negative bacteria. It stimulates inflammatory cells such as macrophage, neutrophil, lymphocyte and the like and vascular endothelial cell in an organism to cause production of inflammatory cytokines (IL-1, IL-6, IL-8 and the like) including TNF α (tumor necrosis factor α). Such remarkable increase in the inflammatory cytokines causes severe multiple organ dysfunction syndrome (MODS) and often results in the death of organisms.

The chemotherapy of sepsis essentially requires the first use of antibiotics for the eradication of infectious bacteria. In General, administration of antibiotics is most commonly used in parallel with chemotherapy or surgical treatment of complications, in view of the high probability of sequential complications [Fujii et al., Pharmaceutical agent Journal, 34, 1501 (1998)]. As is clear from the fact that lethality due to sepsis has not decreased since 1980s, however, these treatment methods are considered to have reached the limit.

In recent years, anti-cytokine therapies targeting inflammatory cytokines such as TNF α and the like have been actively tried as a new sepsis treatment method. However, effectiveness thereof has not been confirmed in clinical tests of TNF α neutralizing antibody, soluble TNF α receptor and IL-1 receptor antagonist and the like [Gou Wakabayashi et al., Igaku no Ayumi Bessatsu, 108 (1998)]. The targeted inflammatory cytokine is considered to be harmful when it exists in excess but necessary for biological protection as long as it is produced in a certain level of amount.

That is, it means that a complete control of biological activity of cytokine may conversely exacerbate the lesion depending on the stages of disease state of septic patients, which is considered to have been reflected in these clinical achievements [Masahiko Hirota et al., Nihon Gekagakkai Zasshi 100: 667–673 (1999), Gou Wakabayashi et al., Nihon Gekagakkai Zasshi 100: 674–678 (1999)].

In addition, while the endotoxin removing column developed as a medical material has been confirmed to be clinically effective [Kazuhiko Hanazawa et al., ICU and CCU, 197 (1999)], it is expensive and use thereof within the range insurance policy can cover is limited. The foregoing facts suggest importance of endotoxin in the disease state of sepsis, and teach that a low-molecular compound that inhibits endotoxin per se located at the upstream of various inflammatory cytokines including TNF α is a promising new agent for the prophylaxis or treatment of sepsis.

Heretofore, hydroxamic acid derivatives have been studied as MMP (matrix metalloproteinase) inhibitors, and many of such inhibitors have been reported to have an inhibitory action on inflammatory cytokines, particularly TNF α. Many of these have been studied as an agent for the prophylaxis or treatment of sepsis (e.g., WO94/10990 etc.), but have not been clinically applied. In addition, an endotoxin (LPS) inhibitory action by hydroxamic acid derivative has not been reported heretofore.

The present invention has been made in view of the above-mentioned background art, and aims at providing a novel sulfonic acid derivative of hydroxamic acid useful as an LPS inhibitor, and a pharmacologically acceptable salt thereof.

Another object of the present invention is to provide a novel intermediate compound useful for the synthesis of said compound.

A yet another object of the present invention is to provide a novel LPS inhibitor useful as a pharmaceutical agent.

DISCLOSURE OF THE INVENTION

The present inventors have found that a sulfonic acid derivative of hydroxamic acid or a pharmacologically acceptable salt thereof has an LPS inhibitory action, and further found that the compound of the present invention inhibits an increase of LPS in animal models, too, which resulted in the completion of the present invention.

Accordingly, the present invention provides the following.

(1) A sulfonic acid derivative of hydroxamic acid of the formula (I)

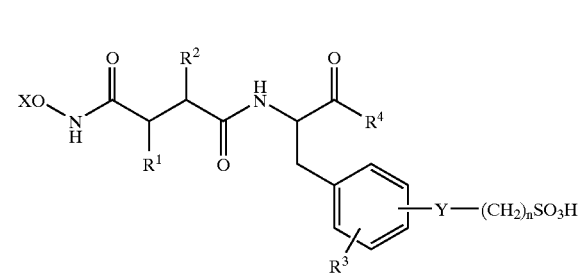

wherein
X is hydrogen or a hydroxyl group-protecting group;
$R^1$ is hydrogen, alkyl, arylalkyl, heteroarylalkyl, heteroarylalkylthioalkyl, heteroarylthioalkyl, arylthioalkyl, alkylthioalkyl, arylalkylthioalkyl, phthalimidoalkyl, alkenyl, or —$(CH_2)_1$-A [1 is an integer of any of 1 to 4 and A is a nitrogen-containing 5- or 6-membered hetero ring which (a) is bonded via a nitrogen atom, (b) may contain, as a further hetero atom, at least one kind of atom selected from nitrogen, oxygen and sulfur at a position not adjacent to the bonded nitrogen atom, (c) contains carbon atoms adjacent to the bonded nitrogen atom, one or both of which is(are) substituted by oxo, and which (d) is benzocondensed or has one or more other carbon atoms optionally substituted by lower alkyl or oxo, and/or has other nitrogen atom optionally substituted by lower alkyl or phenyl];

R² is hydrogen, alkyl, arylalkyl, heteroarylalkyl, cycloalkyl, cycloalkylalkyl or aryl;
Y is O, NR⁷ (R⁷ is as defined for R²) or S;
n is an integer of any of 1 to 6;
R³ is hydrogen, halogen (fluorine, chlorine, bromine, iodine), hydroxyl group, trifluoromethyl, cyano, nitro, amino, alkyl, alkoxy, acyloxy, carbamoyl, lower alkylamino or dilower alkylamino group;
R⁴ is OR⁸ (R⁸ is hydrogen, lower alkyl, aryl, heteroaryl, arylalkyl or heteroarylalkyl) or NR¹⁰R¹¹ [R¹⁰ and R¹¹ are the same or different and each is hydrogen, lower alkyl, arylalkyl, heteroaryl, heteroarylalkyl or aryl, or R¹⁰ and R¹¹ may form an optionally substituted hetero ring together with the adjacent nitrogen atom]; and
the aforementioned arylalkyl, heteroarylalkyl, heteroarylalkylthioalkyl, heteroarylthioalkyl, arylthioalkyl, arylalkylthioalkyl, phthalimidoalkyl, aryl and heteroaryl optionally have substituents,
or a pharmacologically acceptable salt thereof,
(2) the sulfonic acid derivative of hydroxamic acid of the above-mentioned (1), wherein R³ is hydrogen or a pharmacologically acceptable salt thereof,
(3) the sulfonic acid derivative of hydroxamic acid of the above-mentioned (1) or (2), wherein R⁴ is NHCH₃ or NHC₆H₅, or a pharmacologically acceptable salt thereof,
(4) A sulfonic acid derivative of hydroxamic acid of the formula (II)

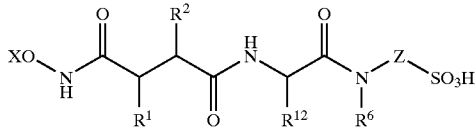

II wherein
X is hydrogen or a hydroxyl group-protecting group;
R¹ is hydrogen, alkyl, arylalkyl, heteroarylalkyl, heteroarylalkylthioalkyl, heteroarylthioalkyl, arylthioalkyl, alkylthioalkyl, arylalkylthioalkyl, phthalimidoalkyl, alkenyl, or —(CH₂)₁-A [1 is an integer of any of 1 to 4 and A is a nitrogen-containing 5- or 6-membered hetero ring which (a) is bonded via a nitrogen atom, (b) may contain, as a further hetero atom, at least one kind of atom selected from nitrogen, oxygen and sulfur at a position not adjacent to the bonded nitrogen atom, (c) contains carbon atoms adjacent to the bonded nitrogen atom, one or both of which is(are) substituted by oxo, and which (d) is benzocondensed or has one or more other carbon atoms optionally substituted by lower alkyl or oxo, and/or has other nitrogen atom optionally substituted by lower alkyl or phenyl];
R² is hydrogen, alkyl, arylalkyl, heteroarylalkyl, cycloalkyl, cycloalkylalkyl or aryl;
R¹² is a characteristic group of natural or non-natural α-amino acid, wherein a functional group present therein may be protected;
R⁶ is hydrogen, lower alkyl, aryl, heteroaryl, arylalkyl or heteroarylalkyl;
Z is alkylene having 1 to 6 carbon atoms, phenylene or naphthalene; and
the aforementioned arylalkyl, heteroarylalkyl, heteroarylalkylthioalkyl, heteroarylthioalkyl, arylthioalkyl, arylalkylthioalkyl, phthalimidoalkyl, aryl and heteroaryl optionally have substituents,
or a pharmacologically acceptable salt thereof,
(5) the sulfonic acid derivative of hydroxamic acid of the above-mentioned (4), wherein R¹² is benzyl, or a pharmacologically acceptable salt thereof, (6) the sulfonic acid derivative of hydroxamic acid of the above-mentioned (4) or (5), wherein R⁶ is hydrogen, or a pharmacologically acceptable salt thereof,
(7) the sulfonic acid derivative of hydroxamic acid of any of the above-mentioned (1) to (6), wherein R¹ is phthalimidomethyl, or a pharmacologically acceptable salt thereof,
(8) the sulfonic acid derivative of hydroxamic acid of any of the above-mentioned (1) to (7), wherein R² is isobutyl, or a pharmacologically acceptable salt thereof,
(9) a sulfonic acid derivative of hydroxamic acid selected from the group consisting of 5-methyl-3(R)-[1(S)-methylcarbamoyl-2-(4-sulfomethoxyphenyl)ethylcarbamoyl]-2(R or S)-phthalimidomethylhexanohydroxamic acid,
5-methyl-3(R)-{1(S)-methylcarbamoyl-2-[4-(2-sulfoethoxy)phenyl]ethylcarbamoyl}-2(R or S)-phthalimidomethylhexanohydroxamic acid,
5-methyl-3(R)-{1(S)-methylcarbamoyl-2-[4-(3-sulfopropoxy)phenyl]ethylcarbamoyl}-2(R or S)-phthalimidomethylhexanohydroxamic acid,
5-methyl-3(R)-{1(S)-methylcarbamoyl-2-[4-(4-sulfobutoxy)phenyl]ethylcarbamoyl}-2(R or S)-phthalimidomethylhexanohydroxamic acid,
5-methyl-3(R)-{1(S)-methylcarbamoyl-2-[4-(5-sulfopentoxy)phenyl]ethylcarbamoyl}-2(R or S)-phthalimidomethylhexano hydroxamic acid,
5-methyl-3(R)-[1(S)-methylcarbamoyl-2-(4-sulfomethoxyphenyl)ethylcarbamoyl]-2(R or S)-(2-naphthylmethyl)hexanohydroxamic acid,
5-methyl-3(R)-{1(S)-methylcarbamoyl-2-[4-(2-sulfoethoxy)phenyl]ethylcarbamoyl}-2(R or S)-(2-naphthylmethyl)hexanohydroxamic acid,
5-methyl-3(R)-{1(S)-methylcarbamoyl-2-[4-(3-sulfopropoxy)phenyl]ethylcarbamoyl}-2(R or S)-(2-naphthylmethyl)hexanohydroxamic acid,
5-methyl-3(R)-{1(S)-methylcarbamoyl-2-[4-(4-sulfobutoxy)phenyl]ethylcarbamoyl}-2(R or S)-(2-naphthylmethyl)hexanohydroxamic acid,
5-methyl-3(R)-{1(S)-methylcarbamoyl-2-[4-(5-sulfopentoxy)phenyl]ethylcarbamoyl}-2(R or S)-(2-naphthylmethyl)hexanohydroxamic acid,
5-methyl-3(R)-{1(S)-phenylcarbamoyl-2-[4-(3-sulfopropoxy)phenyl]ethylcarbamoyl}-2(R or S)-phthalimidomethylhexanohydroxamic acid,
5-methyl-3(R)-[2-phenyl-1(S)-(sulfomethylcarbamoyl)ethylcarbamoyl]-2(R or S)-phthalimidomethylhexanohydroxamic acid,
5-methyl-3(R)-[2-phenyl-1(S)-(2-sulfoethylcarbamoyl)ethylcarbamoyl]-2(R or S)-phthalimidomethylhexanohydroxamic acid,
5-methyl-3(R)-[2-phenyl-1(S)-(3-sulfopropylcarbamoyl)ethylcarbamoyl]-2(R or S)-phthalimidomethylhexanohydroxamic acid,
5-methyl-3(R)-[2-phenyl-1(S)-(4-sulfobutylcarbamoyl)ethylcarbamoyl]-2(R or S)-phthalimidomethylhexanohydroxamic acid,
5-methyl-3(R)-[2-phenyl-1(S)-(5-sulfopentylcarbamoyl)ethylcarbamoyl]-2(R or S)-phthalimidomethylhexanohydroxamic acid,
5-methyl-2(R or S)-(2-naphthylmethyl)-3(R)-[2-phenyl-1(S)-(sulfomethylcarbamoyl)ethylcarbamoyl]hexanohydroxamic acid,
5-methyl-2(R or S)-(2-naphthylmethyl)-3(R)-[2-phenyl-1(S)-(2-sulfoethylcarbamoyl)ethylcarbamoyl]hexanohydroxamic acid,
5-methyl-2(R or S)-(2-naphthylmethyl)-3(R)-[2-phenyl-1(S)-(3-sulfopropylcarbamoyl)ethylcarbamoyl]hexanohydroxamic acid, 5-methyl-2(R or S)-(2-naphthylmethyl)-3(R)-[2-phenyl-1(S)-(4-sulfobutylcarbamoyl)ethylcarbamoyl]hexanohydroxamic acid, 5-methyl-2(R or S)-(2-naphthylmethyl)-3(R)-[2-phenyl-1(S)-(5-sulfopentylcarbamoyl)ethylcarbamoyl]hexanohydroxamic acid and 5-methyl-3(R)-[2-phenyl-1(S)-(4-sulfophenylcarbamoyl)ethylcarbamoyl]-2(R or S)-phthalimidomethylhexanohydroxamic acid, or a pharmacologically acceptable salt thereof,

(10) a compound of the formula (III)

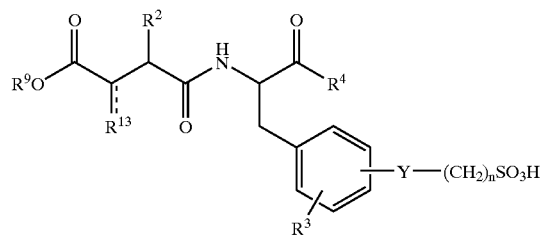

III wherein $R^9$ is hydrogen, alkyl, arylalkyl, heteroarylalkyl or aryl;

=== is a single bond or double bond;

$R^{13}$ is, when === is a single bond, hydrogen, alkyl, arylalkyl, heteroarylalkyl, heteroarylalkylthioalkyl, heteroarylthioalkyl, arylthioalkyl, alkylthioalkyl, arylalkylthioalkyl, phthalimidoalkyl, alkenyl, —$(CH_2)_l$-A [l is an integer of any of 1 to 4 and A is a nitrogen-containing 5- or 6-membered hetero ring, which (a) is bonded via a nitrogen atom, (b) may contain, as a further hetero atom, at least one kind of atom selected from nitrogen, oxygen and sulfur at a position not adjacent to the bonded nitrogen atom, (c) contains carbon atoms adjacent to the bonded nitrogen atom, one or both of which is(are) substituted by oxo, and which (d) is benzocondensed or has one or more other carbon atoms optionally substituted by lower alkyl or oxo, and/or has other nitrogen atom optionally substituted by lower alkyl or phenyl] or —$COOR^{14}$ ($R^{14}$ is hydrogen, alkyl, arylalkyl, heteroarylalkyl or aryl), or $CH_2$ when === is a double bond;

$R^2$ is hydrogen, alkyl, arylalkyl, heteroarylalkyl, cycloalkyl, cycloalkylalkyl or aryl;

Y is O, $NR^7$ ($R^7$ is as defined for $R^2$) or S;

n is an integer of any of 1 to 6;

$R^3$ is hydrogen, halogen (fluorine, chlorine, bromine, iodine), hydroxyl group, trifluoromethyl, cyano, nitro, amino, alkyl, alkoxy, acyloxy, carbamoyl, lower alkylamino or dilower alkylamino group; and $R^4$ is $OR^8$ ($R^8$ is hydrogen, lower alkyl, aryl, heteroaryl, arylalkyl or heteroarylalkyl) or $NR^{10}R^{11}$ [$R^{10}$ and $R^{11}$ are the same or different and each is hydrogen, lower alkyl, arylalkyl, heteroaryl, heteroarylalkyl or aryl, or $R^{10}$ and $R^{11}$ may form an optionally substituted hetero ring together with the adjacent nitrogen atom];

or a pharmacologically acceptable salt thereof,

(11) a compound of the formula (IV)

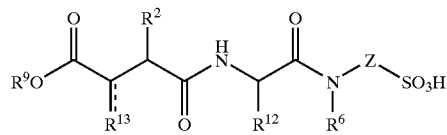

IV wherein $R^9$ is hydrogen, alkyl, arylalkyl, heteroarylalkyl or aryl;

=== is a single bond or double bond;

$R^{13}$ is, when === is a single bond, hydrogen, alkyl, arylalkyl, heteroarylalkyl, heteroarylalkylthioalkyl, heteroarylthioalkyl, arylthioalkyl, alkylthioalkyl, arylalkylthioalkyl, phthalimidoalkyl, alkenyl, —$(CH_2)_l$-A [l is an integer of any of 1 to 4 and A is a nitrogen-containing 5- or 6-membered hetero ring, which (a) is bonded via a nitrogen atom, (b) may contain, as a further hetero atom, at least one kind of atom selected from nitrogen, oxygen and sulfur at a position not adjacent to the bonded nitrogen atom, (c) contains carbon atoms adjacent to the bonded nitrogen atom, one or both of which is(are) substituted by oxo, and which (d) is benzocondensed or has one or more other carbon atoms optionally substituted by lower alkyl or oxo, and/or has other nitrogen atom optionally substituted by lower alkyl or phenyl] or —$COOR^{14}$ ($R^{14}$ is hydrogen, alkyl, arylalkyl, heteroarylalkyl or aryl), or $CH_2$ when === is a double bond;

$R^2$ is hydrogen, alkyl, arylalkyl, heteroarylalkyl, cycloalkyl, cycloalkylalkyl or aryl;

$R^{12}$ is a characteristic group of natural or non-natural α-amino acid, wherein a functional group present therein may be protected;

$R^6$ is hydrogen, lower alkyl, aryl, heteroaryl, arylalkyl or heteroarylalkyl;

Z is alkylene having 1 to 6 carbon atoms, phenylene or naphthalene;

or a pharmacologically acceptable salt thereof,

(12) a pharmaceutical composition containing the sulfonic acid derivative of hydroxamic acid of any of the above-mentioned (1)–(9) or a pharmacologically acceptable salt thereof and a pharmacologically acceptable carrier, and

(13) an LPS inhibitor containing the sulfonic acid derivative of hydroxamic acid of any of the above-mentioned (1)–(9) or a pharmacologically acceptable salt thereof as an active ingredient.

BEST MODE FOR EMBODYING THE INVENTION

The symbols used in the present specification are explained in the following.

The "alkyl" for $R^1$, $R^2$, $R^3$, $R^7$, $R^9$, $R^{13}$ and $R^{14}$ is linear or branched alkyl having 1 to 10 carbon atoms, such as methyl, ethyl, n-propyl, isopropyl, n-butyl, isobutyl, sec-butyl, tert-butyl, n-pentyl, isopentyl, n-hexyl, n-octyl, n-decyl and the like.

The "lower alkyl" for $R^3$, $R^6$, $R^8$, $R^{10}$ and $R^{11}$ is linear or branched alkyl having 1 to 6 carbon atoms, such as methyl, ethyl, n-propyl, isopropyl, n-butyl, isobutyl, sec-butyl, tert-butyl, n-pentyl, isopentyl, n-hexyl and the like.

The "aryl" for $R^2$, $R^6$, $R^7$, $R^8$, $R^9$, $R^{10}$, $R^{11}$ and $R^{14}$ is aryl having 6 to 10 carbon atoms, such as phenyl, naphthyl, aryl which is an ortho-fused bicyclic group having 8 to 10 ring atoms wherein at least one ring is an aromatic ring (e.g., indenyl and the like), and the like, with preference given to phenyl.

The "heteroaryl" for $R^6$, $R^8$, $R^{10}$ and $R^{11}$ is a 5- or 6-membered ring group having a carbon atom and 1 to 4 hetero atoms (oxygen, sulfur or nitrogen), ortho-fused bicyclic heteroaryl having 8 to 10 ring atoms, which is derived therefrom, particularly a benzo derivative condensed with benzene ring, one derived by fusing propenylene, trimethylene or tetramethylene group therewith, stable N-oxide thereof and the like. Examples thereof include pyrrolyl, pyrrolynyl, furyl, thienyl, oxazolyl, isoxazolyl, imidazolyl, thiazolyl, isothiazolyl, pyrazolyl, 1,2,3-triazolyl, 1,2,4-triazolyl, tetrazolyl, 1,3,4-oxadiazolyl, 1,2,4-oxadiazolyl, 1,3,4-thiadiazolyl, 1,2,4-thiadiazolyl, pyridyl, pyranyl, pyrazinyl, pyrimidinyl, pyridazinyl, 1,2,4-triazinyl, 1,2,3-triazinyl, 1,3,5-triazinyl, 1,2,5-oxathiazinyl, 1,2,6-oxathiazinyl, benzoxazolyl, benzothiazolyl, benzoimidazolyl, thianaphtenyl, isothianaphtenyl, benzofuranyl, benzothienyl, isobenzofuranyl, chlomenyl, isoindolyl, indolyl, indazolynyl, isoquinolyl, quinolyl, phthalazinyl, quinoxalynyl, quinazolynyl, synnolynyl, benzoxazinyl and the like, with preference given to pyridyl.

The "cycloalkyl" for $R^2$ is cycloalkyl having 3 to 7 carbon atoms, such as cyclopropyl, cyclobutyl, cyclopentyl, cyclohexyl, cycloheptyl and the like.

The cycloalkyl moiety of "cycloalkylalkyl" for $R^2$ is as defined for the above-mentioned "cycloalkyl", and the alkyl moiety is as defined for the above-mentioned "lower alkyl". Examples of such cycloalkylalkyl include cyclopropylmethyl, 2-cyclobutylethyl, cyclopentylmethyl, 3-cyclopentylpropyl, cyclohexylmethyl, 2-cyclohexylethyl, cycloheptylmethyl and the like.

The "alkenyl" for $R^1$ and $R^{13}$ is alkenyl having 2 to 6 carbon atoms, such as vinyl, allyl, 3-butenyl, 5-hexenyl and the like.

The aryl moiety of "arylalkyl" for $R^1$, $R^2$, $R^6$, $R^7$, $R^8$, $R^9$, $R^{10}$, $R^{11}$, $R^{13}$ and $R^{14}$ is as defined for the above-mentioned "aryl", and the alkyl moiety is as defined for the above-mentioned "lower alkyl". Examples of such arylalkyl include benzyl, phenethyl, 3-phenylpropyl, 1-naphthylmethyl, 2-naphthylmethyl, 2-(1-naphthyl)ethyl, 2-(2-naphthyl)ethyl, 3-(1-naphthyl)propyl, 3-(2-naphthyl)propyl and the like.

The heteroaryl moiety of "heteroarylalkyl" for $R^1$, $R^2$, $R^6$, $R^7$, $R^8$, $R^9$, $R^{10}$, $R^{11}$, $R^{13}$ and $R^{14}$ is as defined for the above-mentioned "heteroaryl", and the alkyl moiety is as defined for the above-mentioned "lower alkyl". Examples of such heteroarylalkyl include 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl)ethyl, 3-(2-pyrrolyl)propyl and the like.

The alkyl moiety of the alkylthio moiety of "alkylthioalkyl" for $R^1$ and $R^{13}$ is as defined for the above-mentioned "alkyl", and the remaining alkyl moiety is as defined for the above-mentioned "lower alkyl". Examples of such alkylthioalkyl include methylthiomethyl, ethylthiomethyl, n-propylthiomethyl, isopropylthiomethyl, n-butylthiomethyl, isobutylthiomethyl, sec-butylthiomethyl, tert-butylthiomethyl and the like.

The aryl moiety of "arylthioalkyl" for $R^1$ and $R^{13}$ is as defined for the above-mentioned "aryl", and the alkyl moiety is as defined for the above-mentioned "lower alkyl". Examples of such arylthioalkyl include phenylthiomethyl, 1-naphthylthiomethyl, 2-naphthylthiomethyl and the like.

The heteroaryl moiety of "heteroarylthioalkyl" for $R^1$ and $R^{13}$ is as defined for the above-mentioned "heteroaryl", and the alkyl moiety is as defined for the above-mentioned "lower alkyl". Examples of such heteroarylthioalkyl include 2-pyrrolylthiomethyl, 2-pyridylthiomethyl, 3-pyridylthiomethyl, 4-pyridylthiomethyl, 2-thienylthiomethyl and the like.

The arylalkyl moiety of "arylalkylthioalkyl" for $R^1$ and $R^{13}$ is as defined for the above-mentioned "arylalkyl", and the remaining alkyl moiety is as defined for the above-mentioned "lower alkyl". Examples of such arylalkylthioalkyl include benzylthiomethyl, phenethylthiomethyl and the like.

The heteroarylalkyl moiety of "heteroarylalkylthioalkyl" for $R^1$ and $R^{13}$ is as defined for the above-mentioned "heteroarylalkyl", and the remaining alkyl moiety is as defined for the above-mentioned "lower alkyl". Examples of such heteroarylalkylthioalkyl include 2-pyrrolylmethylthiomethyl, 2-pyridylmethylthiomethyl, 3-pyridylmethylthiomethyl, 4-pyridylmethylthiomethyl, 2-thienylmethylthiomethyl and the like.

The alkyl moiety of "phthalimidoalkyl" for $R^1$ and $R^{13}$ is as defined for the above-mentioned "lower alkyl". Examples of such phthalimidoalkyl include phthalimidomethyl, 2-phthalimidoethyl and the like.

The A of $-(CH_2)_l-A$ for $R^1$ and $R^{13}$ is a nitrogen-containing hetero ring bonded via a nitrogen atom and is exemplified by the following groups.

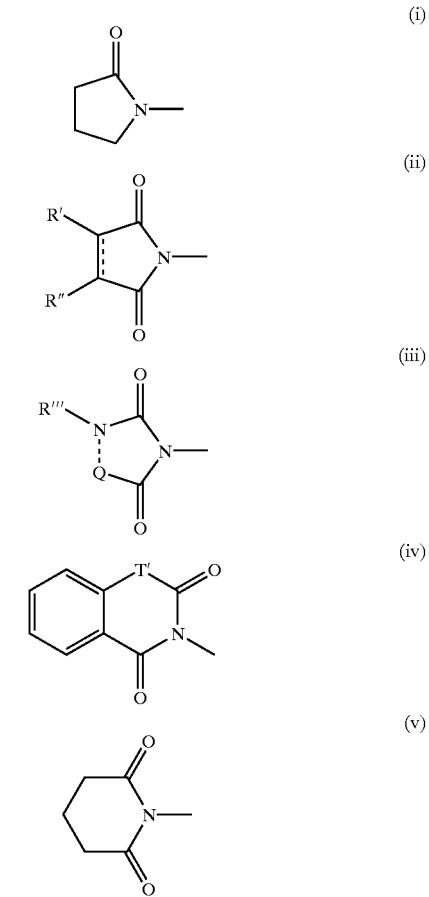

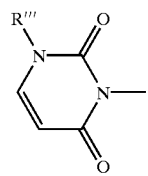
(vi)

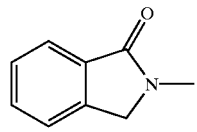
(vii)

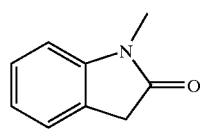
(viii)

wherein

=== is a single bond when R' and R" are each hydrogen and a double bond when R' and R" in combination form a ring, R'" is hydrogen, lower alkyl or phenyl, Q' is —CO—, —CH$_2$—, —CH(lower alkyl)-, —C(lower alkyl)$_2$—, —NH—, —N(lower alkyl)- or —O—, and T' is —O—, —NH— or —N(lower alkyl)-.

The preferable nitrogen-containing hetero ring is exemplified by 2-oxo-1-pyrrolizinyl, 2,5-dioxo-1-pyrrolizinyl, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazolidin-4-yl, 3-methyl-2,4,5-trioxo-1-imidazolidinyl, 2,5-dioxo-3-phenyl-1-imidazolidinyl and 2,6-dioxopiperidino and the like, the rings of the formulas (ii) and (iii), particularly preferably 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl.

The aforementioned arylalkyl, heteroarylalkyl, heteroarylthioalkyl, arylthioalkyl, arylalkylthioalkyl, heteroarylalkylthioalkyl, phthalimidoalkyl, aryl and heteroaryl are optionally substituted by one or more substituents selected from halogen (fluorine, chlorine, bromine, iodine), hydroxyl group, nitro, cyano, trifluoromethyl, lower alkyl (provided that it does not substitute the alkyl moiety of arylalkyl, heteroarylalkyl, heteroarylthioalkyl, arylthioalkyl, arylalkylthioalkyl and phthalimidoalkyl), alkoxy, alkylthio, formyl, acyloxy, oxo, phenyl, arylalkyl, carboxyl, a group represented by —COOR$_a$ [R$_a$ is lower alkyl, arylalkyl or aryl], carbamoyl, amino, lower alkylamino, dilower alkylamino, guanidino, hydroxysulfonyloxy, arylalkyloxyalkyl and the like. As used herein, "lower alkyl", "arylalkyl" and "aryl" are as mentioned above.

The "alkoxy" is linear or branched alkoxy having 1 to 6 carbon atoms, such as methoxy, ethoxy, n-propoxy, isopropoxy, n-butoxy, tert-butoxy and the like.

The alkyl moiety of "alkylthio" is as defined for the above-mentioned "lower alkyl". Examples of such alkylthio include methylthio, ethylthio, n-propylthio, isopropylthio and the like.

The "acyloxy" is linear or branched alkanoyloxy having 2 to 6 carbon atoms, such as acetyloxy, propionyloxy, butyryloxy, valeryloxy, pivaloyloxy, hexanoyloxy and the like.

The arylalkyl moiety of "arylalkyloxyalkyl" is as defined for the above-mentioned "arylalkyl", and the remaining alkyl moiety is as defined for the above-mentioned "lower alkyl". Examples of such arylalkyloxyalkyl include benzyloxymethyl, phenethyloxymethyl and the like.

The "optionally substituted hetero ring" formed by R$^{10}$ and R$^{11}$ together with the adjacent nitrogen atom is a 4- to 7-membered ring group having carbon atom(s) and at least one nitrogen atom, and optionally having, as a further hetero atom in the ring, at least one kind of atom selected from nitrogen, oxygen and sulfur, wherein the carbon atom(s) constituting the ring may be substituted by oxo, and furthermore, an aromatic ring such as benzene ring and the like may be condensed utilizing adjacent two carbon atoms constituting the hetero ring. Examples of such hetero ring include azetidino, 1-pyrrolizinyl, piperidino, 1-piperazinyl, morpholino, thiomorpholino, oxothiomorpholino, dioxothiomorpholino, 2-oxo-1-quinazolynyl and the like.

When the hetero ring contains a nitrogen atom as a further hetero atom in the ring, as in 1-piperazinyl, lower alkyl (as mentioned above), arylalkyl (as mentioned above), heteroarylalkyl (as mentioned above), aryl (as mentioned above), heteroaryl (as mentioned above), a group represented by —COOR$_a$ (R$_a$ is as mentioned above) or acyl may be substituted on the nitrogen atom. Here, acyl is a group represented by —COR$_a$, wherein R$_a$ is as mentioned above.

The characteristic group of the natural or non-natural α-amino acid for R$^{12}$ is a group R in the natural or non-natural α-amino acid represented by H$_2$N—CH(R)—COOH. Examples of the characteristic group derived from the natural α-amino acid are as follows, wherein the corresponding amino acids are shown in the parentheses: hydrogen (glycine), methyl (alanine), isopropyl (valine), isobutyl (leucine), benzyl (phenylalanine), p-hydroxybenzyl (tyrosine), hydroxymethyl (serine), mercaptomethyl (cysteine), 1-hydroxyethyl (threonine), 2-methylthioethyl (methionine), carboxymethyl (aspartic acid), 2-carboxyethyl (glutamic acid), 2-indolylmethyl (tryptophan), 4-imidazolylmethyl (histidine), 4-aminobutyl (lysin) and 3-guanidinopropyl (arginine). Examples of the characteristic group derived from the non-natural α-amino acid are as follows, wherein the corresponding non-natural amino acids are shown in the parentheses: ethyl (α-amino-n-butyric acid), n-propyl (α-amino-n-pentanoic acid), n-butyl (α-amino-n-heptanoic acid), n-heptyl (α-amino-n-nonanoic acid), cyclohexylmethyl (cyclohexylalanine), phenyl (α-amino-phenylacetic acid), 2-phenylethyl (homophenylalanine), 1-naphthyl (α-amino-1-naphthylacetic acid), 2-naphthyl (α-amino-2-naphthylacetic acid), phenethyl (α-amino-3-phenylbutanoic acid), α-methylbenzyl (β-methylphenylalanine), α,α-dimethylbenzyl (β,β-dimethylphenylalanine) and the like.

The optional (reactive) functional group present in R$^{12}$ can be protected by a method known in peptide chemistry. For example, amino group can be protected in the form of tert-butoxycarbonyl, benzyloxycarbonyl or isobornyloxycarbonyl group, or phthalimido group. The carboxyl group can be protected in the form of methyl, ethyl, tert-butyl, benzyl and the like. The hydroxy group can be protected in the form of tert-butyl, benzyl or tetrahydropyranylether, or in the form of acetate. The mercapto group can be protected in the form of tert-butyl, benzyl, or by a similar group.

The "hydroxyl-protecting group" for X is, for example, arylalkyl, aryl, heteroaryl, silyl (e.g., trimethylsilyl, tert-butyldimethylsilyl, tert-butyldiphenylsilyl and the like), 2-tetrahydropyranyl and the like. The arylalkyl, aryl and heteroaryl optionally have one or more substituents selected from, for example, halogen (fluorine, chlorine, bromine, iodine), hydroxyl group, nitro, cyano, trifluoromethyl, lower alkyl (provided that it does not substitute the alkyl moiety of arylalkyl), alkoxy, alkylthio, formyl, acyloxy, oxo, phenyl, arylalkyl, carboxyl, a group represented by —COOR$_a$ [R$_a$ is lower alkyl, arylalkyl or aryl], carbamoyl, amino, lower alkylamino, dilower alkylamino, guanidino, hydroxysulfonyloxy, arylalkyloxyalkyl and the like. The protecting group of hydroxyl group of the compound of the present invention is preferably silyl, 2-tetrahydropyranyl, benzyl and the like.

The "alkylene" for Z is a methylene chain having 1 to 5 carbon atoms, such as methylene, ethylene, propylene, butylene or pentylene and the like.

The "phenylene" for Z is a divalent aromatic hydrocarbon group represented by —C$_6$H$_4$—, such as 1,2-, 1,3- or 1,4-phenylene.

The "naphthalene" for Z is a divalent aromatic hydrocarbon group represented by —C$_{10}$H$_6$—, such as 1,2-, 1,4-, 1,5-, 2,5- or 2,8-naphthalene and the like.

The phenylene and naphthalene for the aforementioned Z are optionally substituted by one or more substituents selected from halogen (fluorine, chlorine, bromine, iodine), hydroxyl group, nitro, cyano, trifluoromethyl, lower alkyl, alkoxy, acyloxy, hydroxysulfonyl, hydroxysulfonyloxy and the like. As used herein, "lower alkyl", "alkoxy" and "acyloxy" are as mentioned above.

When the sulfonic acid derivatives of hydroxamic acid represented by the formulas (I) and (II), compounds represented by the formulas (III) and (IV) and pharmacologically acceptable salts thereof have an asymmetric carbon, they can be present as an optically active form or a racemate. The racemate can be separated into each optically active form by a means known per se. When the sulfonic acid derivative of hydroxamic acid and a pharmacologically acceptable salt thereof have an additional asymmetric carbon, the compound can be present as a diastereomer mixture, or as a single diastereomer, which can be also separated by a means known per se.

The sulfonic acid derivative of hydroxamic acid and a pharmacologically acceptable salt thereof can show polymorphism, and can be present as more than one tautomers, and further, can be present as a solvate.

Accordingly, the present invention encompasses the aforementioned any stereoisomer, optical isomer, polymorph, tautomer, solvate, optional mixtures thereof and the like. Optically active form, racemate and diastereomer are also encompassed in the scope of the present invention.

The pharmacologically acceptable salts of the sulfonic acid derivatives of hydroxamic acid represented by the formulas (I) and (II) and the compounds of the formulas (III) and (IV) may be, for example, alkali metal salt (salt with lithium, sodium, potassium and the like), alkaline earth metal salt (salt with calcium, magnesium and the like), aluminum salt, ammonium salt, salt with organic base (triethylamine, morpholine, piperidine, triethanolamine, trishydroxymethylaminomethane, meglumine and the like), salt with natural α-amino acid (alanine, phenylalanine, histidine, lysin, arginine and the like), and the like.

Other pharmacologically acceptable salts may be, for example, inorganic acid addition salt (salt with hydrochloric acid, hydrobromic acid, hydroiodic acid, sulfuric acid, phosphoric acid and the like), organic acid addition salt (salt with methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid and the like), salt with amino acid (glutamic acid, aspartic acid and the like) and the like. Moreover, a salt may be formed with oxalic acid for crystallization.

Preferable embodiment of the sulfonic acid derivatives of hydroxamic acid represented by the formulas (I) and (II), and compounds represented by the formulas (III) and (IV) is exemplified by a free acid or pharmacologically acceptable salt. Crystallization is possible in both forms, and an optional derivative and an isomer thereof can be prepared at high purity in a large amount.

Preferable embodiments of the sulfonic acid derivatives of hydroxamic acid represented by the formulas (I) and (II), and pharmacologically acceptable salts thereof are exemplified by a sulfonic acid derivative of hydroxamic acid of the formula (I) or (II), wherein R$^1$ is phthalimidomethyl, or a pharmacologically acceptable salt thereof, a sulfonic acid derivative of hydroxamic acid of the formula (I) or (II), wherein R$^2$ is isobutyl, or a pharmacologically acceptable salt thereof, a hydroxamic acid derivative, wherein, in the formula (I), R$^3$ is hydrogen, or a pharmacologically acceptable salt thereof, a hydroxamic acid derivative of the formula (I), wherein R$^4$ is NHCH$_3$ or NHC$_6$H$_5$, or a pharmacologically acceptable salt thereof, a sulfonic acid derivative of hydroxamic acid of the formula (II), wherein R$^{12}$ is benzyl, or a pharmacologically acceptable salt thereof, a sulfonic acid derivative of hydroxamic acid of the formula (II), wherein R$^6$ is hydrogen, or a pharmacologically acceptable salt thereof, and the like.

Specifically, the compounds of Examples 1, 2, 10, 11, 13, 14, 15, 17, 19, 21 and 22 in the Examples below are preferable compounds, including these preferable embodiments.

The preparation methods of the sulfonic acid derivative of hydroxamic acid or a pharmacologically acceptable salt thereof of the present invention are shown in the following.

Preparation Methods of Sulfonic Acid Derivative of Hydroxamic Acid which is Represented by of the Formula (I):

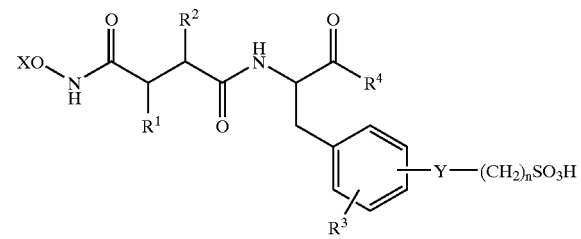

I

Scheme 1

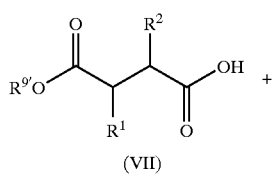

(VII)

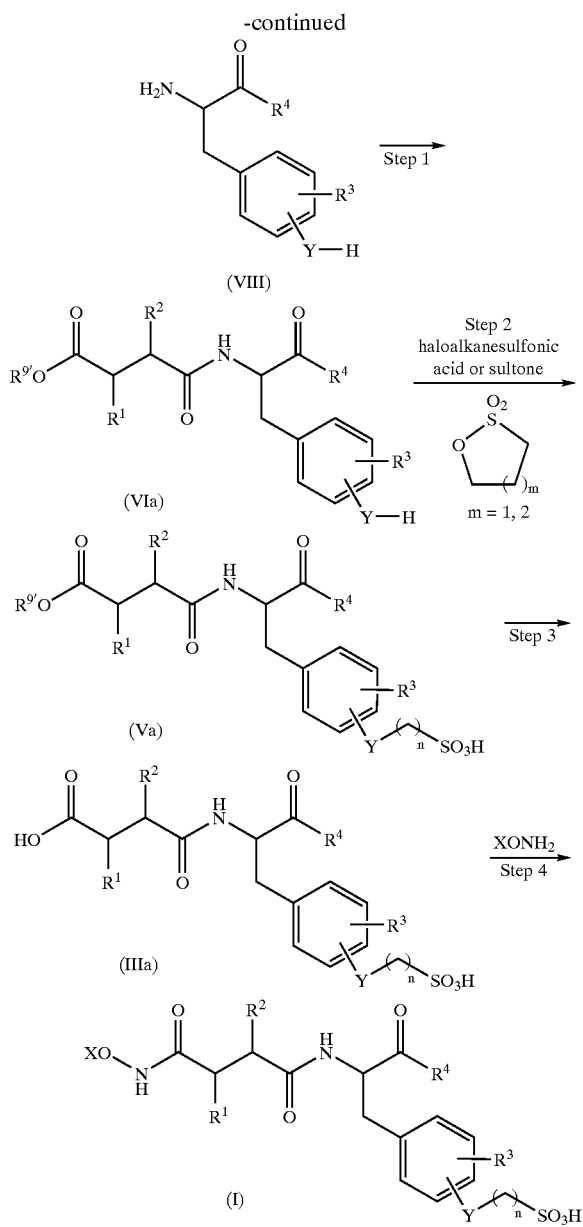

wherein n is an integer of 1 to 6, $R^{9'}$ is as defined for $R^9$ (except hydrogen) and $R^1$, $R^2$, $R^3$, $R^4$, X and Y are as defined above.

As shown in the above-mentioned Scheme 1, the sulfonic acid derivative of hydroxamic acid (I) or a pharmacologically acceptable salt thereof of the present invention can be prepared by converting carboxylic acid (VII) as a starting material using an amino derivative (VIII) according to the C terminus activation method for peptide synthesis [e.g., *Pepuchidogousei no kiso to jikken,* Izumiya et al., Maruzen Shoten, p 91] to an intermediate compound (VIa), and via conversion of this compound to sulfonic acid derivative (Va) and sulfonic acid derivative (IIIa). The carboxylic acid (VII) to be the starting material is a compound described in a reference (Japanese Patent Application under PCT laid-open under kohyo No. H6-506445, JP-A-4-352757, JP-A-7-157470, Japanese Patent Application under PCT laid-open under kohyo No. H4-502008, JP-A-6-65196, specification of WO96/33968, specification of WO94/21625 and the like), or prepared according to a conventional method based on these references.

The amino derivative (VIII) can be prepared by, for example, the method to be explained below.

The detail of each step is explained in the following.

Step 1

In Step 1, carboxylic acid (VII) and amino derivative (VIII) are reacted to give intermediate compound (VIa).

The representative method is shown in the following.

Step 1—1) Method Using Mixed Acid Anhydride

The intermediate compound (VIa) can be obtained by reacting carboxylic acid (VII) with isobutyl chlorocarbonate in the presence of an amine base such as triethylamine, N-methylmorpholine and the like, and reacting the resultant compound with amino derivative (VIII). The solvent used may be an aprotic solvent such as tetrahydrofuran (THF), methylene chloride, ethyl acetate, N,N-dimethylformamide (DMF) and the like, and the reactions can be carried out at −15° C. to room temperature.

Step 1-2) Method Using Acid Chloride

Carboxylic acid (VII) is reacted with oxalyl chloride or thionyl chloride to once give an acid chloride. The solvent used is methylene chloride or a hydrocarbon solvent such as benzene, toluene and the like, and the reaction is carried out at −15° C. to room temperature or under heating. The intermediate compound (VIa) can be obtained by reacting the obtained acid chloride with amino derivative (VIII) in the presence of an amine base such as triethylamine, pyridine and the like. The solvent used is an aprotic solvent such as THF, ethyl acetate, DMF, methylene chloride, benzene, toluene and the like, and the reaction can be carried out at −15° C. to room temperature or under heating.

Step 1-3) Method Using DCC-HOBt Method (Coupling Method)

The intermediate compound (VIa) can be obtained by reacting carboxylic acid (VII) and amino derivative (VIII) with 1,3-dicyclohexylcarbodiimide (DCC) and 1-hydroxybenzotriazole (HOBt) or 3-hydroxy-3,4-dihydro-4-oxo-1,2,3-benzotriazine (HOOBt) as a condensation agent, in the presence of an amine base such as triethylamine or N-methylmorpholine and the like, at a temperature of not higher than room temperature. As the condensation agent, 1,3-diisopropylcarbodiimide (DIPCI), 1-ethyl-3-(3-dimethylaminopropyl)carbodiimide hydrochloride (WSCI.HCl) or benzotriazol-1-yl-oxy-tris-(dimethylamino)-phosphonium hexafluorophosphate (BOP reagent) and the like can be used instead of DCC. The solvent used is an aprotic solvent such as THF, methylene chloride, ethyl acetate, DMF, pyridine and the like.

Step 1-4) Method Using Active Ester Method

Carboxylic acid (VII) and a phenol derivative such as pentafluorophenol and the like or N-hydroxysuccinimide are reacted with a condensation agent such as DCC and the like to once give an active ester. An amine base is used as necessary, and the amine base to be used is triethylamine or N-methylmorpholine and the like. The solvent used is an aprotic solvent such as THF, DMF, methylene chloride and the like, and the reaction is carried out at a temperature not higher than room temperature. The intermediate compound (VIa) can be obtained by reacting the obtained active ester with amino derivative (VIII). An amine base is used as necessary, and the amine base to be used is triethylamine or N-methylmorpholine and the like. The solvent used is an aprotic solvent such as THF, DMF, methylene chloride and the like, and the reaction can be carried out at a temperature not higher than room temperature.

Step 2

The sulfonic acid derivative (Va) can be obtained by reacting intermediate compound (VIa) with haloalkanesulfonic acid or sultone in the presence of an inorganic base such as potassium carbonate or cesium carbonate and the like. The solvent used is an aprotic solvent such as DMF, acetonitrile, acetone and the like, and the reaction can be carried out at −15° C. to room temperature or under heating.

Step 3

In Step 3, sulfonic acid derivative (Va) is converted to sulfonic acid derivative (IIIa). For example, when $R^{9'}$ can be removed with an acid, such as a tert-butyl group, sulfonic acid derivative (Va) can be converted to sulfonic acid derivative (IIIa) by reacting with hydrogen chloride or trifluoroacetic acid. The solvent used is an ether solvent such as 1,4-dioxane and the like, or methylene chloride and the like, and the reaction can be carried out at a temperature of not higher than room temperature.

Step 4

In Step 4, sulfonic acid derivative (IIIa) is reacted with unprotected hydroxylamine ($XONH_2$; X is as defined above or hydroxylamine protected by silyl (trimethylsilyl, tert-butyldimethylsilyl, tert-butyldiphenylsilyl and the like), tert-butyl, benzyl, benzyloxymethyl, p-methoxybenzyl, 2-nitrobenzyl, 2-tetrahydropyranyl (Chem. Pharm. Bull. Jpn. 23, 167, 1975) group and the like) for conversion thereof to sulfonic acid derivative of hydroxamic acid (I). As the reaction conditions, those of Step 1 can be applied. When protected hydroxylamine is used, the protecting group can be removed after reaction under general deprotection conditions of hydroxyl group [T. W. Greene et. al., PROTECTIVE GROUPS IN ORGANIC SYNTHESIS, $2^{nd}$ ed., (JOHN WILEY & SONS, Inc.)].

The sulfonic acid derivative (Va) can be also prepared by a method shown in the following Scheme 2.

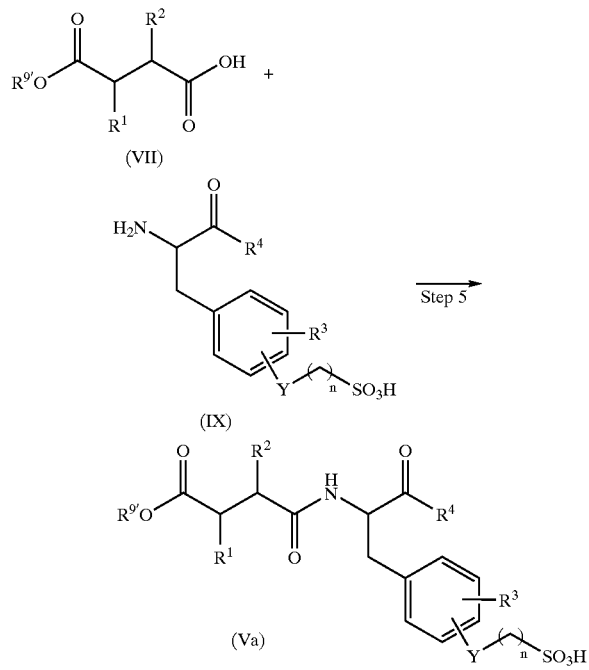

wherein n is an integer of 1 to 6, and $R^1$, $R^2$, $R^3$, $R^4$, $R^{9'}$ and Y are as defined above.

Step 5

In Step 5, carboxylic acid (VII) and amino derivative (IX) are reacted to give sulfonic acid derivative (Va). This step can be conducted by the same method as in Step 1.

The sulfonic acid derivative of hydroxamic acid (I) of the present invention can be also prepared by the method shown in the following Scheme 3.

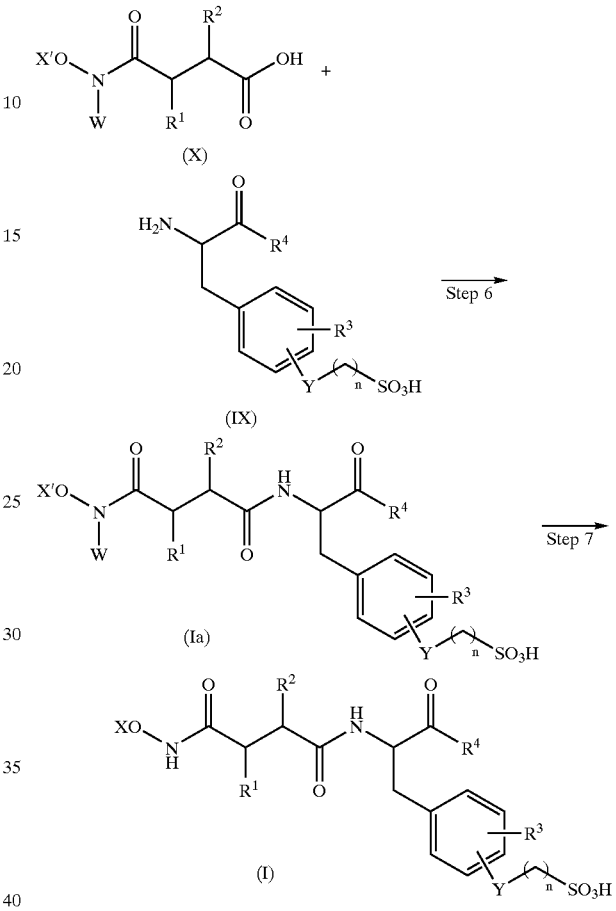

wherein n is an integer of 1 to 6, X' and W are the same or different and as defined for X, and $R^1$, $R^2$, $R^3$, $R^4$, X and Y are as defined above.

Step 6

In Step 6, carboxylic acid (X) and amino derivative (IX) are reacted to give sulfonic acid derivative (Ia). This step can be carried out by the same method as in Step 1.

Step 7

In Step 7, sulfonic acid derivative (Ia) is converted to sulfonic acid derivative of hydroxamic acid (I), and can be carried out by the same method as in Step 4, whether or not W is the same as or different from X.

The carboxylic acid (X) can be prepared by, for example, the method explained in Scheme 6 below. The amino derivatives (VIII) and (IX) can be prepared by, for example, the method to be explained in Scheme 5 below.

The desired substituent $R^1$ can be introduced by the method shown in the aforementioned Schemes 1–3 and without a special step, by the use of carboxylic acid (VII) or (X) having the substituent. In addition, for example, the method shown in the following Scheme 4 can be also used.

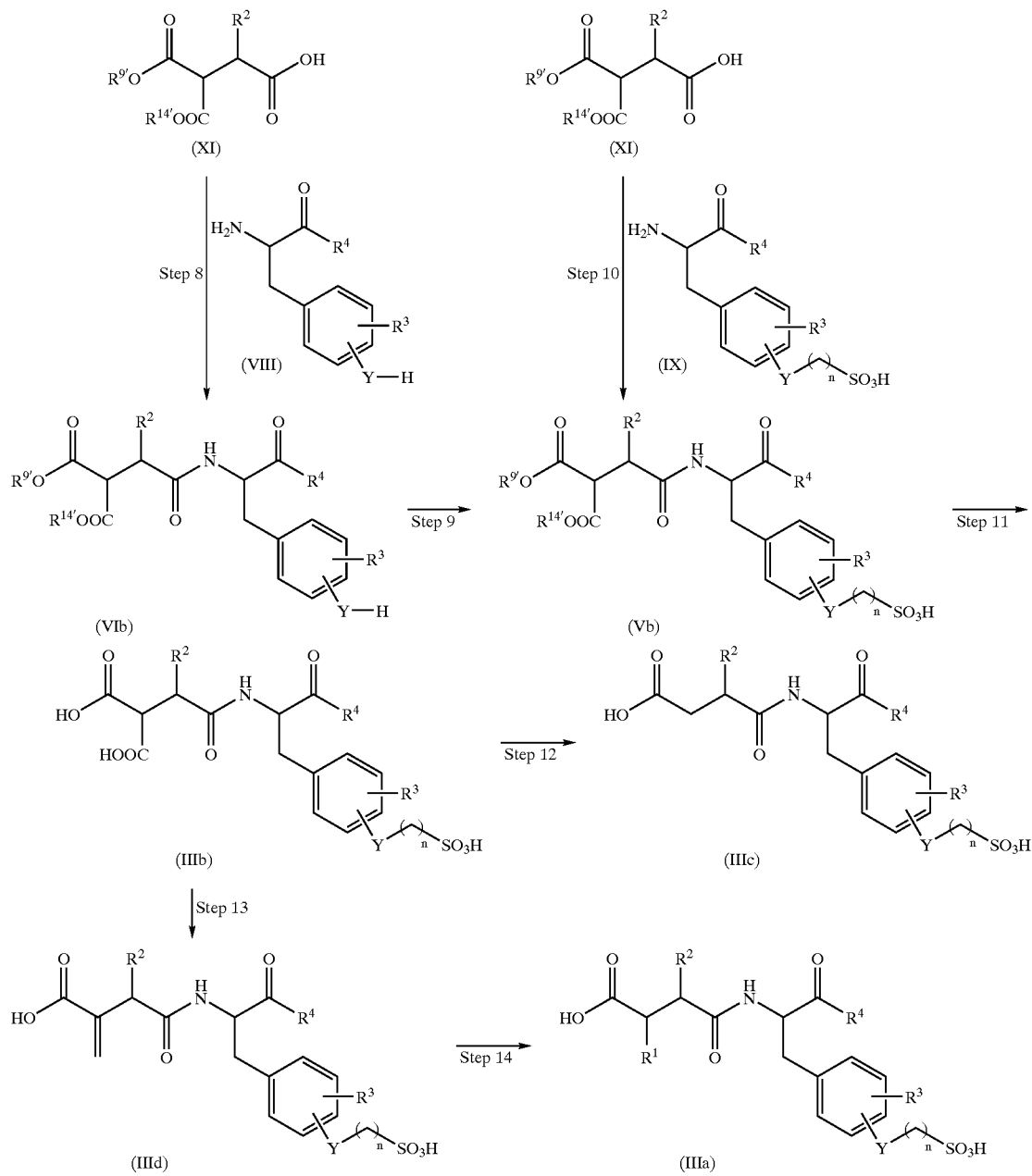

Scheme 4 wherein n is an integer of 1 to 6, $R^1$ is heteroarylthioalkyl, arylthioalkyl, heteroarylalkylthioalkyl of arylalkylthioalkyl, $R^{14'}$ is as defined for $R^{14}$ (except hydrogen), and $R^2$, $R^3$, $R^4$, $R^{9'}$ and Y are as defined above.

Step 8

In Step 8, carboxylic acid (XI) and amino derivative (VIII) are reacted to give intermediate compound (VIb). This step can be conducted by the same method as in Step 1. The carboxylic acid (XI) to be the starting material is described in references (JP-A-7-157470 and the like), or prepared by a conventional method based on these references.

Step 9

In Step 9, intermediate compound (VIb) and haloalkanesulfonic acid or sultone are reacted to give sulfonic acid derivative (Vb). This step can be conducted by the same method as in Step 2.

Step 10

In Step 10, carboxylic acid (XI) and amino derivative (IX) are reacted to give sulfonic acid derivative (Vb). This step can be conducted by the same method as in Step 1.

Step 11

In Step 11, the substituents $R^{9'}$ and $R^{14'}$ of sulfonic acid derivative (Vb) are removed to give sulfonic acid derivative (IIIb). For example, when $R^{9'}$ and $R^{14'}$ are benzyl groups, a general catalytic hydrogenation reaction is carried out in the presence of a metal catalyst at normal pressure or under pressurization. As the metal catalyst, palladium on carbon, palladium black and the like can be used, the solvent used is an ether solvent such as 1,4-dioxane and the like, an ester solvent such as ethyl acetate and the like or an alcohol solvent such as methanol, ethanol, isopropyl alcohol and the like, and the reaction can be carried out at room temperature or under heating.

Step 12

In Step 12, sulfonic acid derivative (IIIb) obtained in Step 11 is subjected to decarboxylation for conversion thereof to sulfonic acid derivative (IIIc). The solvent used is a hydrocarbon solvent such as n-hexane, benzene, toluene and the like, and where necessary, the reaction can be carried out in the presence of a tertiary amine, such as N-methylmorpholine, triethylamine and the like, at room temperature or under heating.

Step 13

In Step 13, sulfonic acid derivative (IIIb) obtained in Step 11 is reacted with formaldehyde in the presence of a secondary amine for conversion thereof to sulfonic acid derivative (IIId). As the secondary amine, piperidine, diethylamine, morpholine and the like are used and the reaction can be carried out in an alcohol solvent such as methanol, ethanol and the like or an amide solvent such as DMF and the like at room temperature or under heating.

Step 14

In Step 14, sulfonic acid derivative (IIId) obtained in Step 13 is reacted with arylthiol, heteroarylthiol, alkylthiol, heteroarylalkylthiol or arylalkylthiol as a nucleophile to give sulfonic acid derivative (IIIa), wherein the substituent $R^1$ is arylthioalkyl, heteroarylthioalkyl, alkylthioalkyl, heteroarylalkylthioalkyl or arylalkylthioalkyl. This reaction can be carried out without solvent or in a halogenated hydrocarbon solvent such as methylene chloride and the like, an alcohol solvent such as methanol and the like or an amide solvent such as DMF and the like at room temperature or under heating.

The amino derivatives (VIII) and (IX) which are starting compounds in Scheme 1–4 can be prepared by the method shown in the following Scheme 5.

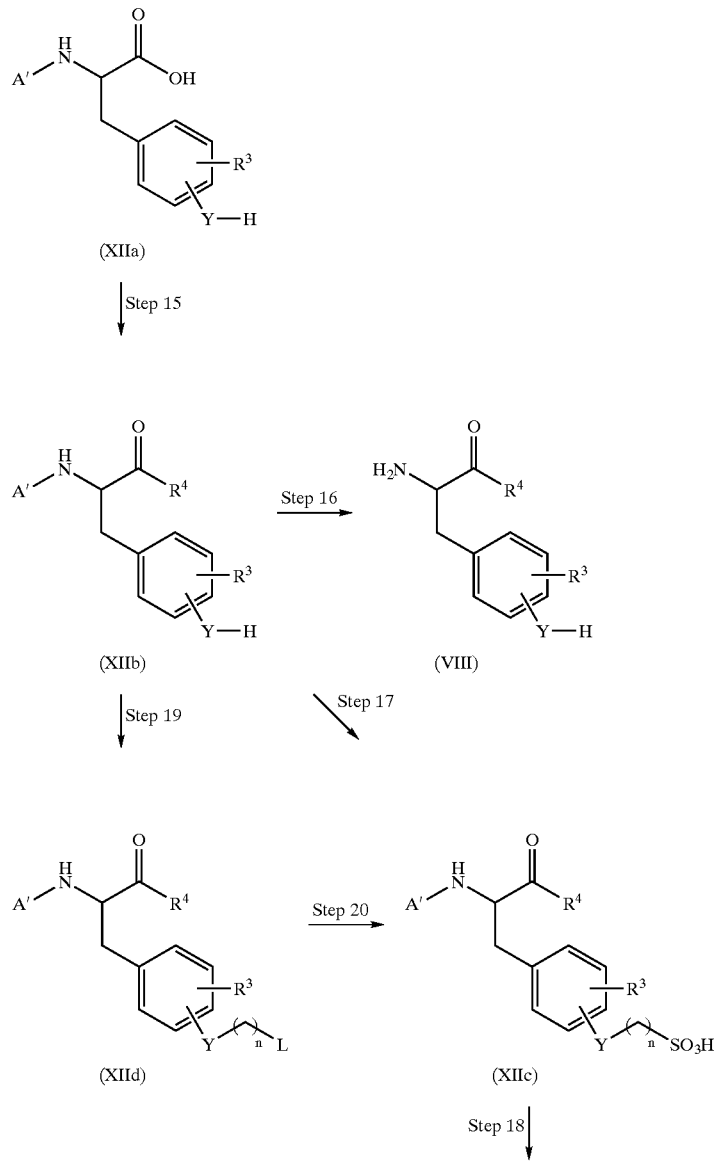

Scheme 5

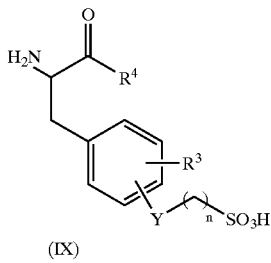

(IX)

wherein n is an integer of 1 to 6, A' is an amino-protecting group such as tert-butoxycarbonyl, benzyloxycarbonyl and the like, L is alkoxy, hydroxyl group, halogen atom such as chlorine, bromine, iodine and the like that can be derived therefrom or sulfonic acid ester such as methanesulfonyloxy, p-toluenesulfonyloxy, trifluoromethanesulfonyloxy and the like, and $R^3$, $R^4$ and Y are as defined above.

Step 15

In Step 15, compound (XIIa) and various amines or alcohol are reacted to give compound (XIIb). This step can be conducted by the same method as in Step 1.

Step 16

In Step 16, the amino-protecting group of compound (XIIb) is removed to give amino derivative (VIII).

When the protecting group A' is tert-butoxycarbonyl group, it can be removed under acidic conditions using trifluoroacetic acid, hydrogen chloride-containing dioxane, hydrogen chloride-containing methanol, hydrogen bromide-containing acetic acid and the like. The inert solvent to be used is preferably a halogenated hydrocarbon solvent such as methylene chloride, chloroform and the like, an ether solvent such as diethyl ether, THF, dioxane and the like, an alcohol solvent such as methanol, ethanol, n-propyl alcohol, isopropyl alcohol and the like, or an organic acid such as acetic acid and the like.

The reaction temperature is generally 0–100° C., preferably 0–50° C. The reaction time is generally 15 min–12 hr, preferably 15 min–4 hr.

When the protecting group A' is benzyloxycarbonyl group, a method for removing by a treatment with an acid or a method for removing by catalytic reduction is preferable.

The acid to be used for the method using an acid is preferably trifluoromethanesulfonic acid. The solvent to be used is preferably methylene chloride. The reaction temperature and the reaction time are preferably 0–50° C. and 5 min–6 hr.

The catalyst to be used for the method based on catalytic reduction is preferably palladium on carbon or palladium black. The solvent to be used is preferably an alcohol solvent such as methanol, ethanol, n-propyl alcohol, isopropyl alcohol and the like, an ether solvent such as diethyl ether, tetrahydrofuran, 1,4-dioxane and the like, an ester solvent such as ethyl acetate and the like. The pressure of hydrogen in this method is generally 1–10 atm, and the reaction temperature and the reaction time are preferably 0–100° C. and 5 min–24 hr.

Step 17

In Step 17, compound (XIIb) and haloalkanesulfonic acid or sultone are reacted to give compound (XIIc). This step can be conducted by the same method as in Step 2.

Step 18

In Step 18, the amino-protecting group of compound (XIIc) is removed to give amino derivative (IX), and can be conducted by the same method as in Step 16.

Step 19

In Step 19, compound (XIIb) is alkylated for conversion thereof to a compound (XIId: L=leaving group) having a leaving group in the terminal, by a single step or stepwisely, which can be conducted by the same method as in method 1) or 2) shown in the following.

Step 19-1) Single Step Synthetic Method

The compound (XIIb) is reacted with an alkylating agent for conversion thereof to a compound (XIId: L=halogen), and can be conducted by the same method as in Step 2. As the alkylating agent, alkyl dihalide having a desired carbon chain, such as dibromomethane, 1,2-dibromoethane, 1-chloro-3-bromopropane, 1-chloro-4-bromobutane, 1-chloro-5-bromopentane and the like can be used.

Step 19-2) Stepwise Synthetic Method

This method consists of the following three steps i) to iii).

i) A step for converting compound (XIIb) to a compound (XIId: L=alkoxy) by reacting with mono-protected diol having a desired carbon chain length by Mitsunobu reaction [J. Med. Chem., 1994, 37, 674] for conversion thereof. As the mono-protected diol, 2-benzyloxyethanol, 2-t-butyldimethylsiloxyethanol, 3-benzyloxypropanol, 4-benzyloxybutanol, 5-benzyloxypentanol and the like can be used. As the activating reagent, triphenylphosphine and diethylazodicarboxylate (DEAD) are preferable. The solvent used is an aprotic solvent such as DMF, acetonitrile, THF, dioxane, methylene chloride, chloroform and the like. This step can be carried out at −15° C. to room temperature or under heating.

ii) A step for converting compound (XIId: L=alkoxy) to compound (XIId: L=hydroxyl group) by deprotection, which can be carried out in the same manner as in Step 4.

iii) A step for converting hydroxyl group of compound (XIId: L=hydroxyl group) to a compound (XIId: L=leaving group) having a leaving group such as halogen, sulfonic acid ester and the like. When L is halogen, this step can be carried out by reacting compound (XIId: L=hydroxyl group) with carbon tetrachloride or carbon tetrabromide in the presence of triphenylphosphine. As the solvent, an aprotic solvent such as acetonitrile, THF, dioxane, methylene chloride, chloroform and the like can be used. The reaction temperature of this step is preferably −15° C. to room temperature or under heating. When L is sulfonic acid ester, this step can be carried out by reacting compound (XIId: L=hydroxyl group) with a desired sulfonylating agent in the presence of an amine base. As the sulfonylating agent, methanesulfonic acid anhydride, trifluoromethanesulfonic acid anhydride and p-toluenesulfonyl chloride are preferable, and as the amine base, triethylamine, pyridine, 2,6-lutidine, 2,4,6-collidine, diisopropylethylamine and the like are preferable. As the solvent, an aprotic solvent such as acetonitrile, THF, dioxane, toluene, methylene chloride, chloroform and the like can be used. The reaction temperature of this step is preferably −15° C. to room temperature.

Step 20

In Step 20, the compound (XIId: L=leaving group) obtained in step 19 is converted to compound (XIIc). This step can be carried out according to the method described in reference [F. Cortes, Organic Synthesis, II, 564 (1943)]. As the hydroxysulfonylating agent, sodium sulfite, sodium hydrogensulfite and the like are preferable. As the solvent, water or water-containing alcohol can be used. The reaction temperature of this step is preferably from room temperature or under heating.

The carboxylic acid (X), which is a starting compound in Scheme 3, can be prepared by the method shown in the following Scheme 6.

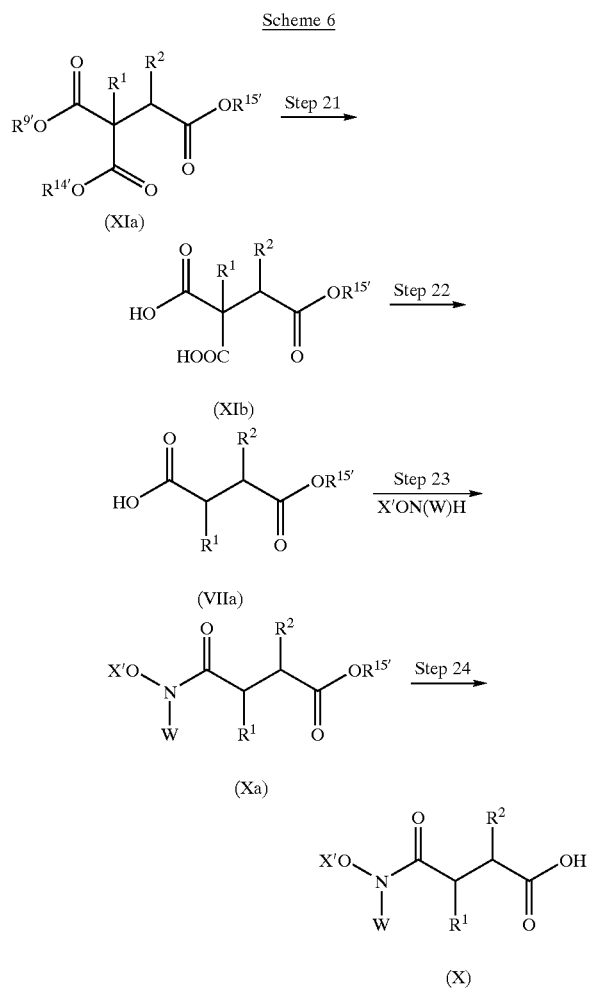

wherein X' and W are as defined for X, $R^{9'}$ and $R^{14'}$ are the same or may, in combination, take a cyclic structure such as methylene group (—$CH_2$—) or dimethylmethylene [—C($CH_3$)$_2$—], $R^{15'}$ is as defined for $R^{9'}$ and $R^{14'}$ (provided that $R^{15'}$ is selected from groups other than $R^{9'}$ and $R^{14'}$), and $R^1$, $R^2$, $R^{9'}$, $R^{14'}$ and X are as defined above.

Step 21

In Step 21, compound (XIa) is converted to compound (XIb) by deprotection. For example, when $R^{15'}$ is benzyl group and $R^{9'}$ and $R^{14'}$ are t-butyl groups, a method similar to that in Step 3 can be employed, and in a reverse case ($R^{15'}$: t-butyl group, $R^{9'}$ and $R^{14'}$: benzyl), the same method as in Step 11 can be employed. The compound (XIa) to be the starting material is a compound described in JP-A-7-157470 or a compound prepared by a conventional method based on this reference.

Step 22

In Step 22, compound (XIb) is converted to compound (VIIa) by decarboxylation, which can be conducted by a method similar to that in Step 12.

Step 23

In Step 23, compound (VIIa) is reacted with N,O-disubstituted hydroxylamine [X'ON(W)H] for conversion thereof to compound (Xa), which can be conducted by a method similar to that in Step 1. The N,O-disubstituted hydroxylamine [X'ON(W)H] can be prepared by a conventional method using O-protected hydroxylamine [X'ONH$_2$] which is commercially available or obtained by the method described in a reference (*Chem. Pharm. Bull. Jpn.* 1975, 23, 167).

Step 24

In Step 24, compound (Xa) is converted to carboxylic acid (X) by deprotection, wherein the protecting group can be removed by the method described in a reference [T. W. Greene et. al., PROTECTIVE GROUPS IN ORGANIC SYNTHESIS, $2^{nd}$ ed., (JOHN WILEY & SONS, Inc.)].

The compound (XIIa), which is a starting compound in Scheme 5, can be prepared by the following method.

The compound (XIIa) can be prepared by protecting an amino group of amino acid represented by the formula

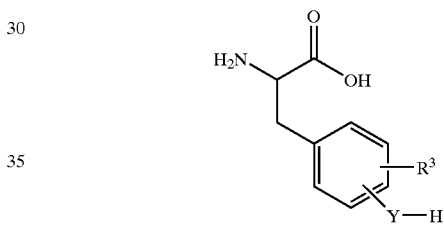

with an amino-protecting group such as tert-butoxycarbonyl group, benzyloxycarbonyl group and the like [e.g., *Pepuchidogousei no kiso to jikken,* Izumiya et al., Maruzen Shoten, p 16].

Preparation Method of Sulfonic Acid Derivative of Hydroxamic Acid, which is Represented by the Formula (II)

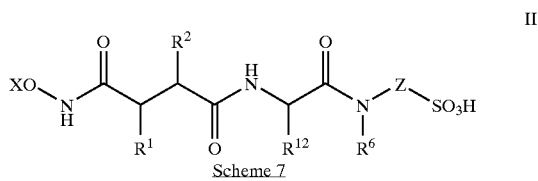

Scheme 7

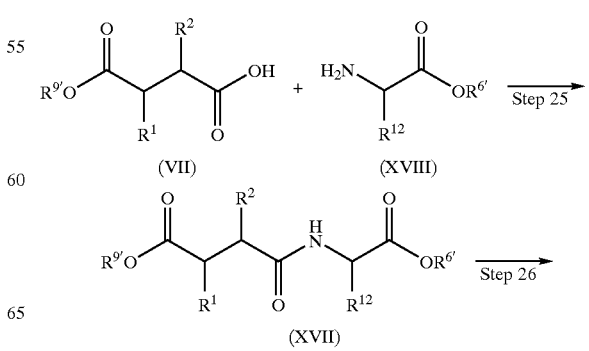

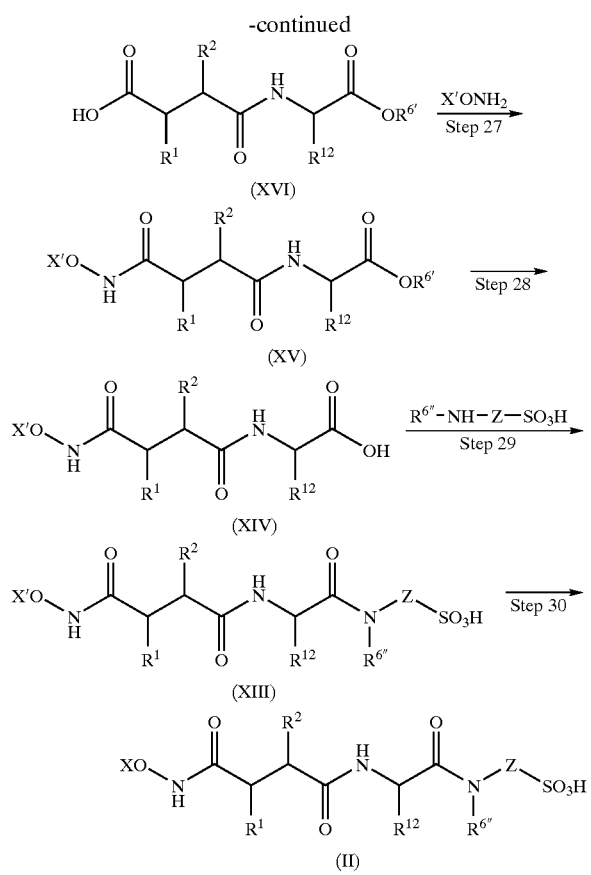

Step 28

In Step 28, O-protected hydroxamic acid derivative (XV) is converted to intermediate compound (XIV) by deprotection. When $R^{6'}$ is benzyl group in this step, a method for deprotection by catalytic reduction is preferable. The catalyst for the method by catalytic reduction is preferably palladium on carbon or palladium black. The solvent is preferably an alcohol solvent such as methanol, ethanol, n-propyl alcohol, isopropyl alcohol and the like, an ether solvent such as diethyl ether, THF, 1,4-dioxane and the like, or an ester solvent such as ethyl acetate and the like. In this reaction, The pressure of hydrogen is generally 1–10 atm, and the reaction temperature and reaction time are preferably 0–100° C. and 5 min–24 hr.

Step 29

In Step 29, intermediate compound (XIV) is reacted with aminoalkanesulfonic acid derivative: $R^{6''}$—NH-Z-$SO_3H$ ($R^{6''}$ and Z are as defined above) to give sulfonic acid derivative of O-protected hydroxamic acid (XIII). This step can be conducted by the same method as in Step 1.

Step 30

In Step 30, sulfonic acid derivative of O-protected hydroxamic acid (XIII) is converted to sulfonic acid derivative of hydroxamic acid (II). The protecting group of sulfonic acid derivative of O-protected hydroxamic acid (XIII) can be removed under general hydroxyl-deprotection conditions as in Step 4.

The sulfonic acid derivative of O-protected hydroxamic acid (XIII) can be also prepared by the method shown in the following Scheme 8.

wherein $R^{6'}$ and $R^{6''}$ are as defined for $R^6$ (provided $R^{6'}$ is not hydrogen), X' is as defined for X, and $R^1$, $R^2$, $R^6$, $R^{12}$, X and Z are as defined above.

The sulfonic acid derivative of hydroxamic acid (II) and a pharmacologically acceptable salt thereof of the present invention can be synthesized by the method shown in Scheme 7. First, carboxylic acid (VII) and amino derivative (XVIII) are condensed by the C-terminal activation method in peptide synthesis [e.g., *Pepuchidogousei no kiso to jikken*, Izumiya et al., Maruzen Shoten, p 91] to give intermediate compound (XVII), which is then converted to succinic acid derivative (XVI). Then, it is converted to O-protected hydroxamic acid derivative (XV), and after conversion to intermediate compound (XIV) and then to sulfonic acid derivative of O-protected hydroxamic acid (XIII), the acid (XIII) is deprotected.

The carboxylic acid (VII) to be the starting material is as the aforementioned, and amino derivative (XVIII) can be prepared by, for example, the method to be explained in the following Scheme 11.

The detail of each step is explained in the following.

Step 25

In Step 25, carboxylic acid (VII) and amino derivative (XVIII) are reacted to give intermediate compound (XVII), which can be conducted by a method similar to that in Step 1.

Step 26

In Step 26, intermediate compound (XVII) is converted to succinic acid derivative (XVI), which can be conducted by a method similar to that in Step 3.

Step 27

In Step 27, succinic acid derivative (XVI) is converted to O-protected hydroxamic acid derivative (XV), which can be conducted by a method similar to that in Step 4.

Scheme 8

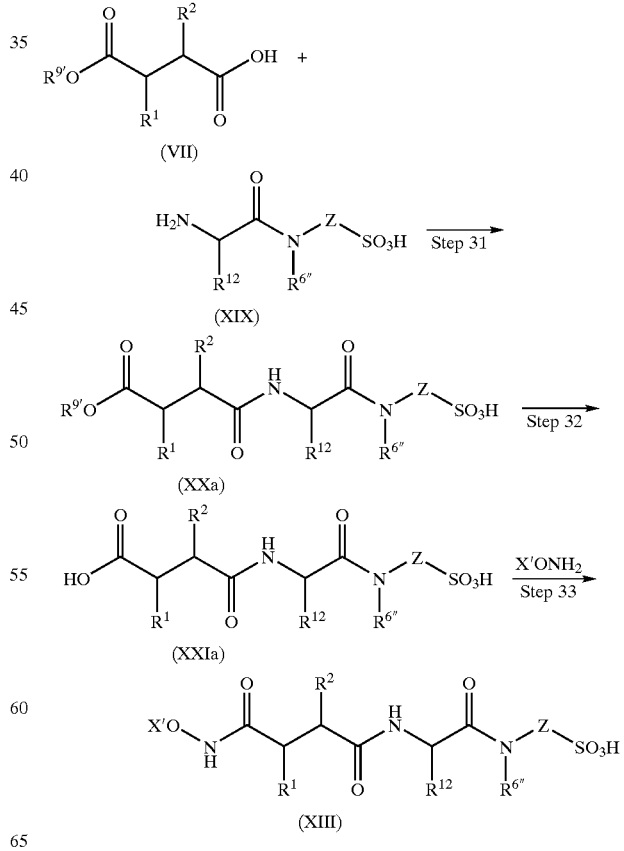

wherein $R^1$, $R^2$, $R^{12}$, $R^{6''}$, $R^{9'}$, X' and Z are as defined above.

Step 31

In Step 31, carboxylic acid (VII) and amino derivative (XIX) are reacted to give intermediate compound (XXa). This step can be conducted by the same method as in Step 1.

Step 32

In Step 32, intermediate compound (XXa) is converted to succinic acid derivative (XXIa). This step can be conducted by the same method as in Step 3.

Step 33

In Step 33, succinic acid derivative (XXIa) is converted to sulfonic acid derivative of O-protected hydroxamic acid (XIII). This step can be conducted by the same method as in Step 4.

The sulfonic acid derivative of O-protected hydroxamic acid (XIII) can be also prepared by a method shown in the following Scheme 9, or a method similar to that shown in Scheme 3 for sulfonic acid derivative of hydroxamic acid (I).

Scheme 9

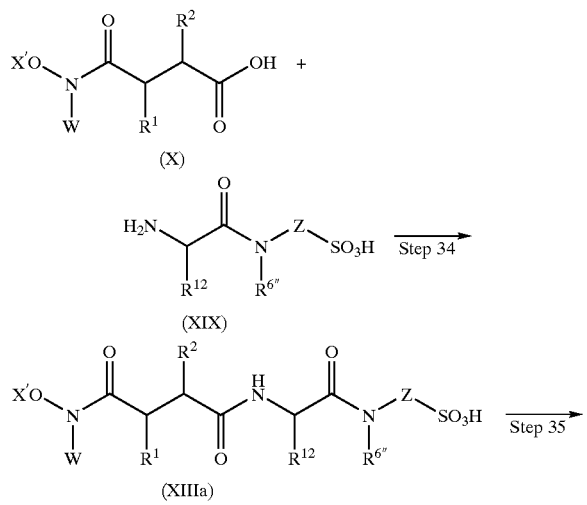

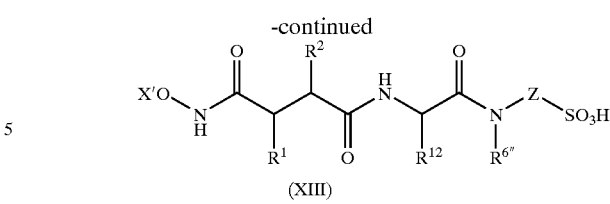

wherein W is as defined for X' and they may be the same or different, and $R^1$, $R^2$, $R^{12}$, $R^{6"}$, X' and Z are as defined above.

Step 34

In Step 34, carboxylic acid (X) and amino derivative (XIX) are reacted to give sulfonic acid derivative (XIIIa). This step can be conducted by the same method as in Step 1.

Step 35

In Step 35, sulfonic acid derivative (XIIIa) is converted to sulfonic acid derivative of hydroxamic acid (XIII). This step can be conducted by the same method as in Step 7.

The carboxylic acid (X) can be prepared according to the aforementioned Scheme 6, and amino derivatives (XVIII) and (XIX) can be prepared by, for example, the method explained in Scheme 11 below.

The desired substituent $R^1$ can be introduced without a special step but by the methods shown in the aforementioned Scheme 7 and Scheme 8 using carboxylic acid (VII) having said substituent. Besides these, for example, it can be also prepared using carboxylic acid (XI) and amino derivative (XIX) by the same method as in Scheme 4 for sulfonic acid derivative of hydroxamic acid (I).

Scheme 10

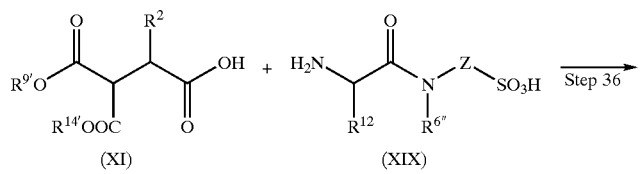

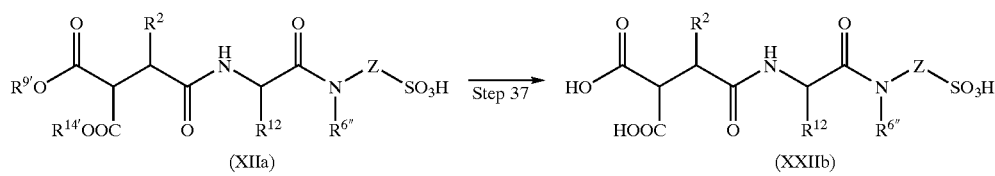

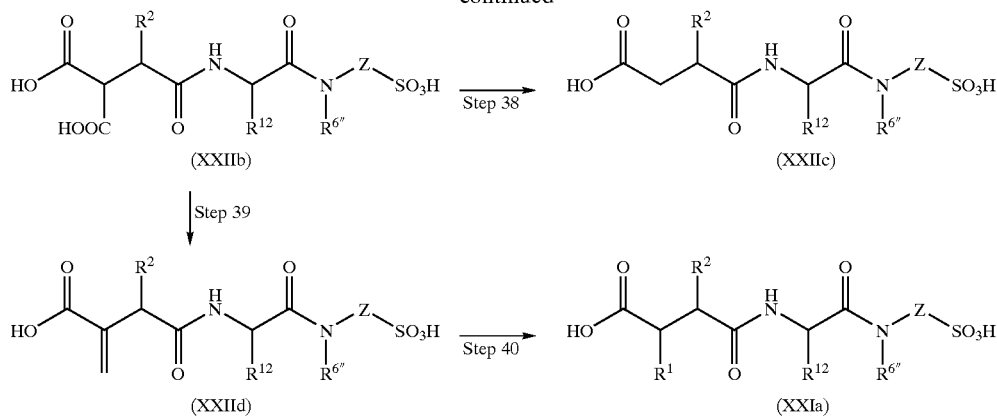

wherein R¹ is heteroarylthioalkyl, arylthioalkyl, heteroarylalkylthioalkyl, alkylthioalkyl or arylalkylthioalkyl, $R^{14'}$ is as defined for $R^{14}$ (except hydrogen), and $R^2$, $R^{12}$, $R^{6''}$, $R^{9'}$ and Z are as defined above.

Step 36

In Step 36, carboxylic acid (XI) and amino derivative (XIX) are reacted to give intermediate compound (XXIIa). This step can be conducted by the same method as in Step 1. The carboxylic acid (XI) to be the starting material is a compound described in references (JP-A-7-157470 and the like) or a compound prepared by a conventional method based on the references.

Step 37

In Step 37, the substituents $R^{9'}$ and $R^{14'}$ of intermediate compound (XXIIa) are removed to give succinic acid derivative (XXIIb). This step can be conducted by the same method as in Step 11.

Step 38

In Step 38, succinic acid derivative (XXIIb) obtained in Step 37 is converted to succinic acid derivative (XXIIc) by decarboxylation. This step can be conducted by the same method as in Step 12.

Step 39

In Step 39, succinic acid derivative (XXIIb) obtained in Step 37 is converted to succinic acid derivative (XXIId) by reaction with formaldehyde in the presence of a secondary amine. This step can be conducted by the same method as in Step 13.

Step 40

In Step 40, succinic acid derivative (XXIId) obtained in Step 39 is reacted with arylthiol, heteroarylthiol, alkylthiol, heteroarylalkylthiol or arylalkylthiol as a nucleophile to give succinic acid derivative (XXIa) wherein the substituent R¹ is arylthioalkyl, heteroarylthioalkyl, alkylthioalkyl, heteroarylalkylthioalkyl or arylalkylthioalkyl. This step can be conducted by the same method as in Step 14.

The amino derivatives (XVIII) and (XIX), which are the starting compounds in Schemes 7–10, can be prepared by the method shown in the following Scheme 11.

Scheme 11

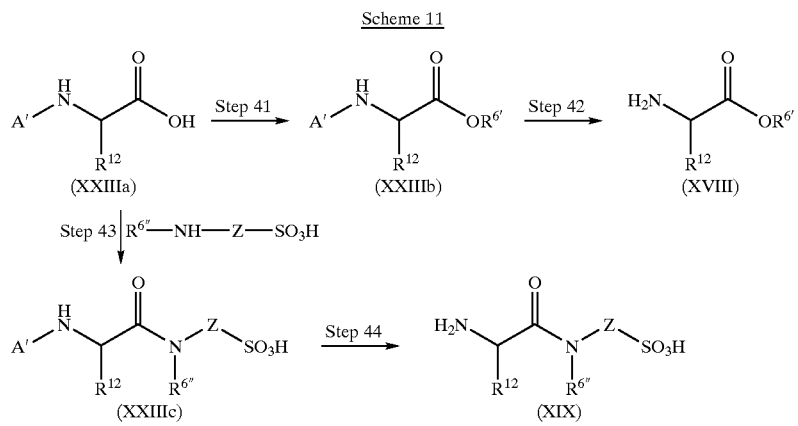

wherein A' is amino-protecting group such as tert-butoxycarbonyl, benzyloxycarbonyl and the like, and $R^{12}$, $R^{6'}$, $R^{6''}$ and Z are as defined above.

Step 41

In Step 41, compound (XXIIIa) and an alcohol derivative such as benzyl alcohol and the like are reacted to give compound (XXIIIb). This step can be conducted by the same method as in Step 1.

Step 42

In Step 42, amino-protecting group of compound (XXIIIb) is removed to give amino derivative (XVIII), which can be conducted by the same method as in Step 16.

Step 43

In Step 43, compound (XXIIIa) and aminoalkanesulfonic acid derivative: $R^{6''}$—NH-Z-SO₃H ($R^{6''}$ and Z are as defined above) are reacted to give compound (XXIIIc). This step can be conducted by the same method as in Step 29.

Step 44

In Step 44, amino-protecting group of compound (XXIIIc) is removed to give amino derivative (XIX), which can be conducted by the same method as in Step 16.

The compound (XXIIIa), which is the starting compound in Scheme 10, can be prepared by the following method.

The compound (XXIIIa) can be prepared by protecting amino group of amino acid of the formula

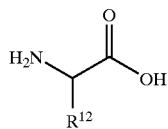

with amino protecting group such as tert-butoxycarbonyl group, benzyloxycarbonyl group and the like [e.g., *Pepuchidogousei no kiso to jikken*, Izumiya et al., Maruzen Shoten, p 16].

It is not that conversion and the like between various substituents including $R^3$ is possible only in a particular step, but possible in any step as long as it is under the conditions non-influential on other functional groups present in the chemical structural formula.

The sulfonic acid derivative of hydroxamic acid of the present invention thus synthesized can be recovered at an optional purity by appropriately applying known separation and purification means, such as concentration, extraction, chromatography, reprecipitation, recrystallization and the like.

In addition, pharmacologically acceptable salt and solvate of the sulfonic acid derivative of hydroxamic acid can be prepared by a known method. Moreover, various isomers and the like of the sulfonic acid derivative of hydroxamic acid can be prepared by a known method.

When the sulfonic acid derivative of hydroxamic acid and a pharmacologically acceptable salt thereof of the present invention have a superior LPS inhibitory action on mammals (e.g., human, dog, cat and the like) and are low toxic.

Therefore, the sulfonic acid derivative of hydroxamic acid and a pharmacologically acceptable salt thereof of the present invention are useful as an inhibitor of LPS, and are useful for the prophylaxis or treatment of diseases such as sepsis, MOF, chronic articular rheumatism, Crohn's disease, cachexia, myasthenia gravis, systemic lupus erythematodes, asthma, TYPE I diabetes, psoriasis, other autoimmune diseases, inflammatory diseases and the like.

When the sulfonic acid derivative of hydroxamic acid or a pharmacologically acceptable salt thereof of the present invention is used as a pharmaceutical product, a pharmacologically acceptable carrier and the like are used and can be administered orally or parenterally as a pharmaceutical composition in the form of granule, tablet, capsule, injection, ointment, eye-drop, nose-drop, cream, aerosol and the like. Particularly, the sulfonic acid derivative of hydroxamic acid and a pharmacologically acceptable salt thereof are superior in water-solubility and are preferable for preparation of a water-soluble pharmaceutical composition such as injection, eye-drop, nose-drop, agent for drip and the like.

The above-mentioned preparation contains an effective amount of the sulfonic acid derivative of hydroxamic acid or a pharmacologically acceptable salt thereof.

The dose of the sulfonic acid derivative of hydroxamic acid or a pharmacologically acceptable salt thereof varies depending on the administration route, condition, body weight or age of patients, and the like, and can be appropriately determined according to the administration object.

For oral administration to an adult, it is generally 0.01–1,000 mg/kg body weight/day, preferably 0.05–250 mg/kg body weight/day, which is preferably administered once a day or in several doses a day.

The present invention is explained in detail in the following by referring to examples, which are not to be construed as limitative.

$^1$H-NMR was measured at 270 MHz or 300 MHz. The chemical shift of $^1$H-NMR is expressed in relative delta ($\delta$) values in parts per million (ppm) using tetramethylsilane as the internal standard. For the coupling constant, obvious multiplicity is shown in hertz (Hz) using s (singlet), d (doublet), t (triplet), q (quartet), m (multiplet), dd (doublet of doublet), br s (broad singlet) and the like.

EXAMPLE 1

5-methyl-3(R)-{1(S)-methylcarbamoyl-2-[4-(3-sulfopropoxy)phenyl]ethylcarbamoyl}-2(R or S)-phthalimidomethylhexanohydroxamic acid sodium salt

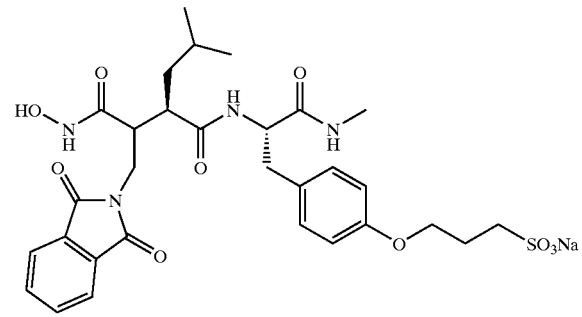

(1) 1,2-dibenzyl 1-tert-butyl 4-methyl-1,1,2-(R)-pentanetricarboxylate

Using (D)-leucine as a starting material and in the same manner as in the method described in JP-A-4-352757, synthesis was performed.

$^1$H-NMR (CDCl$_3$) $\delta$ 7.45–7.20 (m, 10H), 5.25–4.93 (m, 4H), 3.68 and 3.65 (d, J=9.8 Hz, 1H), 3.25–3.08 (m, 1H), 1.68–1.38 (m, 2H), 1.34 and 1.33 (s, 9H), 1.35–1.05 (m, 1H), 0.90, 0.84, 0.83 and 0.78 (d, J=6.4 Hz, 6H).

(2) 4-tert-butoxy-2(R)-isobutyl-3(R or S)-phthalimidomethylsuccinic acid

Using the title compound of Example 1(1) and N-bromomethylphthalimide and in the same manner as in the method described in JP-A-4-352757, a crude product was obtained. Purification was performed according to the following method. A crude product (607 g, about 1.32 mol) was dissolved in diisopropyl ether (6 L), cyclohexylamine (151 mL, 1.32 mol) was added under ice-cooling, and the mixture was stirred for 1.5 hr. The precipitate was collected by filtration, washed (diisopropyl ether) and air-dried. The obtained solid was suspended in ethyl acetate (0.4 L), and washed successively with 2N aqueous sulfuric acid solution (1.32 L), water (2 L×2) and saturated brine (2 L). The organic layer was dried over anhydrous magnesium sulfate, and after treatment with active carbon (25 g/70° C./30 min), filtrated. The filtrate was concentrated under reduced pressure to give the title compound (467.6 g, 91%, 68% de) as an oil.

$^1$H-NMR (CDCl$_3$) $\delta$ 7.90–7.65 (m, 4H), 4.13 (dd, J=14.0, 9.1 Hz, 1H), 3.77 (dd, J=14.0, 5.4 Hz, 1H), 3.25–3.10 (m, 1H), 2.88–2.75 (m, 1H), 1.85–1.60 (m, 2H), 1.35 (s, 9H), 1.35–1.20 (m, 1H), 0.93 (d, J=6.5 Hz, 6H).

(3) N$^\alpha$-(tert-butoxycarbonyl)-L-tyrosine N-methylamide

To a solution of N-(tert-butoxycarbonyl)-L-tyrosine (300 g, 1.07 mol) in DMF (2 L) were successively added methylamine hydrochloride (86.4 g, 1.28 mol), 1-hydroxybenzotriazole monohydrate (163 g, 1.07 mol, hereinafter to be abbreviated as HOBt.H$_2$O), N-methylmorpholine (258 mL, 2.35 mol) and 1-ethyl-3-(3-dimethylaminopropyl)carbodiimide hydrochloride (245 g, 1.28 mol, hereinafter to be abbreviated as WSCI.HCl), under ice-cooling (internal temperature 10° C.). The reaction mixture was stirred for 70 hr while gradually raising the temperature to room temperature. The reaction mixture was poured into iced water (10 L), and the precipitate was collected by filtration and washed with water and ether. The obtained precipitate was recrystallized from ethyl acetate (7 L) to give the title compound (265 g, 84%) as white crystals.

$^1$H-NMR (DMSO-d$_6$) δ 9.14 (s, 1H), 7.76 (d, J=4.5 Hz, 1H), 7.00 (d, J=8.1 Hz, 2H), 6.77 (d, J=8.4 Hz, 2H), 6.63 (d, J=8.1 Hz, 2H), 4.08–3.85 (m, 1H), 2.79 (dd, J=13.7, 4.7 Hz, 1H), 2.70–2.55 (m, 1H), 2.56 (d, J=4.2 Hz, 3H), 1.37 (s, 9H).

(4) L-tyrosine N-methylamide Hydrochloride

The title compound (160 g, 0.54 mol) of Example 1 (3) was dissolved in a mixed solvent of chloroform (800 mL) and methanol (400 mL), and anisole (295 mL, 2.72 mol) and a 4N hydrochloric acid-dioxane solution (800 mL) were added under ice-cooling (internal temperature 7° C.). The mixture was stirred at the same temperature for 2 hr and at room temperature for 2 hr. Diisopropyl ether (2 L) was added to the reaction solution, and the precipitate was collected by filtration, washed with diisopropyl ether, and dried to give the title compound (125 g, quantitative determination) as a white solid.

$[\alpha]_D^{24}$=+75.2 (c=1.0, H$_2$O). $^1$H-NMR (DMSO-d$_6$) δ 9.80–9.05 (br, 1H), 8.41 (q, J=4.8 Hz, 1H), 8.40–8.00 (br, 3H), 7.00 (d, J=8.4 Hz, 2H), 6.71 (d, J=8.4 Hz, 2H), 3.90–3.75 (m, 1H), 2.93 (dd, J=13.8, 6.9 Hz, 1H), 2.87 (dd, J=13.8, 7.2 Hz, 1H), 2.58 (d, J=4.8 Hz, 3H).

(5) tert-butyl 3(R)-[2-(4-hydroxyphenyl)-1(S)-(methylcarbamoyl)ethylcarbamoyl]-5-methyl-2(R or S)-phthalimidomethylhexanoate To a solution of the title compound (200 g, 0.51 mol) of Example 1 (2) and the title compound (118 g, 0.51 mol) of Example 1 (4) in DMF (1 L) were successively added HOBt.H$_2$O (78.6 g, 0.51 mol), N-methylmorpholine (113 mL, 1.03 mol) and WSCI.HCl (118 g, 0.62 mol) under ice-cooling (internal temperature 10° C.). The reaction mixture was stirred for 16 hr while gradually raising the temperature to room temperature. The reaction solution was poured into iced water (5 L), and the precipitate was collected by filtration. The obtained precipitate was dissolved in ethyl acetate (3 L), and washed successively with 0.5N hydrochloric acid, water, saturated aqueous sodium hydrogencarbonate solution, water and saturated brine (1 L each), dried (anhydrous magnesium sulfate) and concentrated under reduced pressure. The obtained residue was recrystallized from ethyl acetate (1.9 L)-diisopropyl ether (1 L) to give the title compound (201 g, 69%) as white crystals.

$^1$H-NMR (DMSO-d$_6$) δ 8.75 (s, 1H), 8.37 (d, J=9.0 Hz, 1H), 7.95–7.70 (m, 5H), 7.04 (d, J=8.4 Hz, 2H), 6.46 (d, J=8.4 Hz, 2H), 4.65–4.50 (m, 1H), 3.40 (dd, J=13.7, 11.7 Hz, 1H), 2.87 (dd, J=13.7, 4.5 Hz, 1H), 2.70–2.50 (m, 3H), 2.59 (d, J=4.8 Hz, 3H), 2.27 (dd, J=13.7, 5.1 Hz, 1H), 1.58–1.44 (m, 1H), 1.42–1.25 (m, 1H), 1.09 (s, 9H), 0.90–0.70 (m, 1H), 0.84 (d, J=6.6 Hz, 3H), 0.76 (d, J=6.6 Hz, 3H).

(6) tert-butyl 5-methyl-3(R)-{1(S)-methylcarbamoyl-2-[4-(3-sulfopropoxy)phenyl]ethylcarbamoyl}-2(R or S)-phthalimidomethylhexanoate cesium salt To a solution of the title compound (91.2 g, 161 mmol) of Example 1 (5) in DMF (500 mL) were added 1,3-propanesultone (21.7 g, 177 mmol) and cesium carbonate (57.8 g, 177 mmol) at room temperature, and the mixture was stirred for 45 hr. Diisopropyl ether (2 L) was added to the reaction solution, and the precipitate was collected by filtration, washed with ethyl acetate and dried to give the title compound (159 g, quantitative determination) as a white solid.

$^1$H-NMR (DMSO-d$_6$) δ 8.43 (d, J=9.0 Hz, 1H), 8.00–7.80 (m, 5H), 7.17 (d, J=8.4 Hz, 2H), 6.57 (d, J=8.4 Hz, 2H), 4.70–4.55 (m, 1H), 3.70–3.10 (m, 3H), 3.00–2.85 (m, 1H), 2.75–2.35 (m, 3H), 2.61 (d, J=4.5 Hz, 3H), 2.16 (t, J=7.4 Hz, 2H), 1.98 (dd, J=13.5, 4.5 Hz, 1H), 1.60–1.42 (m, 1H), 1.40–1.20 (m, 3H), 1.09 (s, 9H), 0.90–0.70 (m, 1H), 0.85 (d, J=6.5 Hz, 3H), 0.76 (d, J=6.5 Hz, 3H).

(7) 5-methyl-3(R)-{1(S)-methylcarbamoyl-2-[4-(3-sulfopropoxy)phenyl]ethylcarbamoyl}-2(R or S)-phthalimidomethylhexanoic acid The title compound (159 g, 161 mmol) of Example 1 (6) was suspended in methylene chloride (500 mL) and trifluoroacetic acid (500 mL) was added under ice-cooling (internal temperature 5° C.). The mixture was stirred at room temperature for 4.5 hr. Diisopropyl ether (2 L) was added to the reaction solution, and the precipitate was collected by filtration. The obtained precipitate was recrystallized from 1.2N hydrochloric acid (3.5 L) to give the title compound (77.7 g, 76%) as white crystals.

$^1$H-NMR (DMSO-d$_6$) δ 8.37 (d, J=8.8 Hz, 1H), 7.95–7.80 (m, 5H), 7.17 (d, J=8.6 Hz, 2H), 6.57 (d, J=8.6 Hz, 2H), 4.75–4.57 (m, 1H), 3.55–3.35 (m, 2H), 3.24 (dd, J=13.5, 11.1 Hz, 1H), 2.93 (dd, J=13.6, 3.9 Hz, 1H), 2.72–2.55 (m, 1H), 2.62 (d, J=4.6 Hz, 3H), 2.55–2.42 (m, 2H), 2.22 (t, J=7.4 Hz, 2H), 2.07 (dd, J=13.5, 3.7 Hz, 1H), 1.60–1.20 (m, 4H), 0.95–0.75 (m, 1H), 0.84 (d, J=6.5 Hz, 3H), 0.76 (d, J=6.5 Hz, 3H).

(8) 2-tetrahydropyranyl 5-methyl-3(R)-{1(S)-methylcarbamoyl-2-[4-(3-sulfopropoxy)phenyl]ethylcarbamoyl}-2(R or S)-phthalimidomethylhexanohydroxamate sodium salt To a solution of the title compound (13.80 g, 21.8 mmol) of Example 1 (7) in DMF (50 mL) were added successively N-methylmorpholine (4.8 mL, 43.7 mmol), O-2-tetrahydropyranylhydroxylamine (3.07 g, 26.2 mmol), HOBt.H$_2$O (3.35 g, 21.8 mmol) and WSCI.HCl (5.03 g, 26.2 mmol) under ice-cooling (internal temperature 10° C.). The reaction mixture was stirred for 18 hr while gradually raising the temperature to room temperature. The reaction solution was poured into an aqueous solution (500 mL) of sodium dihydrogenphosphate dihydrate (17.00 g, 109 mmol), saturated with sodium chloride and extracted (500 mL×3) with a mixed solvent of THF-methanol (10/1). Butanol was added to the extract solution and the mixture was concentrated under reduced pressure. Diisopropyl ether (1 L) was added to the residue, and the precipitate was collected by filtration and dried to give the title compound (30.20 g, quantitative determination) as a white solid.

$^1$H-NMR (DMSO-$d_6$) δ 10.89 and 10.85 (br s, 1H), 8.36 (d, J=8.7 Hz, 1H), 8.00–7.88 (m, 1H), 7.88–7.75 (m, 4H), 7.19 (d, J=8.7 Hz, 2H), 6.53 (d, J=8.7 Hz, 2H), 4.70–4.55 (m, 1H), 4.52 and 4.37 (br s, 1H), 3.75–3.00 (m, 5H), 2.93 (dd, J=13.7, 4.1 Hz, 1H), 2.78–2.58 (m, 2H), 2.61 (d, J=4.5 Hz, 3H), 2.58–2.23 (m, 2H), 2.18 (t, J=7.4 Hz, 2H), 2.00–1.80 (m, 1H), 1.60–1.20 (m, 10H), 0.90–0.70 (m, 1H), 0.82 (d, J=6.5 Hz, 3H), 0.75 (d, J=6.5 Hz, 3H).

(9) 5-methyl-3(R)-{1(S)-methylcarbamoyl-2-[4-(3-sulfopropoxy)phenyl]ethylcarbamoyl}-2(R or S)-phthalimidomethylhexanohydroxamic acid sodium salt The title compound (30.20 g, 21.8 mmol) of Example 1 (8) was suspended in a mixed solvent of water (50 mL)-methanol (50 mL)-THF (50 mL), and 2.4N hydrochloric acid (50 mL) was added at room temperature. The mixture was stirred for 3 hr. Methanol and THF were distilled away under reduced pressure from the reaction solution, and the precipitate was collected by filtration and washed with isopropyl alcohol and diisopropyl ether. The obtained precipitate was suspended in water (600 mL) and neutralized with sodium hydrogencarbonate (1.84 g, 21.8 mmol). The obtained aqueous solution was purified using a synthetic adsorbent column (DIAION HP-20: water, 50% aqueous methanol solution), and the fractions eluted with a 50% aqueous methanol solution were collected and concentrated under reduced pressure until the precipitate appeared. The residue was recrystallized from water-isopropyl alcohol to give the title compound (4.01 g, 27%) as white crystals.

$[\alpha]_D^{20}$=−50.3 (c=1.0, MeOH) $^1$H-NMR (DMSO-$d_6$) δ 10.28 (br s, 1H), 8.57 (br s, 1H), 8.28 (d, J=8.7 Hz, 1H), 7.90–7.70 (m, 5H), 7.17 (d, J=8.6 Hz, 2H), 6.53 (d, J=8.6 Hz, 2H), 4.70–4.52 (m, 1H), 3.50–3.20 (m, 3H), 2.91 (dd, J=13.5, 3.3 Hz, 1H), 2.72–2.58 (m, 1H), 2.61 (d, J=4.5 Hz, 3H), 2.50–2.25 (m, 2H), 2.16 (t, J=7.3 Hz, 2H), 1.90 (dd, J=13.6, 3.6 Hz, 1H), 1.50–1.20 (m, 4H), 0.90–0.65 (m, 1H), 0.82 (d, J=6.5 Hz, 3H), 0.76 (d, J=6.5 Hz, 3H).

EXAMPLE 2

5-methyl-3(R)-{1(S)-methylcarbamoyl-2-[4-(3-sulfopropoxy)phenyl]ethylcarbamoyl}-2(R or S)-phthalimidomethylhexanohydroxamic acid potassium salt

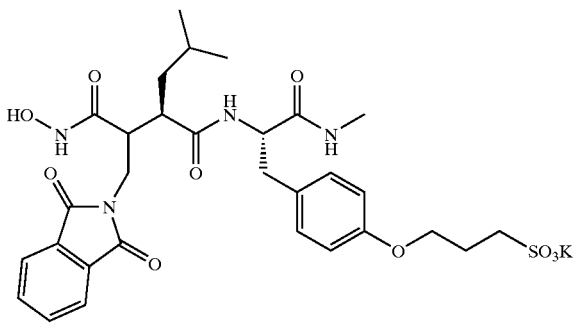

(1) 2-tetrahydropyranyl 5-methyl-3(R)-{1(S)-methylcarbamoyl-2-[4-(3-sulfopropoxy)phenyl]ethylcarbamoyl}-2(R or S)-phthalimidomethylhexanohydroxamate potassium salt To a solution of the title compound (5.00 g, 7.20 mmol) of Example 1 (7) in DMF (50 mL) were added successively N-methylmorpholine (1.58 mL, 14.39 mmol), O-2-tetrahydropyranylhydroxylamine (1.26 g, 10.80 mmol), HOBt.H$_2$O (1.10 g, 7.20 mmol) and diisopropylcarbodiimide (1.36 g, 10.80 mmol, hereinafter to be abbreviated as DIPCI) under ice-cooling (internal temperature 10° C.). The mixture was stirred for 21 hr while gradually raising the temperature to room temperature. A solution of potassium acetate (0.71 g, 7.20 mmol) in acetic acid (10 mL) was added to the reaction solution, and after stirring the mixture for 1 hr, diisopropyl ether was added. The precipitate was collected by filtration. The obtained precipitate was washed with diisopropyl ether and dried to give the title compound (5.82 g, quantitative determination) as a white solid.

$^1$H-NMR (DMSO-$d_6$) δ 10.87 and 10.83 (br s, 1H), 8.30 (d, J=8.6 Hz, 1H), 7.90–7.70 (m, 5H), 7.18 (d, J=8.6 Hz, 2H), 6.54 (d, J=8.6 Hz, 2H), 4.70–4.55 (m, 1H), 4.53 and 4.38 (br s, 1H), 3.75–3.12 (m, 4H), 3.12–2.55 (m, 3H), 2.62 (d, J=4.6 Hz, 3H), 2.55–2.22 (m, 2H), 2.18 (t, J=7.3 Hz, 2H), 2.00–1.85 (m, 1H), 1.60–1.15 (m, 10H), 0.90–0.70 (m, 1H), 0.82 (d, J=6.6 Hz, 3H), 0.75 (d, J=6.6 Hz, 3H).

(2) 5-methyl-3(R)-{1(S)-methylcarbamoyl-2-[4-(3-sulfopropoxy)phenyl]ethylcarbamoyl}-2(R or S)-phthalimidomethylhexanohydroxamic acid potassium salt To a solution of the title compound (5.82 g, about 7.20 mmol) of Example 2 (1) in methanol (100 mL) was added a solution of 5% hydrogen chloride in methanol (50 mL), and the mixture was stirred at 30° C. for 1.5 hr. Diisopropyl ether (450 mL) was added to the reaction solution, and the precipitate was collected by filtration and washed with diisopropyl ether. The obtained precipitate was recrystallized from water-isopropyl alcohol to give the title compound (2.85 g, 58%) as white crystals.

$^1$H-NMR (DMSO-$d_6$) δ 10.27 (br s, 1H), 8.55 (br s, 1H), 8.27 (d, J=8.6 Hz, 1H), 7.90–7.70 (m, 5H), 7.17 (d, J=8.6 Hz, 2H), 6.53 (d, J=8.6 Hz, 2H), 4.68–4.52 (m, 1H), 3.50–3.20 (m, 3H), 2.91 (dd, J=13.9, 4.0 Hz, 1H), 2.75–2.60 (m, 1H), 2.61 (d, J=4.6 Hz, 3H), 2.55–2.25 (m, 2H), 2.17 (t, J=7.3 Hz, 2H), 1.94 (dd, J=13.5, 3.6 Hz, 1H), 1.50–1.20 (m, 4H), 0.90–0.70 (m, 1H), 0.82 (d, J=6.3 Hz, 3H), 0.76 (d, J=6.3 Hz, 3H).

EXAMPLE 3

5-methyl-3(R)-{1(R)-methylcarbamoyl-2-[4-(3-sulfopropoxy)phenyl]ethylcarbamoyl}-2(R or S)-phthalimidomethylhexanohydroxamic acid sodium salt [One Kind of Diastereomer of Compound of Example 1]

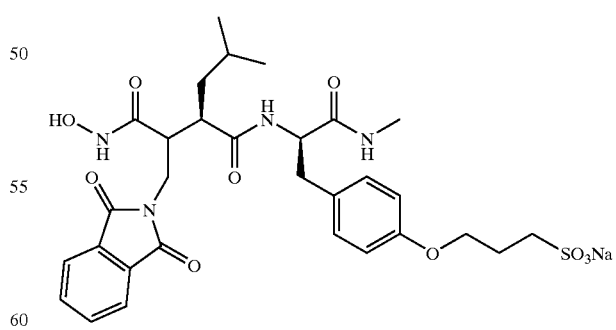

(1) N$^\alpha$-(tert-butoxycarbonyl)-D-tyrosine N-methylamide

Using N-(tert-butoxycarbonyl)-D-tyrosine, and in the same manner as in the method described in Example 1 (3), synthesis was performed.

(2) D-tyrosine N-methylamide hydrochloride

Using the title compound of Example 3 (1), and in the same manner as in the method described in Example 1 (4), synthesis was performed.

$[\alpha]_D^{22}=-73.1$ (c=1.0, H$_2$O)

(3) 5-methyl-3(R)-{1(R)-methylcarbamoyl-2-[4-(3-sulfopropoxy)phenyl]ethylcarbamoyl}-2(R or S)-phthalimidomethylhexanohydroxamic acid sodium salt Using the title compound of Example 1 (2) and the title compound of Example 3 (2), and in the same manner as in the method described in Example 1 (5)–(9), synthesis was performed.

$^1$H-NMR (DMSO-d$_6$) δ 10.43 (s, 1H), 8.66 (s, 1H), 8.37 (d, J=8.4 Hz, 1H), 8.01 (d, J=4.8 Hz, 1H), 7.83 (s, 4H), 7.14 (d, J=8.4 Hz, 2H), 6.78 (d, J=8.4 Hz, 2H), 4.49–4.42 (m, 1H), 3.98 (dt, J=13.0, 5.9 Hz, 2H), 4.02–3.94 (m, 1H), 3.48–3.38 (m, 1H), 3.00 (dd, J=14.2, 4.2 Hz, 1H), 2.60 (d, J=4.5 Hz, 3H), 2.00 (dt, J=14.9, 6.5 Hz, 2H), 1.40 (app t, J=10.4 Hz, 1H), 0.85–0.68 (m, 2H), 0.63 (d, J=5.5 Hz, 3H), 0.59 (d, J=5.6 Hz, 3H).

EXAMPLE 4

5-methyl-3(R)-{1(S)-methylcarbamoyl-2-[4-(3-sulfopropoxy)phenyl]ethylcarbamoyl}-2(R or S)-phthalimidomethylhexanohydroxamic acid sodium salt [One Kind of Diastereomer of Compound of Example 1]

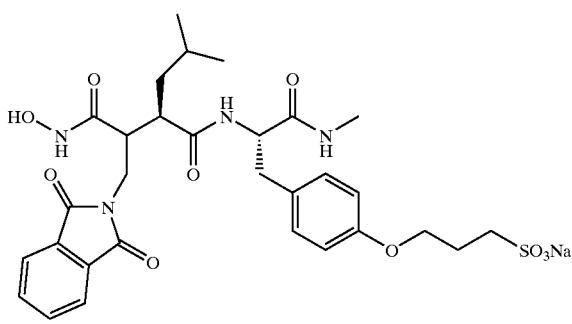

(1) 4-tert-butoxy-2(R)-isobutyl-3(R or S)-phthalimidomethylsuccinic acid [One Kind of Diastereomer of Compound of Example 1 (2)]

The title compound of Example 1 (2) was obtained by purification by column chromatography.

$^1$H-NMR (DMSO-d$_6$) δ 7.89–7.82 (m, 2H), 7.75–7.68 (m, 2H), 4.09 (dd, J=15.4, 10.2 Hz, 1H), 3.83 (dd, J=15.4, 5.9 Hz, 1H), 3.15–3.07 (m, 1H), 2.82–2.74 (m, 1H), 1.79–1.60 (m, 2H), 1.54–1.38 (m, 1H), 1.32 (s, 9H), 0.94 (d, J=7.4 Hz, 3H), 0.92 (d, J=7.4 Hz, 3H).

(2) N$^\alpha$-(tert-butoxycarbonyl)-(O-3-sulfopropyl)-L-tyrosine N-methylamide cesium salt To a solution of the title compound (10.00 g, 34.0 mmol) of Example 1 (3) and 1,3-propanesultone (4.56 g, 37.4 mmol) in DMF (100 mL) was added cesium carbonate (12.18 g, 37.4 mmol) at room temperature, and the mixture was stirred for 15 hr. Diisopropyl ether (300 mL) was added to the reaction solution, and the precipitate was collected by filtration, washed with ethyl acetate and dried to give the title compound (26.42 g, quantitative determination) as a brown solid.

$^1$H-NMR (DMSO-d$_6$) δ 7.90–7.75 (m, 1H), 7.11 (d, J=8.6 Hz, 2H), 6.80 (d, J=8.6 Hz, 2H), 6.90–6.70 (m, 1H), 4.10–3.85 (m, 1H), 3.99 (t, J=6.6 Hz, 2H), 2.84 (dd, J=13.8, 4.8 Hz, 1H), 2.65 (dd, J=13.8, 10.1 Hz, 1H), 2.60–2.45 (m, 2H), 2.57 (d, J=4.5 Hz, 3H), 2.05–1.90 (m, 2H), 1.30 (s, 9H).

(3) O-3-sulfopropyl-L-tyrosine N-methylamide

The title compound (26.42 g, about 34.0 mmol) of Example 4 (2) was suspended in methylene chloride (50 mL)-anisole (18.5 mL, 169.9 mmol) and trifluoroacetic acid (50 mL) was added to the suspension under ice-cooling. The mixture was stirred at the same temperature for 1 hr and at room temperature for 1 hr. Diisopropyl ether (300 mL) was added to the reaction solution, and the precipitate was collected by filtration, washed with ethyl acetate and dried to give a crude product (35.96 g) as a pale-brown solid. This was recrystallized from water (35 mL)-isopropyl alcohol (150 mL) to give the title compound (8.00 g, 74%) as white crystals.

$[\alpha]_D^{25}=+55.4$ (C=1.0, H$_2$O). $^1$H-NMR (DMSO-d$_6$) δ 8.40–7.80 (br, 3H), 8.30 (q, J=4.5 Hz, 1H), 7.12 (d, J=8.6 Hz, 2H), 6.89 (d, J=8.6 Hz, 2H), 4.05 (t, J=6.5 Hz, 2H), 3.83 (dd, J=7.2, 6.6 Hz, 1H), 2.97 (dd, J=13.8, 6.6 Hz, 1H), 2.86 (dd, J=13.8, 7.2 Hz, 1H), 2.61 (d, J=4.5 Hz, 3H), 2.55 (t, J=7.2 Hz, 3H), 2.10–1.90 (m, 2H).

(4) tert-butyl 5-methyl-3(R)-{1(S)-methylcarbamoyl-2-[4-(3-sulfopropoxy)phenyl]ethylcarbamoyl}-2(R or S)-phthalimidomethylhexanoate sodium salt To a solution of the title compound (1.54 g, 3.95 mmol) of Example 4 (1) and the title compound (1.70 g, 3.95 mmol) of Example 4 (3) in DMF (30 mL) were added successively HOBt.H$_2$O (0.61 g, 3.95 mmol), N-methylmorpholine (1.73 mL, 15.7 mmol) and WSCI.HCl (0.91 g, 4.74 mmol) under ice-cooling (internal temperature 10° C.), and the mixture was stirred for 8 hr while gradually raising the temperature to room temperature. The reaction solution was poured into iced water, and sodium dihydrogenphosphate dihydrate (1.85 g, 11.85 mmol) was added. The mixture was saturated with sodium chloride, and extracted (100 mL×3) with a mixed solvent of THF-methanol (10/1). Butanol was added to the extract solution and the mixture was concentrated under reduced pressure. Diisopropyl ether was added to the residue, and the precipitate was collected by filtration and dried to give the title compound (1.62 g, 58%) as a white solid.

$^1$H-NMR (DMSO-d$_6$) δ 8.13 (d, J=8.1 Hz, 1H), 7.95–7.83 (m, 4H), 7.70 (d, J=4.5 Hz, 1H), 7.06 (d, J=8.4 Hz, 2H), 6.78 (d, J=8.4 Hz, 2H), 4.35–4.32 (m, 1H), 3.96 (t, J=6.6 Hz, 2H), 3.82–3.64 (m, 1H), 3.00–2.90 (m, 1H), 2.89–2.73 (m, 1H), 2.70–2.60 (m, 1H), 1.95 (dt, J=14.7, 7.8 Hz, 2H), 1.57 (m, 1H), 1.42–1.28 (m, 1H), 1.13 (s, 9H), 0.86 (d, J=6.0 Hz, 3H), 0.81 (d, J=6.0 Hz, 3H).

(5) 5-methyl-3(R)-{1(S)-methylcarbamoyl-2-[4-(3-sulfopropoxy)phenyl]ethylcarbamoyl}-2(R or S)-phthalimidomethylhexanoic acid The title compound (1.62 g, 2.28 mmol) of Example 4 (4) was suspended in methylene chloride (10 mL), and trifluoroacetic acid (10 mL) was added under ice-cooling (internal temperature 5° C.). The mixture was stirred at room temperature for 3 hr. Ether was added to the reaction solution under ice-cooling, and the precipitate was collected by filtration to give the title compound (1.41 g, quantitative determination) as a white solid.

$^1$H-NMR (DMSO-d$_6$) δ 8.36 (d, J=8.1 Hz, 1H), 7.92–7.83 (m, 4H), 7.72 (d, J=4.2 Hz, 1H), 7.08 (d, J=8.8 Hz, 2H), 6.76

(d, J=8.8 Hz, 2H), 4.39 (dd, J=15.0, 7.8 Hz, 1H), 3.92–3.87 (m, 2H), 2.96–2.67 (m, 4H), 1.85 (dt, J=14.4, 6.9 Hz, 2H), 1.55 (m, 1H), 0.84 (d, J=6.0 Hz, 3H), 0.80 (d, J=6.0 Hz, 3H).

(6) O-(2-nitrobenzyl) 5-methyl-3(R)-{1(S)-methylcarbamoyl-2-[4-(3-sulfopropoxy)phenyl]ethylcarbamoyl}-2(R or S)-phthalimidomethylhexanohydroxamate sodium salt To a solution of the title compound (1.41 g, 2.23 mmol) of Example 4 (5) in DMF (20 mL) were added successively N-methylmorpholine (1.0 mL, 9.80 mmol), O-2-nitrobenzylhydroxylamine hydrochloride (0.55 g, 2.67 mmol), HOBt.H$_2$O (0.34 g, 2.23 mmol) and WSCI.HCl (0.51 g, 2.67 mmol) under ice-cooling (internal temperature 10° C.), and the mixture was stirred for 48 hr while gradually raising the temperature to room temperature. The reaction solution was poured into iced water and sodium dihydrogenphosphate dihydrate (1.04 g, 6.69 mmol) was added. The mixture was saturated with sodium chloride and extracted (100 mL×3) with a mixed solvent of THF-methanol (10/1). Butanol was added to the extract solution and the mixture was concentrated under reduced pressure. Diisopropyl ether was added to the residue and the precipitate was collected by filtration and dried to give the title compound (0.35 g, 19%) as a white solid.

$^1$H-NMR (DMSO-d$_6$) δ 11.39 (s, 1H), 8.14 (d, J=8.1 Hz, 1H), 8.04 (d, J=8.1 Hz, 1H), 7.81–7.76 (m, 5H), 7.64–7.62 (m, 2H), 7.54–7.51 (m, 1H), 7.05 (d, J=8.4 Hz, 2H), 6.74 (d, J=8.4 Hz, 2H), 5.04 (d, J=14.7 Hz, 1H), 5.00 (d, J=14.7 Hz, 1H), 4.33–4.30 (m, 1H), 3.92 (t, J=6.6 Hz, 2H), 3.73–3.62 (m, 1H), 3.52–3.41 (m, 1H), 2.97–2.78 (m, 2H), 1.90 (dt, J=14.4, 7.2 Hz, 2H), 1.52 (m, 1H), 1.28–1.26 (m, 2H), 0.78 (app d, J=2.7 Hz, 6H).

(7) 5-methyl-3(R)-{1(S)-methylcarbamoyl-2-[4-(3-sulfopropoxy)phenyl]ethylcarbamoyl}-2(R or S)-phthalimidomethylhexanohydroxamic acid sodium salt The title compound (350 mg, 0.435 mmol) of Example 4 (6) was suspended in a mixed solvent of THF-water (9/1), and subjected to light radiation with a high pressure mercury vapor lamp under ice-cooling for 1.5 hr. The reaction mixture was concentrated under reduced pressure. The residue was dissolved in methanol and ether was added to allow precipitation. The precipitate was recrystallized (diisopropyl alcohol-water) to give the title compound (93 mg, 32%) as white crystals.

$^1$H-NMR (DMSO-d$_6$) δ 10.58 (s, 1H), 8.75 (s, 1H), 8.12 (d, J=7.8 Hz, 1H), 7.89–7.66 (m, 4H), 7.06 (d, J=8.4 Hz, 2H), 6.74 (d, J=6.3 Hz, 2H), 4.37–4.29 (m, 1H), 3.94 (t, J=6.4 Hz, 2H), 3.75 (dd, J=14.0, 10.3 Hz, 1H), 3.49 (dd, J=13.6, 4.0 Hz, 1H), 2.92 (dd, J=14.0, 6.1 Hz, 1H), 2.84–2.73 (m, 2H), 2.56 (d, J=4.5 Hz, 3H), 2.54–2.42 (m, 2H), 1.90 (dt, J=14.8, 7.1 Hz, 2H), 1.57 (app t, J=9.4 Hz, 1H), 1.23–1.20 (m, 2H), 0.76 (app d, J=4.5 Hz, 6H).

EXAMPLE 5

5-methyl-3(R)-{1(R)-methylcarbamoyl-2-[4-(3-sulfopropoxy)phenyl]ethylcarbamoyl}-2(R or S)-phthalimidomethylhexanohydroxamic acid sodium salt [One Kind of Diastereomer of Compound of Example 1]

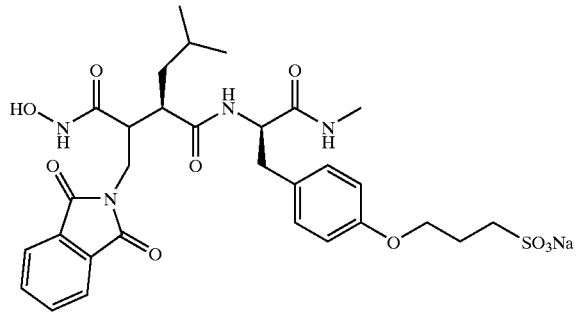

(1) N$^α$-(tert-butoxycarbonyl)-(O-3-sulfopropyl)-D-tyrosine N-methylamide

Using the title compound of Example 3 (1) and in the same manner as in the method described in Example 4 (2), synthesis was performed.

(2) O-3-sulfopropyl-D-tyrosine N-methylamide

Using the title compound of Example 5 (1) and in the same manner as in the method described in Example 4 (3), synthesis was performed.

$[α]_D^{27}$=−55.5 (C=1.0, H$_2$O)

(3) 5-methyl-3(R)-{1(R)-methylcarbamoyl-2-[4-(3-sulfopropoxy)phenyl]ethylcarbamoyl}-2(R or S)-phthalimidomethylhexanohydroxamic acid sodium salt Using the title compound of Example 4 (1) and the title compound of Example 5 (2), and in the same manner as in the method described in Example 4 (4)–(7), synthesis was performed.

$^1$H-NMR (DMSO-d$_6$) δ 10.62 (s, 1H), 9.20 (s, 1H), 8.40 (d, J=8.7 Hz, 1H), 7.88–7.82 (m, 4H), 7.51 (d, J=4.8 Hz, 1H), 7.08 (d, J=8.4 Hz, 2H), 6.77 (d, J=8.4 Hz, 2H), 4.29–4.23 (m, 1H), 3.97 (t, J=6.4 Hz, 2H), 3.76 (dd, J=13.7, 9.0 Hz, 1H), 3.56 (dd, J=13.7, 4.4 Hz, 1H), 3.26–3.13 (m, 1H), 2.63 (d, J=4.4 Hz, 3H), 2.56–2.49 (m, 2H), 2.44–2.32 (m, 1H), 1.96 (dt, J=15.0, 6.4 Hz, 2H), 1.29–1.24 (m, 2H), 0.72 (d, J=5.8 Hz, 3H), 0.57–0.44 (m, 1H), 0.56 (d, J=5.5 Hz, 3H).

EXAMPLE 6

5-methyl-3(S)-{1(R)-methylcarbamoyl-2-[4-(3-sulfopropoxy)phenyl]ethylcarbamoyl}-2(R or S)-phthalimidomethylhexanohydroxamic acid sodium salt [Optical Isomer of Compound of Example 1]

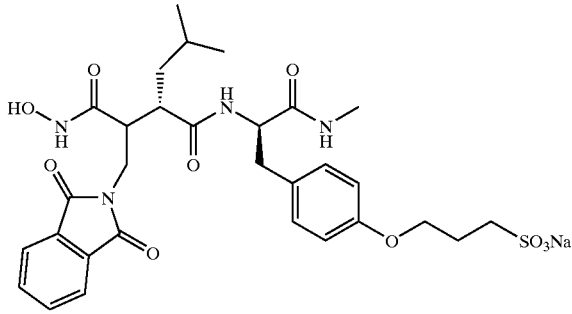

(1) 1,2-dibenzyl 1-tert-butyl 4-methyl-1,1,2-(S)-pentanetricarboxylate

Using (L)-leucine as a starting material and in the same manner as in the method described in Example 1 (1), synthesis was performed.

(2) 4-tert-butoxy-2(S)-isobutyl-3(R or S)-phthalimidomethylsuccinic acid

Using the title compound of Example 6 (1) and in the same manner as in the method described in Example 1 (2), synthesis was performed.

(3) 5-methyl-3(S)-{1(R)-methylcarbamoyl-2-[4-(3-sulfopropoxy)phenyl]ethylcarbamoyl}-2(R or S)-phthalimidomethylhexanohydroxamic acid sodium salt Using the title compound of Example 6 (2) and the title compound of Example 3 (2), and in the same manner as in the method described in Example 1 (5)–(9), synthesis was performed.

$[\alpha]_D^{20} = +46.5$ (c=1.02, MeOH)

The NMR data matched the NMR data of the title compound of Example 1 (9).

EXAMPLE 7

5-methyl-3(S)-{1(S)-methylcarbamoyl-2-[4-(3-sulfopropoxy)phenyl]ethylcarbamoyl}-2(R or S)-phthalimidomethylhexanohydroxamic acid sodium salt [One Kind of Diastereomer of Compound of Example 1]

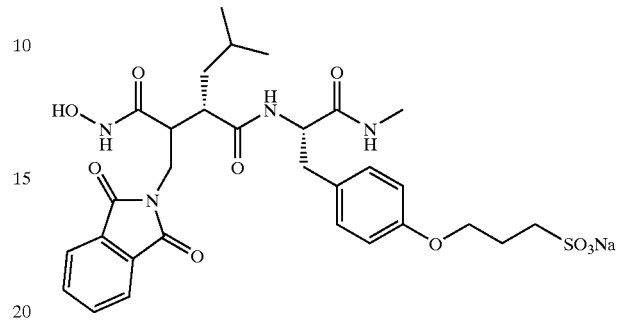

Using the title compound of Example 6 (2) and the title compound of Example 1 (4), and in the same manner as in the method described in Example 1 (5)–(9), synthesis was performed.

The NMR data matched the NMR data of the title compound of Example 3 (3).

EXAMPLE 8

5-methyl-3(S)-{1(R)-methylcarbamoyl-2-[4-(3-sulfopropoxy)phenyl]ethylcarbamoyl}-2(R or S)-phthalimidomethylhexanohydroxamic acid sodium salt [One Kind of Diastereomer of Compound of Example 1]

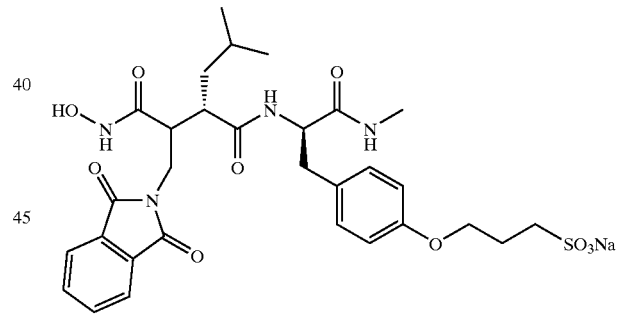

(1) 4-tert-butoxy-2(S)-isobutyl-3(R or S)-phthalimidomethylsuccinic acid [One Kind of Diastereomer of Compound of Example 6 (2)]

The title compound of Example 6 (2) was obtained by purification by column chromatography. The NMR data matched the NMR data of the title compound of Example 4 (1).

(2) 5-methyl-3(S)-{1(R)-methylcarbamoyl-2-[4-(3-sulfopropoxy)phenyl]ethylcarbamoyl}-2(R or S)-phthalimidomethylhexanohydroxamic acid sodium salt Using the title compound of Example 8 (1) and the title compound of Example 5 (2), and in the same manner as in the method described in Example 4 (4)–(7), synthesis was performed.

The NMR data matched the NMR data of the title compound of Example 4 (7).

EXAMPLE 9

5-methyl-3(S)-{1(S)-methylcarbamoyl-2-[4-(3-sulfopropoxy)phenyl]ethylcarbamoyl}-2(R or S)-phthalimidomethylhexanohydroxamic acid sodium salt [One Kind of Diastereomer of Compound of Example 1]

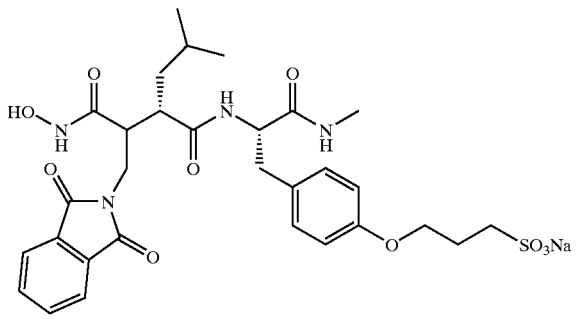

Using the title compound of Example 8 (1) and the title compound of Example 4 (3), and in the same manner as in the method described in Example 4 (4)–(7), synthesis was performed. The NMR data matched the NMR data of the title compound of Example 5 (3).

EXAMPLE 10

5-methyl-3(R)-{1(S)-methylcarbamoyl-2-[4-(2-sulfoethoxy)phenyl]ethylcarbamoyl}-2(R or S)-phthalimidomethylhexanohydroxamic acid sodium salt

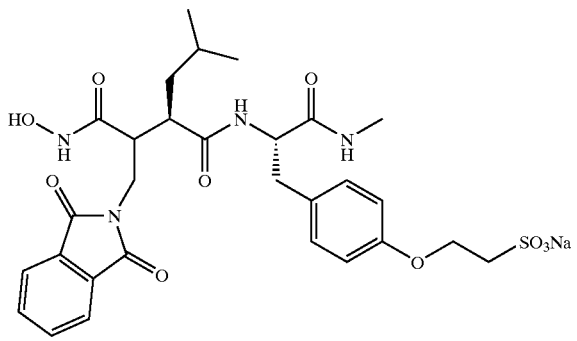

(1) $N^\alpha$-(tert-butoxycarbonyl)-(O-2-benzyloxyethyl)-L-tyrosine N-methylamide To a solution of the title compound (5.00 g, 16.99 mmol) of Example 1 (3) in THF (150 mL) were added successively ethylene glycol monobenzyl ether (7.76 g, 50.96 mmol), triphenylphosphine (13.37 g, 50.96 mmol) and diethyl azodicarboxylate (40% toluene solution) (22.19 g, 50.96 mmol) under ice-cooling. The mixture was stirred at the same temperature for 2 hr, and at room temperature for 68 hr. The reaction solution was concentrated under reduced pressure and purified by flush silica gel column chromatography (silica gel 150 g, hexane/ethyl acetate=5/1, 2/1, 1/1) to give the title compound (7.86 g) as a white solid.

$^1$H-NMR (CDCl$_3$) δ 7.45–7.25 (m, 5H), 7.10 (d, J=8.7 Hz, 2H), 6.85 (d, J=8.7 Hz, 2H), 5.90–5.50 (br, 1H), 5.20–4.85 (br, 1H), 4.63 (s, 2H), 4.30–4.15 (m, 1H), 4.13 (t, J=4.8 Hz, 2H), 3.82 (t, J=4.8 Hz, 2H), 3.03 (dd, J=13.7, 6.2 Hz, 1H), 2.93 (dd, J=13.7, 7.7 Hz, 1H), 2.71 (d, J=4.8 Hz, 3H), 1.41 (s, 9H).

(2) $N^\alpha$-(tert-butoxycarbonyl)-(O-2-hydroxyethyl)-L-tyrosine N-methylamide To a solution of the title compound (7.86 g, about 11.55 mmol) of Example 10 (1) in ethanol (300 mL) was added palladium black (0.80 g) under ice-cooling and under a nitrogen atmosphere. After hydrogen substitution, the mixture was stirred at room temperature for 6 hr. The catalyst was removed from the reaction solution by celite filtration and the residue was concentrated under reduced pressure. The obtained residue was purified by flush silica gel column chromatography (silica gel 200 g, chloroform/methanol=50/1, 20/1, 10/1) to give the title compound (2.48 g, two step yield from Example 10 (1): 43%) as a white solid.

$^1$H-NMR (CDCl$_3$) δ 7.11 (d, J=8.7 Hz, 2H), 6.85 (d, J=8.7 Hz, 2H), 6.00–5.60 (br, 1H), 5.30–4.80 (br, 1H), 4.35–4.20 (m, 1H), 4.06 (t, J=4.4 Hz, 2H), 4.02–3.90 (m, 2H), 3.02 (dd, J=13.4, 6.3 Hz, 1H), 2.95 (dd, J=13.4, 7.5 Hz, 1H), 2.73 (d, J=4.8 Hz, 3H), 2.15 (t, J=6.0 Hz, 1H), 1.41 (s, 9H).

(3) $N^\alpha$-(tert-butoxycarbonyl)-(O-2-bromoethyl)-L-tyrosine N-methylamide

To a solution of the title compound (2.48 g, 7.33 mmol) of Example 10 (2) in methylene chloride (50 mL) were added successively triphenylphosphine (2.88 g, 10.99 mmol) and carbon tetrabromide (2.92 g, 8.79 mmol) at room temperature. The mixture was stirred at the same temperature for 15 min. Saturated aqueous sodium hydrogencarbonate solution (50 mL) was added to the reaction solution, and the mixture was extracted with chloroform (100 mL). The obtained organic layer was washed with water (50 mL), dried over anhydrous magnesium sulfate and concentrated under reduced pressure. The obtained residue was purified by flush silica gel column chromatography (silica gel 100 g, chloroform/methanol=50/1, 20/1) to give the title compound (4.11 g) as a white solid.

$^1$H-NMR (CDCl$_3$) δ 7.11 (d, J=8.6 Hz, 2H), 6.84 (d, J=8.6 Hz, 2H), 6.10–5.60 (br, 1H), 5.30–4.80 (br, 1H), 4.30–4.15 (m, 1H), 4.26 (t, J=6.3 Hz, 2H), 3.63 (t, J=6.3 Hz, 2H), 3.10–2.90 (m, 2H), 2.73 (d, J=5.1 Hz, 3H), 1.41 (s, 9H).

(4) $N^\alpha$-(tert-butoxycarbonyl)-(O-2-sulfoethyl)-L-tyrosine N-methylamide sodium salt The title compound (4.11 g, about 6.11 mmol) of Example 10 (3) was suspended in a solution of ethanol (100 mL)-water (50 mL) and heated at 80° C. for dissolution. A solution of sodium sulfite (0.85 g, 6.72 mmol) in water (50 mL) was added and the mixture was stirred under reflux for 22 hr. The reaction solution was cooled and ethanol was distilled away under reduced pressure. The residue was washed with ethyl acetate (100 mL). Butanol was added to the obtained aqueous layer and the mixture was concentrated under reduced pressure to give the title compound (1.65 g, two step yield from Example 10 (3): 56%) as a yellow solid.

$^1$H-NMR (DMSO-d$_6$) δ 7.90–7.75 (m, 1H), 7.13 (d, J=8.4 Hz, 2H), 6.80 (d, J=8.4 Hz, 2H), 6.95–6.80 (m, 1H), 4.16 (t, J=7.7 Hz, 2H), 4.10–3.90 (m, 1H), 2.88 (t, J=7.7 Hz, 2H), 2.95–2.75 (m, 1H), 2.75–2.60 (m, 1H), 2.57 (d, J=4.5 Hz, 3H), 1.30 (s, 9H).

(5) O-2-sulfoethyl-L-tyrosine N-methylamide

A solution of the title compound (1.65 g, about 4.10 mmol) of Example 10 (4) in trifluoroacetic acid (20 mL) was stirred at room temperature for 1 hr. Toluene was added to the reaction solution and the mixture was concentrated under reduced pressure to give the title compound (2.54 g, quantitative determination).

$^1$H-NMR (DMSO-d$_6$) δ 8.40–8.25 (m, 1H), 8.35–7.90 (br, 3H), 7.13 (d, J=8.4 Hz, 2H), 6.89 (d, J=8.4 Hz, 2H), 4.20 (t, J=7.6 Hz, 2H), 4.00–3.70 (m, 1H), 3.10–2.80 (m, 2H), 2.90 (t, J=7.6 Hz, 2H), 2.61 (d, J=4.8 Hz, 3H).

(6) tert-butyl 5-methyl-3(R)-{1(S)-methylcarbamoyl-2-[4-(2-sulfoethoxy)phenyl]ethylcarbamoyl}-2(R or S)-phthalimidomethylhexanoate sodium salt To a solution of the title compound (1.60 g, 4.10 mmol) of Example 1 (2) and the title compound (2.54 g, about 4.10 mmol) of Example 10 (5) in DMF (20 mL) were added successively HOBt.H$_2$O (0.63 g, 4.10 mmol), N-methylmorpholine (1.80 mL, 16.40 mmol) and WSCI.HCl (0.94 g, 4.92 mmol) under ice-cooling, and the mixture was stirred for 24.5 hr while gradually raising the temperature to room temperature. The reaction solution was poured into a solution of sodium dihydrogenphosphate dihydrate (3.20 g, 20.50 mmol) dissolved in water (100 mL) and washed with ethyl acetate (100 mL). The obtained aqueous layer was saturated with sodium chloride and extracted (100 mL×3) with a solution of THF-methanol (10/1). Butanol was added to the extract solution and the mixture was concentrated under reduced pressure. Methanol was added to the obtained residue and an insoluble material was removed by filtration. The filtrate was concentrated under reduced pressure to give the title compound (2.61 g, 91%) as a yellow solid.

$^1$H-NMR (DMSO-d$_6$) δ 8.45 (d, J=8.9 Hz, 1H), 8.00–7.80 (m, 5H), 7.19 (d, J=8.6 Hz, 2H), 6.57 (d, J=8.6 Hz, 2H), 4.75–4.60 (m, 1H), 3.80–3.60 (m, 2H), 3.30–3.15 (m, 1H), 3.00–2.90 (m, 1H), 2.80–2.40 (m, 3H), 2.62 (d, J=4.5 Hz, 3H), 2.35–2.15 (m, 2H), 2.00–1.85 (m, 1H), 1.60–1.20 (m, 2H), 1.09 (s, 9H), 0.90–0.75 (m, 1H), 0.85 (d, J=6.4 Hz, 3H), 0.76 (d, J=6.4 Hz, 3H).

(7) 5-methyl-3(R)-{1(S)-methylcarbamoyl-2-[4-(2-sulfoethoxy)phenyl]ethylcarbamoyl}-2(R or S)-phthalimidomethylhexanoic acid The title compound (2.61 g, 3.75 mmol) of Example 10 (6) was suspended in trifluoroacetic acid (20 mL) and the mixture was stirred at room temperature for 4 hr. Diethyl ether (100 mL) was added to the reaction solution, and the precipitate was collected by filtration to give the title compound (2.20 g, 95%) as a white solid.

$^1$H-NMR (DMSO-d$_6$) δ 13.00–11.60 (br, 1H), 8.41 (d, J=8.7 Hz, 1H), 8.00–7.75 (m, 5H), 7.18 (d, J=8.6 Hz, 2H), 6.56 (d, J=8.6 Hz, 2H), 4.75–4.60 (m, 1H), 3.78–3.60 (m, 2H), 3.22 (dd, J=13.6, 11.3 Hz, 1H), 2.94 (dd, J=13.8, 4.0 Hz, 1H), 2.75–2.60 (m, 1H), 2.62 (d, J=4.4 Hz, 3H), 2.60–2.42 (m, 2H), 2.30–2.15 (m, 2H), 2.02 (dd, J=13.6, 4.1 Hz, 1H), 1.60–1.40 (m, 1H), 1.40–1.20 (m, 1H), 0.90–0.70 (m, 1H), 0.84 (d, J=6.5 Hz, 3H), 0.76 (d, J=6.5 Hz, 3H).

(8) 2-tetrahydropyranyl 5-methyl-3(R)-{1(S)-methylcarbamoyl-2-[4-(2-sulfoethoxy)phenyl]ethylcarbamoyl}-2(R or S)-phthalimidomethylhexanohydroxamate sodium salt To a solution of the title compound (2.20 g, 3.56 mmol) of Example 10 (7) in DMF (50 mL) were added successively N-methylmorpholine (0.78 mL, 7.12 mmol), O-2-tetrahydropyranylhydroxylamine (0.50 g, 4.27 mmol), HOBt.H$_2$O (0.55 g, 3.56 mmol) and WSCI.HCl (0.82 g, 4.27 mmol) under ice-cooling, and the mixture was stirred for 16 hr while gradually raising the temperature to room temperature. The reaction solution was poured into a solution of sodium dihydrogenphosphate dihydrate (2.78 g, 17.81 mmol) in water (200 mL), saturated with sodium chloride, and extracted (200 mL×1, 100 mL×3) with a mixed solvent of THF-methanol (10/1). Butanol was added to the extract solution and the mixture was concentrated under reduced pressure. Diethyl ether was added to the residue, and the precipitate was collected by filtration and dried to give the title compound (4.50 g, quantitative determination) as a white solid.

$^1$H-NMR (DMSO-d$_6$) δ 10.89 and 10.84 (br s, 1H), 8.37 (d, J=9.0 Hz, 1H), 8.00–7.87 (m, 1H), 7.87–7.75 (m, 4H), 7.19 (d, J=8.3 Hz, 2H), 6.52 (d, J=8.3 Hz, 2H), 4.70–4.58 (m, 1H), 4.53 and 4.37 (br s, 1H), 3.75–3.25 (m, 3H), 3.25–3.12 (m, 1H), 3.12–2.88 and 2.75–2.60 (m, 3H), 2.61 (d, J=4.5 Hz, 3H), 2.60–2.10 (m, 4H), 1.90–1.75 (m, 1H), 1.60–1.20 (m, 8H), 0.90–0.70 (m, 1H), 0.82 (d, J=6.5 Hz, 3H), 0.75 (d, J=6.5 Hz, 3H).

(9) 5-methyl-3(R)-{1(S)-methylcarbamoyl-2-[4-(2-sulfoethoxy)phenyl]ethylcarbamoyl}-2(R or S)-phthalimidomethylhexanohydroxamic acid sodium salt The title compound (4.50 g, about 3.56 mmol) of Example 10 (8) was suspended in a solution of water (20 mL)-methanol (40 mL)-THF (40 mL) and 1N hydrochloric acid (20 mL) was added. The mixture was stirred for 15 hr at room temperature and methanol and THF were distilled away under reduced pressure from the reaction solution. Water (300 mL) and 1N aqueous sodium hydrogencarbonate solution (20 mL) were added to the residue for neutralization. The obtained solution was purified by reverse phase column chromatography (Fuji Silysia Chemical Chromatorex ODS DM-1020T: 70 g, water/methanol=100/0, 10/1, 5/1), butanol was added to the eluate and the mixture was concentrated under reduced pressure. The residue was recrystallized from water-isopropanol to give the title compound (0.73 g, 31%) as white crystals.

$^1$H-NMR (DMSO-d$_6$) δ 10.27 (br s, 1H), 8.57 (br s, 1H), 8.28 (d, J=8.7 Hz, 1H), 7.95–7.75 (m, 5H), 7.18 (d, J=8.6 Hz, 2H), 6.52 (d, J=8.6 Hz, 2H), 4.75–4.55 (m, 1H), 3.75–3.54 (m, 2H), 3.28 (dd, J=13.5, 11.3 Hz, 1H), 2.92 (dd, J=13.6, 3.9 Hz, 1H), 2.72–2.55 (m, 1H), 2.61 (d, J=4.5 Hz, 3H), 2.50–2.28 (m, 2H), 2.28–2.10 (m, 2H), 1.84 (dd, J=13.5, 3.9 Hz, 1H), 1.50–1.20 (m, 2H), 0.90–0.70 (m, 1H), 0.82 (d, J=6.5 Hz, 3H), 0.76 (d, J=6.5 Hz, 3H).

EXAMPLE 11

5-methyl-3(R)-{1(S)-methylcarbamoyl-2-[4-(4-sulfobutoxy)phenyl]ethylcarbamoyl}-2(R or S)-phthalimidomethylhexanohydroxamic acid sodium salt

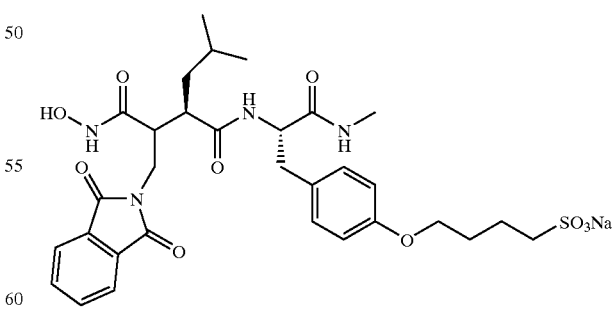

(1) N$^α$-(tert-butoxycarbonyl)-(O-4-sulfobutyl)-L-tyrosine N-methylamide cesium salt Using the title compound of Example 1 (3) and 1,4-butanesultone, and in the same manner as in the method described in Example 4 (2), synthesis was performed.

(2) O-4-sulfobutyl-L-tyrosine N-methylamide

Using the title compound of Example 11 (1), and in the same manner as in the method described in Example 4 (3), synthesis was performed.

$^{1}$H-NMR (DMSO-$d_6$) δ 8.40–8.25 (m, 1H), 8.40–7.90 (br, 3H), 7.11 (d, J=8.6 Hz, 2H), 6.89 (d, J=8.6 Hz, 2H), 4.10–3.70 (m, 3H), 3.05–2.78 (m, 2H), 2.61 (d, J=4.6 Hz, 3H), 2.55–2.35 (m, 2H), 1.90–1.50 (m, 4H).

(3) 5-methyl-3(R)-{1(S)-methylcarbamoyl-2-[4-(4-sulfobutoxy)phenyl]ethylcarbamoyl}-2(R or S)-phthalimidomethylhexanohydroxamic acid sodium salt Using the title compound of Example 1 (2) and the title compound of Example 11 (2), and in the same manner as in the method described in Example 10 (6)–(9), synthesis was performed.

$^{1}$H-NMR (DMSO-$d_6$) δ 10.27 (br s, 1H), 8.56 (br s, 1H), 8.28 (d, J=9.0 Hz, 1H), 7.95–7.75 (m, 5H), 7.18 (d, J=8.6 Hz, 2H), 6.54 (d, J=8.6 Hz, 2H), 4.70–4.55 (m, 1H), 3.45–3.15 (m, 3H), 2.92 (dd, J=13.4, 3.2 Hz, 1H), 2.72–2.55 (m, 1H), 2.62 (d, J=4.6 Hz, 3H), 2.50–2.38 (m, 1H), 2.38–2.25 (m, 1H), 2.21 (t, J=7.8 Hz, 2H), 1.81 (dd, J=13.5, 3.8 Hz, 1H), 1.50–1.20 (m, 4H), 1.10–0.85 (m, 2H), 0.85–0.70 (m, 1H), 0.83 (d, J=6.5 Hz, 3H), 0.75 (d, J=6.5 Hz, 3H).

EXAMPLE 12

5-methyl-3(R)-{1(S)-methylcarbamoyl-2-[4-(5-sulfopentoxy)phenyl]ethylcarbamoyl}-2(R or S)-phthalimidomethylhexanohydroxamic acid sodium salt

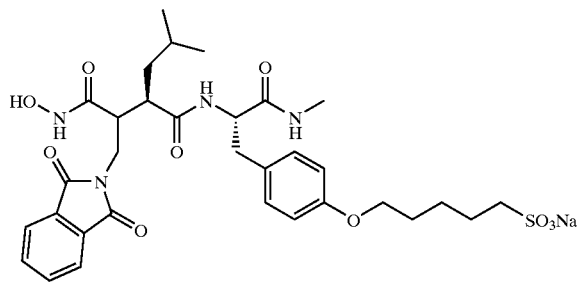

(1) N$^\alpha$-(tert-butoxycarbonyl)-(O-5-chloropentyl)-L-tyrosine N-methylamide A solution of the title compound (10.00 g, 34.0 mmol) of Example 1 (3), 1-bromo-5-chloropentane (5.0 mL, 38.0 mmol), $K_2CO_3$ (2.36 g, 17.1 mmol) in DMF (100 mL) was stirred at 70° C. for 22 hr. After allowing to cool, the solvent was distilled away under reduced pressure and water was added. The mixture was extracted with ethyl acetate, washed with saturated brine, and dried over magnesium sulfate. The solvent was distilled away and the residue was purified by silica gel column chromatography ($CHCl_3$) to give the title compound (7.56 g, 56%).

$^{1}$H-NMR (DMSO-$d_6$) δ 7.99–7.74 (m, 1H), 7.12 (d, J=8.4 Hz, 2H), 6.83 (m, 1H), 6.81 (d, J=8.4 Hz, 2H), 4.11–3.99 (m, 1H), 3.92 (t, J=6.3 Hz, 2H), 3.65 (t, J=6.6 Hz, 2H), 2.89–2.75 (m, 1H), 2.74–2.45 (m, 1H), 2.59 (m, 3H), 1.90–1.43 (m, 6H), 1.35–1.15 (m, 9H).

(2) N$^\alpha$-(tert-butoxycarbonyl)-(O-5-sulfopentyl)-L-tyrosine N-methylamide sodium salt Using the title compound of Example 12 (1), and in the same manner as in the method described in Example 10 (4), synthesis was performed.

$^{1}$H-NMR (DMSO-$d_6$) δ 7.95–7.75 (br, 1H), 7.11 (d, J=8.4 Hz, 2H), 6.87–6.83 (m, 1H), 6.81 (d, J=8.4 Hz, 2H), 4.50–4.21 (br, 1H), 4.10–3.98 (m, 1H), 3.98–3.77 (m, 2H), 2.92–2.78 (m, 1H), 2.70–2.45 (m, 1H), 2.59 (m, 3H), 2.44–2.30 (m, 2H), 1.79–1.36 (m, 6H), 1.35–1.15 (m, 8H).

(3) O-5-sulfopentyl-L-tyrosine N-methylamide

Using the title compound of Example 12 (2), and in the same manner as in the method described in Example 10 (5), synthesis was performed.

$^{1}$H-NMR (DMSO-$d_6$) δ 8.35–8.24 (br, 1H), 8.22–8.01 (br, 2H), 7.11 (d, J=8.4 Hz, 2H), 6.90 (d, J=8.4 Hz, 2H), 3.93 (t, J=6.3 Hz, 2H), 3.90–3.74 (m, 1H), 3.66–3.52 (m, 1H), 3.50–3.30 (m, 2H), 3.07–2.79 (m, 1H), 2.62 (d, J=4.5 Hz, 2H), 2.45–2.32 (m, 1H), 1.80–1.39 (m, 7H).

(4) 5-methyl-3(R)-{1(S)-methylcarbamoyl-2-[4-(5-sulfopentoxy)phenyl]ethylcarbamoyl}-2(R or S)-phthalimidomethylhexanohydroxamic acid sodium salt Using the title compound of Example 1 (2) and the title compound of Example 12 (3), and in the same manner as in the method described in Example 10 (6)–(9), synthesis was performed.

$^{1}$H-NMR (DMSO-$d_6$) δ 10.27 (br, 1H), 8.56 (br, 1H), 8.28 (d, J=9.0 Hz, 1H), 7.88–7.80 (br, 5H), 7.19 (d, J=8.7 Hz, 2H), 6.53 (d, J=8.7 Hz, 2H), 4.67–4.57 (m, 1H), 3.40–3.18 (m, 4H), 2.98–2.81 (m, 1H), 2.70–2.51 (m, 4H), 2.49–2.37 (m, 1H), 2.36–2.21 (m, 2H), 1.85–1.71 (m, 1H), 1.48–1.20 (m, 4H), 1.08–0.82 (m, 5H), 0.82 (d, J=6.3 Hz, 3H), 0.75 (d, J=6.3 Hz, 3H).

EXAMPLE 13

5-methyl-3(R)-{1(S)-methylcarbamoyl-2-[4-(3-sulfopropoxy)phenyl]ethylcarbamoyl}-2(R or S)-(2-naphthylmethyl)hexanohydroxamic acid sodium salt

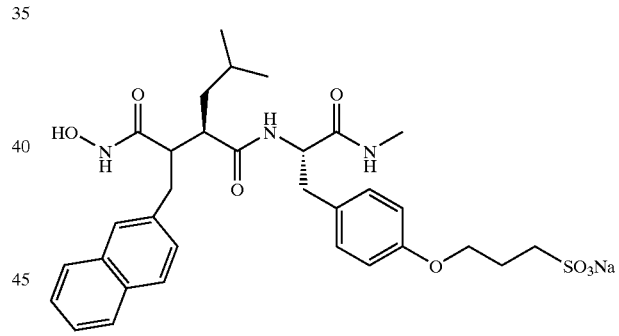

(1) 4-tert-butoxy-2(R)-isobutyl-3(R or S)-(2-naphthyl)methylsuccinic acid

Using the title compound of Example 1 (1) and 2-naphthyl bromide, and in the same manner as in the method described in Example 1 (2), synthesis was performed. For purification, flush column chromatography and recrystallization (hexane) were conducted.

$^{1}$H-NMR ($CDCl_3$) δ 7.80–7.73 (m, 3H), 7.61 (s, 1H), 7.47–7.39 (m, 2H), 7.28 (d, J=1.8 Hz, 1H), 3.07–2.95 (m, 3H), 2.82 (m, 1H), 1.82–1.72 (m, 2H), 1.65–1.62 (m, 1H), 1.22 (s, 9H), 0.93 (d, J=6.3 Hz, 3H), 0.91 (d, J=6.3 Hz, 3H).

(2) 5-methyl-3(R)-{1(S)-methylcarbamoyl-2-[4-(3-sulfopropoxy)phenyl]ethylcarbamoyl}-2(R or S)-(2-naphthylmethyl)hexanohydroxamic acid sodium salt Using the title compound of Example 13 (1) and the title compound of Example 4 (3), and in the same manner as in the method described in Example 10 (6)–(9), synthesis was performed.

¹H-NMR (DMSO-d₆) δ 10.13 (br s, 1H), 8.56 (br s, 1H), 8.31 (d, J=8.7 Hz, 1H), 7.90–7.65 (m, 4H), 7.50–7.35 (m, 2H), 7.26 (s, 1H), 7.20 (d, J=8.6 Hz, 2H), 6.94 (dd, J=8.4, 1.5 Hz, 1H), 6.59 (d, J=8.6 Hz, 2H), 4.70–4.55 (m, 1H), 3.50–3.20 (m, 3H), 2.90 (dd, J=13.6, 3.9 Hz, 1H), 2.72 (dd, J=13.6, 11.5 Hz, 1H), 2.61 (d, J=4.5 Hz, 3H), 2.58–2.40 (m, 1H), 2.30–2.20 (m, 1H), 2.20 (t, J=7.3 Hz, 2H), 1.94–1.80 (m, 1H), 1.60–1.20 (m, 4H), 1.00–0.80 (m, 1H), 0.85 (d, J=6.5 Hz, 3H), 0.77 (d, J=6.5 Hz, 3H).

EXAMPLE 14

5-methyl-3(R)-{1(S)-phenylcarbamoyl-2-[4-(3-sulfopropoxy)phenyl]ethylcarbamoyl}-2(R or S)-phthalimidomethylhexanohydroxamic acid sodium salt

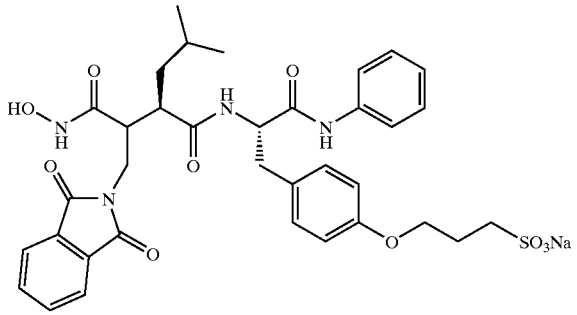

(1) Nα-(tert-butoxycarbonyl)-(O-tert-butyl)-L-tyrosine N-phenylamide

Using N-(tert-butoxycarbonyl)-(O-tert-butyl)-L-tyrosine and aniline, and in the same manner as in the method described in Example 1 (3), synthesis was performed.

¹H-NMR (DMSO-d₆) δ 9.96 (br s, 1H), 7.56 (d, J=7.5 Hz, 2H), 7.30 (t, J=8.0 Hz, 2H), 7.21 (d, J=8.3 Hz, 2H), 7.09 (d, J=8.1 Hz, 1H), 7.04 (t, J=7.4 Hz, 1H), 6.86 (d, J=8.3 Hz, 2H), 4.40–4.12 (m, 1H), 2.93 (dd, J=13.4, 4.8 Hz, 1H), 2.80 (dd, J=13.4, 10.1 Hz, 1H), 1.32 (s, 9H), 1.24 (s, 9H).

(2) L-tyrosine N-phenylamide hydrochloride

Using the title compound of Example 14 (1) and in the same manner as in the method described in Example 1 (4), synthesis was performed.

¹H-NMR (DMSO-d₆) δ 10.71 (br s, 1H), 9.37 (br s, 1H), 8.60–8.10 (br, 3H), 7.57 (d, J=7.5 Hz, 2H), 7.34 (t, J=8.0 Hz, 2H), 7.10 (t, J=7.5 Hz, 1H), 7.09 (d, J=8.4 Hz, 2H), 6.69 (d, J=8.4 Hz, 2H), 4.30–4.05 (m, 1H), 3.09 (dd, J=13.8, 6.6 Hz, 1H), 2.99 (dd, J=13.8, 7.2 Hz, 1H).

(3) 5-methyl-3(R)-{1(S)-phenylcarbamoyl-2-[4-(3-sulfopropoxy)phenyl]ethylcarbamoyl}-2(R or S)-phthalimidomethylhexanohydroxamic acid sodium salt Using the title compound of Example 1 (2) and the title compound of Example 14 (2), and in the same manner as in the method described in Example 1 (5)–(9), synthesis was performed.

¹H-NMR (DMSO-d₆) δ 10.27 (br s, 1H), 10.11 (br s, 1H), 8.80–8.30 (br, 1H), 8.43 (d, J=8.4 Hz, 1H), 7.90–7.80 (m, 4H), 7.61 (d, J=7.5 Hz, 2H), 7.33 (t, J=7.8 Hz, 2H), 7.26 (d, J=8.7 Hz, 2H), 7.06 (t, J=7.4 Hz, 1H), 6.56 (d, J=8.7 Hz, 2H), 4.90–4.80 (m, 1H), 3.50–3.20 (m, 3H), 3.04 (dd, J=13.2, 3.6 Hz, 1H), 2.82–2.68 (m, 1H), 2.60–2.45 (m, 1H), 2.42–2.29 (m, 1H), 2.16 (t, J=7.4 Hz, 2H), 1.95 (dd, J=13.6, 3.9 Hz, 1H), 1.55–1.20 (m, 4H), 0.90–0.75 (m, 1H), 0.84 (d, J=6.6 Hz, 3H), 0.73 (d, J=6.6 Hz, 3H).

EXAMPLE 15

5-methyl-3(R)-[2-phenyl-1(S)-(sulfomethylcarbamoyl)ethylcarbamoyl]-2(R or S)-phthalimidomethylhexanohydroxamic acid sodium salt

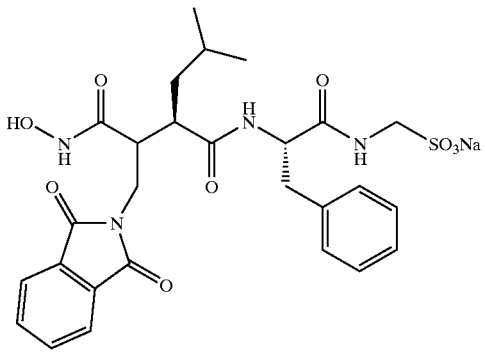

(1) N-(tert-butoxycarbonyl)-L-phenylalanine benzyl ester

To a solution of N-(tert-butoxycarbonyl)-L-phenylalanine (30.0 g, 113 mmol) and benzyl alcohol (14.0 mL, 136 mmol) in methylene chloride (200 mL), were added successively 4-dimethylaminopyridine (1.38 g, 11.3 mmol) and WSCI·HCl (26.0 g, 136 mmol) under ice-cooling, and the mixture was stirred for 63 hr while gradually raising the temperature to room temperature. The solvent was distilled away from the reaction solution under reduced pressure, and water (200 mL) was added to the residue. The mixture was extracted with ethyl acetate (400 mL). The obtained extract solution was washed with 0.5N hydrochloric acid, water, saturated aqueous sodium hydrogencarbonate solution, water and saturated brine (each 200 mL), and dried (anhydrous magnesium sulfate) and concentrated under reduced pressure. The obtained residue was recrystallized from hexane to give the title compound (33.1 g, 82%) as white crystals.

¹H-NMR (CDCl₃) δ 7.45–6.90 (m, 10H), 5.17 (d, J=12.3 Hz, 1H), 5.10 (d, J=12.3 Hz, 1H), 5.05–4.85 (m, 1H), 4.75–4.55 (m, 1H), 3.20–2.85 (m, 2H), 1.41 (s, 9H).

(2) L-phenylalanine benzyl ester hydrochloride

To a solution of the title compound (17.8 g, 50.1 mmol) of Example 15 (1) in chloroform (60 mL) was added 4N hydrochloric acid-dioxane solution (40 mL) under ice-cooling, and the mixture was stirred at room temperature for 4 hr. Diethyl ether (100 mL) was added to the reaction solution, and the precipitate was collected by filtration, washed with diethyl ether and dried to give the title compound (13.7 g, 94%) as a white solid.

¹H-NMR (DMSO-d₆) δ 8.75 (br s, 3H), 7.45–7.15 (m, 10H), 5.16 (d, J=12.4 Hz, 1H), 5.11 (d, J=12.4 Hz, 1H), 4.32 (dd, J=7.8, 5.6 Hz, 1H), 3.23 (dd, J=14.0, 5.6 Hz, 1H), 3.09 (dd, J=14.0, 7.8 Hz, 1H).

(3) tert-butyl 3(R)-[1(S)-benzyloxycarbonyl-2-phenylethylcarbamoyl]-5-methyl-2(R or S)-phthalimidomethylhexanoate To a solution of the title compound (10.0 g, 25.7 mmol) of Example 1 (2) and the title compound (7.49 g, 25.7 mmol) of Example 15 (2) in DMF (50 mL) were added successively N-methylmorpholine (8.5 mL, 77.0 mmol), HOBt.H₂O (3.93 g, 25.7 mmol) and WSCI.HCl (5.91 g, 30.8 mmol) under ice-cooling, and the mixture was stirred for 14 hr while gradually raising the temperature to room temperature. The reaction solution was poured into iced water (200 mL) and the precipitate was collected by filtration. The obtained precipitate was dissolved in ethyl acetate (300 mL) and washed successively with 0.5N hydrochloric acid, water, saturated aqueous sodium hydrogencarbonate solution, water and saturated brine (each 100 mL). It was dried (anhydrous magnesium sulfate) and concentrated under reduced pressure. The obtained residue was recrystallized from ethyl acetate-hexane to give the title compound (12.3 g, 76%) as white crystals.

$^1$H-NMR (CDCl$_3$) δ 7.90–7.80 (m, 2H), 7.80–7.68 (m, 2H), 7.40–7.05 (m, 10H), 6.70 (d, J=8.2 Hz, 1H), 5.19 (d, J=12.2 Hz, 1H), 5.13 (d, J=12.2 Hz, 1H), 5.04 (ddd, J=8.6, 8.2, 5.5 Hz, 1H), 3.46 (dd, J=14.2, 5.4 Hz, 1H), 3.39 (dd, J=14.2, 7.1 Hz, 1H), 3.30 (dd, J=14.1, 5.5 Hz, 1H), 3.06 (dd, J=14.1, 8.6 Hz, 1H), 2.86 (ddd, J=9.7, 7.1, 5.4 Hz, 1H), 2.60 (ddd, J=10.8, 9.8, 3.4 Hz, 1H), 1.70–1.55 (m, 1H), 1.55–1.35 (m, 1H), 1.25 (s, 9H), 1.10–0.95 (m, 1H), 0.79 (d, J=6.4 Hz, 3H), 0.78 (d, J=6.4 Hz, 3H).

(4) 3(R)-[1(S)-benzyloxycarbonyl-2-phenylethylcarbamoyl]-5-methyl-2(R or S)-phthalimidomethylhexanoic acid To a solution of the title compound (12.0 g, 19.1 mmol) of Example 15 (3) in methylene chloride (10 mL) was added trifluoroacetic acid (20 mL) under ice-cooling, and the mixture was stirred at room temperature for 6 hr. The solvent was distilled away under reduced pressure from the reaction solution, and precipitation with diethyl ether-hexane was conducted to give the title compound (10.9 g, quantitative determination) as a white powder.

$^1$H-NMR (DMSO-d$_6$) δ 12.35 (br s, 1H), 8.66 (d, J=8.4 Hz, 1H), 7.95–7.80 (m, 4H), 7.45–7.20 (m, 7H), 7.20–7.05 (m, 2H), 6.95–6.80 (m, 1H), 5.14 (d, J=12.5 Hz, 1H), 5.09 (d, J=12.5 Hz, 1H), 4.85–4.70 (m, 1H), 3.45–3.30 (m, 1H), 3.19 (dd, J=13.7, 4.8 Hz, 1H), 2.89 (dd, J=13.7, 11.0 Hz, 1H), 2.65 (ddd, J=10.8, 5.1, 5.1 Hz, 1H), 2.59–2.38 (m, 2H), 1.60–1.40 (m, 1H), 1.40–1.20 (m, 1H), 0.90–0.75 (m, 1H), 0.74 (d, J=6.6 Hz, 3H), 0.69 (d, J=6.6 Hz, 3H).

(5) 2-tetrahydropyranyl 3(R)-[1(S)-benzyloxycarbonyl-2-phenylethylcarbamoyl]-5-methyl-2(R or S)-phthalimidomethylhexanohydroxamate To a solution of the title compound (10.90 g, 19.1 mmol) of Example 15 (4) in DMF (50 mL) were added successively N-methylmorpholine (2.1 mL, 19.1 mmol), 2-tetrahydropyranylhydroxylamine (2.69 g, 23.0 mmol), HOBt.H₂O (2.93 g, 19.1 mmol) and WSCI.HCl (4.40 g, 23.0 mmol) under ice-cooling, and the mixture was stirred for 14 hr while gradually raising the temperature to room temperature. The reaction solution was poured into iced water (200 mL), and the precipitate was collected by filtration. The obtained precipitate was washed with water and diethyl ether, and dried to give the title compound (11.97 g, 93%) as a white solid.

$^1$H-NMR (DMSO-d$_6$) δ 10.93 and 10.88 (br s, 1H), 8.70–8.55 (m, 1H), 7.95–7.75 (m, 4H), 7.40–7.20 (m, 7H), 7.15–7.00 (m, 2H), 6.90–6.75 (m, 1H), 5.13 (d, J=12.6 Hz, 1H), 5.09 (d, J=12.6 Hz, 1H), 4.85–4.70 (m, 1H), 4.53 and 4.37 (br s, 1H), 3.75–3.27 (m, 2H), 3.19 (dd, J=13.8, 4.8 Hz, 1H), 3.10–2.65 (m, 1H), 2.88 (dd, J=13.8, 11.1 Hz, 1H), 2.60–2.35 (m, 2H), 2.24 (ddd, J=13.9, 13.7, 4.1 Hz, 1H), 1.65–1.20 (m, 8H), 0.90–0.75 (m, 1H), 0.72 (d, J=6.3 Hz, 3H), 0.68 (d, J=6.3 Hz, 3H).

(6) 2-tetrahydropyranyl 3(R)-[1(S)-carboxy-2-phenylethylcarbamoyl]-5-methyl-2(R or S)-phthalimidomethylhexanohydroxamate The title compound (11.97 g, 17.9 mmol) of Example 15 (5) was dissolved in a mixed solvent of methanol (100 mL)-DMF (150 mL) and 10% palladium-carbon catalyst (1.20 g) was added under ice-cooling. After hydrogen substitution, the mixture was stirred at room temperature for 3.5 hr. The catalyst was removed from the reaction solution by celite filtration. The filtrate was concentrated under reduced pressure and water was added to the obtained residue. The precipitate was collected by filtration, washed with water and dried to give the title compound (9.17 g, 89%) as a white solid.

$^1$H-NMR (DMSO-d$_6$) δ 13.50–11.50 (br, 1H), 10.93 and 10.88 (br s, 1H), 8.60–8.35 (m, 1H), 7.95–7.75 (m, 4H), 7.40–7.20 (m, 2H), 7.15–7.00 (m, 2H), 6.87–6.70 (m, 1H), 4.70–4.57 (m, 1H), 4.53 and 4.37 (br s, 1H), 3.75–3.20 (m, 2H), 3.15 (dd, J=13.7, 4.2 Hz, 1H), 3.10–2.65 (m, 1H), 2.81 (dd, J=13.7, 11.5 Hz, 1H), 2.60–2.35 (m, 2H), 2.21 (ddd, J=13.9, 13.7, 4.1 Hz, 1H), 1.70–1.10 (m, 8H), 0.95–0.70 (m, 1H), 0.82 (d, J=6.3 Hz, 3H), 0.76 (d, J=6.3 Hz, 3H).

(7) 2-tetrahydropyranyl 5-methyl-3(R)-[2-phenyl-1(S)-(sulfomethylcarbamoyl)ethylcarbamoyl]-2(R or S)-phthalimidomethylhexanohydroxamate sodium salt To a solution of the title compound (5.79 g, 9.99 mmol) of Example 15 (6) in DMF (100 mL) were added successively aminomethanesulfonic acid (1.33 g, 12.0 mmol), 3-hydroxy-3,4-dihydro-4-oxo-1,2,3-benzotriazine (1.63 g, 9.99 mmol, hereinafter to be abbreviated as HOOBt), N-methylmorpholine (1.1 mL, 9.99 mmol) and WSCI.HCl (2.30 g, 12.0 mmol) under ice-cooling. The mixture was stirred for 14 hr while gradually raising the temperature to room temperature. The reaction solution was poured into a solution of sodium dihydrogenphosphate dihydrate (7.79 g, 49.9 mmol) in water (400 mL), saturated with sodium chloride, and extracted (500 mL×3) with a mixed solvent of THF-methanol (10/1). Butanol was added to the extract solution and the mixture was concentrated under reduced pressure. Diisopropyl ether (1L) was added to the residue, and the precipitate was collected by filtration and dried to give the title compound (37.80 g, quantitative determination) as a white solid.

$^1$H-NMR (DMSO-d$_6$) δ 10.90–10.75 (m, 1H), 8.40–8.25 (m, 1H), 8.12–8.00 (m, 1H), 7.90–7.75 (m, 4H), 7.40–7.25 (m, 2H), 7.05–6.90 (m, 2H), 6.70–6.55 (m, 1H), 4.85–4.70 (m, 1H), 4.60–4.30 (m, 1H), 4.10–3.10 (m, 5H), 3.10–2.20 (m, 5H), 2.00–1.80 (m, 1H), 1.70–1.15 (m, 8H), 0.95–0.70 (m, 1H), 0.83 (d, J=6.3 Hz, 3H), 0.74 (d, J=6.3 Hz, 3H).

(8) 5-methyl-3(R)-[2-phenyl-1(S)-(sulfomethylcarbamoyl)ethylcarbamoyl]-2(R or S)-phthalimidomethylhexanohydroxamic acid sodium salt The title compound (37.80 g, about 9.99 mmol) of Example 15 (7) was suspended in a mixed solvent of water (200 mL)-methanol (400 mL)-THF (200 mL) and 1N hydrochloric acid (200 mL) was added at room temperature. The mixture was stirred for 8 hr at the same temperature. Methanol and THF were distilled away under reduced pressure from the reaction solution. The precipitate was collected by filtration and washed with isopropyl alcohol and diisopropyl ether. The obtained precipitate was suspended in water (250 mL), and neutralized with sodium hydrogencarbonate (0.84 g, 9.99 mmol). The obtained aqueous solution was purified by synthetic adsorbent column (DIAION HP-20: water, 50% aqueous methanol solution), and the fractions eluted with a 50% aqueous methanol solution were collected and concentrated under reduced pressure until the precipitate appeared. The residue was recrystallized from water-isopropyl alcohol to give the title compound (1.37 g, 22%) as white crystals.

$^1$H-NMR (DMSO-$d_6$) δ 10.27 (br s, 1H), 8.56 (br s, 1H), 8.29 (d, J=9.0 Hz, 1H), 8.10–7.95 (m, 1H), 7.95–7.80 (m, 4H), 7.40–7.30 (m, 2H), 7.10–6.90 (m, 2H), 6.70–6.55 (m, 1H), 4.85–4.70 (m, 1H), 4.01 (dd, J=13.0, 6.6 Hz, 1H), 3.81 (dd, J=13.0, 5.3 Hz, 1H), 3.50–3.20 (m, 1H), 3.12 (dd, J=13.7, 3.2 Hz, 1H), 2.80–2.60 (m, 1H), 2.50–2.32 (m, 2H), 1.97–1.80 (m, 1H), 1.55–1.25 (m, 2H), 0.90–0.70 (m, 1H), 0.84 (d, J=6.6 Hz, 3H), 0.75 (d, J=6.6 Hz, 3H).

EXAMPLE 16

5-methyl-3(R)-[2-phenyl-1(R)-(sulfomethylcarbamoyl)ethylcarbamoyl]-2(R or S)-phthalimidomethylhexanohydroxamic acid sodium salt [One Kind of Diastereomer of Compound of Example 15]

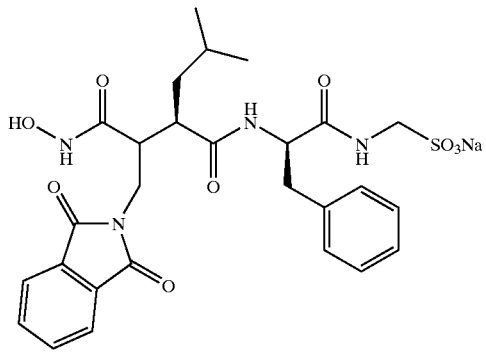

(1) 2-tetrahydropyranyl 5-methyl-3(R)-[2-phenyl-1(R)-(sulfomethylcarbamoyl)ethylcarbamoyl]-2(R or S)-(phthalimidomethyl)hexanohydroxamate sodium salt To a solution of the title compound (1.00 g, 1.73 mmol) of Example 15 (6) in DMF (20 mL) were added successively aminomethanesulfonic acid (0.23 g, 2.07 mmol), N-methylmorpholine (0.42 mL, 3.80 mmol), HOBt·H$_2$O (0.26 g, 1.73 mmol) and WSCI·HCl (0.40 g, 2.07 mmol) under ice-cooling, and the mixture was stirred for 16 hr while gradually raising the temperature to room temperature. A solution of sodium dihydrogenphosphate dihydrate (1.35 g, 8.63 mmol) in water (80 mL) was added to the reaction solution, and saturated with sodium chloride. The mixture was extracted (100 mL×3) with THF, and butanol was added to the extract solution. The mixture was concentrated under reduced pressure and diethyl ether was added to the residue. The precipitate was collected by filtration and dried to give the title compound (1.27 g, quantitative determination, 28% de) as a white powder.

(2) 5-methyl-3(R)-[2-phenyl-1(R)-(sulfomethylcarbamoyl)ethylcarbamoyl]-2(R or S)-phthalimidomethylhexanohydroxamic acid sodium salt The title compound (1.27 g, about 1.73 mmol, 28% de) of Example 16 (1) was suspended in a solution of water (25 mL)-methanol (60 mL)-THF (20 mL), and 1N hydrochloric acid (10 mL) was added at room temperature. The mixture was stirred for 7 hr at the same temperature and methanol and THF were distilled away under reduced pressure from the reaction solution. Water (20 mL) and sodium hydrogencarbonate (1.00 g, 11.90 mmol) were added for neutralization. The obtained solution was purified by reverse phase column chromatography (Fuji Silysia Chemical Chromatorex ODS DM-1020T: 50 g, water/methanol=100/0, 50/1, 20/1, 10/1, 5/1). The eluates from the latter half were collected and methanol was distilled away under reduced pressure, followed by freeze-drying. The obtained freeze-dry product was precipitated from methanol-diethyl ether to give the title compound (0.24 g, 21%) as a white solid.

$^1$H-NMR (DMSO-$d_6$) δ 10.39 (br s, 1H), 9.00–8.20 (br, 1H), 8.41 (d, J=9.0 Hz, 1H), 8.18 (dd, J=6.7, 5.2 Hz, 1H), 7.90–7.75 (m, 4H), 7.31 (d, J=6.9 Hz, 2H), 7.24 (t, J=7.2 Hz, 2H), 7.16 (t, J=7.1 Hz, 1H), 4.75–4.60 (m, 1H), 4.08–3.98 (m, 1H), 3.99 (dd, J=12.9, 6.7 Hz, 1H), 3.77 (dd, J=12.9, 5.2 Hz, 1H), 3.50–3.30 (m, 1H), 3.13 (dd, J=13.9, 3.0 Hz, 1H), 2.70–2.58 (m, 1H), 2.69 (dd, J=13.9, 11.8 Hz, 1H), 2.58–2.45 (m, 1H), 1.29 (t, J=12.0 Hz, 1H), 0.81–0.65 (m, 1H), 0.65–0.50 (m, 1H), 0.54 (d, J=5.1 Hz, 6H).

EXAMPLE 17

5-methyl-3(R)-[2-phenyl-1(S)-(2-sulfoethylcarbamoyl)ethylcarbamoyl]-2(R or S)-phthalimidomethylhexanohydroxamic acid sodium salt

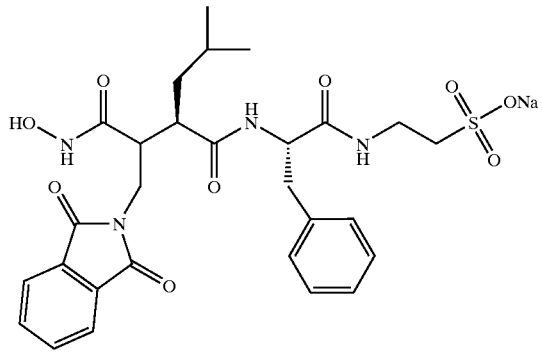

Using the title compound of Example 15 (6) and taurine, and in the same manner as in the method described in Example 15 (7)–(8), synthesis was performed.

$^1$H-NMR (DMSO-$d_6$) δ 10.31 (br s, 1H), 8.59 (s, 1H), 8.38 (d, J=8.7 Hz, 1H), 7.85–7.80 (br s, 5H), 7.29–7.25 (m, 2H), 7.08–7.00 (m, 2H), 6.77–6.70 (m, 1H), 4.65–4.50 (m, 1H), 3.85–3.74 (m, 1H), 3.52–3.25 (m, 3H), 3.07–2.93 (m, 1H), 2.85–2.70 (m, 1H), 2.55–2.40 (m, 3H), 2.19–2.10 (m, 1H), 1.55–1.29 (m, 2H), 0.90–0.70 (m, 1H), 0.82 (d, J=6.3 Hz, 3H), 0.76 (d, J=6.3 Hz, 3H).

EXAMPLE 18

5-methyl-3(R)-[2-phenyl-1(R)-(2-sulfoethylcarbamoyl)ethylcarbamoyl]-2(R or S)-phthalimidomethylhexanohydroxamic acid sodium salt [One Kind of Diastereomer of Compound of Example 17]

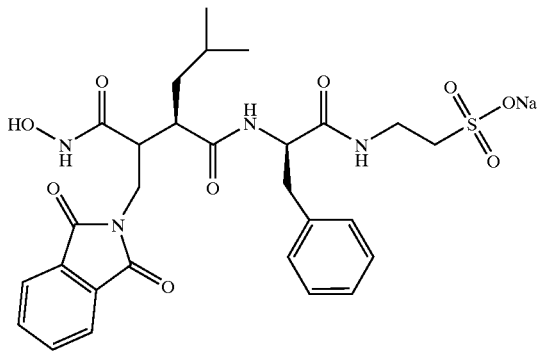

Using the title compound of Example 15 (6) and taurine, and in the same manner as in the method described in Example 16 (1)–(2), synthesis was performed.

$^1$H-NMR (DMSO-$d_6$) δ 10.41 (br s, 1H), 8.70 (s, 1H), 8.43 (d, J=8.4 Hz, 1H), 8.08–8.03 (1H, m), 7.83–7.80 (br s, 4H), 7.27–7.14 (m, 5H), 4.51–4.44 (m, 1H), 4.00–3.90 (m, 1H), 3.48–3.27 (m, 3H), 3.22–3.04 (m, 1H), 2.85–2.55 (m, 5H), 1.65–1.30 (m, 1H), 0.85–0.54 (m, 8H).

EXAMPLE 19

5-methyl-3(R)-[2-phenyl-1(S)-(3-sulfopropylcarbamoyl)ethylcarbamoyl]-2(R or S)-phthalimidomethylhexanohydroxamic acid sodium salt

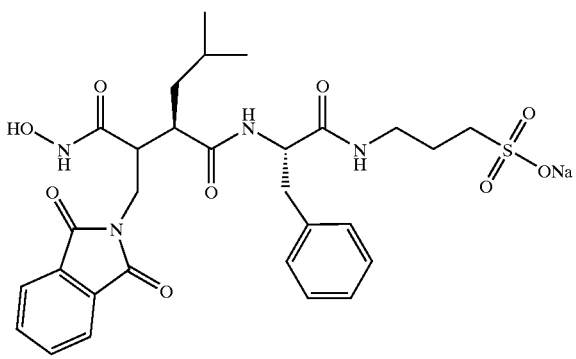

Using the title compound of Example 15 (6) and 3-aminopropanesulfonic acid, and in the same manner as in the method described in Example 15 (7)–(8), synthesis was performed.

$^1$H-NMR (DMSO-$d_6$) δ 10.30 (s, 1H), 8.59 (s, 1H), 8.33 (d, J=8.7 Hz, 1H), 7.85–7.80 (br s, 5H), 7.31–7.27 (m, 2H), 7.07–7.00 (m, 2H), 6.73–6.65 (s, 1H), 4.68–4.55 (m, 1H), 3.85–3.73 (m, 1H), 3.25–2.95 (m, 3H), 2.84–2.70 (m, 1H), 2.58–2.33 (m, 4H), 2.16–2.04 (m, 1H), 1.80–1.64 (m, 2H), 1.55–1.35 (m, 2H), 0.90–0.70 (m, 1H), 0.83 (d, J=6.6 Hz, 3H), 0.76 (d, J=6.6 Hz, 3H).

EXAMPLE 20

5-methyl-3(R)-[2-phenyl-1(R)-(3-sulfopropylcarbamoyl)ethylcarbamoyl]-2(R or S)-phthalimidomethylhexanohydroxamic acid sodium salt [One Kind of Diastereomer of Compound of Example 19]

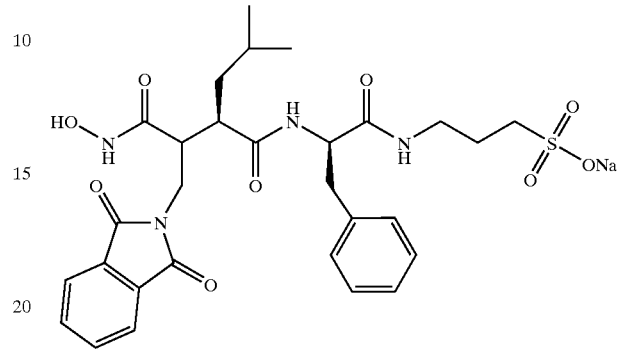

Using the title compound of Example 15 (6) and 3-aminopropanesulfonic acid, and in the same manner as in the method described in Example 16 (1)–(2), synthesis was performed.

$^1$H-NMR (DMSO-$d_6$) δ 10.40 (s, 1H), 8.62 (s, 1H), 8.40 (d, J=8.7 Hz, 1H), 7.86–7.73 (br s, 4H), 7.32–7.05 (m, 5H), 4.60–4.48 (m, 1H), 4.02–3.89 (m, 1H), 3.82–3.69 (m, 1H), 3.68–3.30 (m, 2H), 3.25–3.00 (m, 3H), 2.82–2.70 (m, 2H), 2.69–2.20 (m, 2H), 1.82–1.64 (m, 2H), 1.40–1.20 (m, 1H), 0.85–0.41 (m, 8H).

EXAMPLE 21

5-methyl-3(R)-[2-phenyl-1(S)-(4-sulfobutylcarbamoyl)ethylcarbamoyl]-2(R or S)-phthalimidomethylhexanohydroxamic acid sodium salt

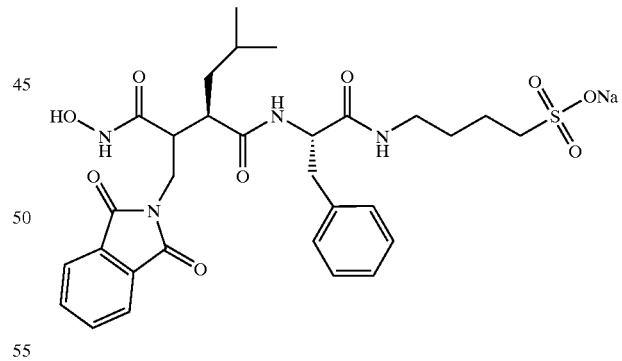

Using the title compound of Example 15 (6) and 4-aminobutanesulfonic acid, and in the same manner as in the method described in Example 15 (7)–(8), synthesis was performed.

$^1$H-NMR (DMSO-$d_6$) δ 10.31 (s, 1H), 8.59 (s, 1H), 8.35 (d, J=8.7 Hz, 1H), 7.84–7.80 (br s, 5H), 7.31–7.24 (m, 2H), 7.07–7.01 (m, 2H), 6.73–6.67 (s, 1H), 4.68–4.58 (m, 1H), 3.84–3.70 (s, 1H), 3.44–3.22 (m, 1H), 3.15–2.84 (m, 3H), 2.89–2.71 (m, 1H), 2.51–2.32 (m, 3H), 2.17–2.03 (m, 1H), 1.70–1.20 (m, 6H), 0.90–0.70 (m, 1H), 0.82 (d, J=6.6 Hz, 3H), 0.76 (d, J=6.6 Hz, 3H).

EXAMPLE 22

5-methyl-3(R)-[2-phenyl-1(S)-(5-sulfopentylcarbamoyl)ethylcarbamoyl]-2(R or S)-phthalimidomethylhexanohydroxamic acid sodium salt

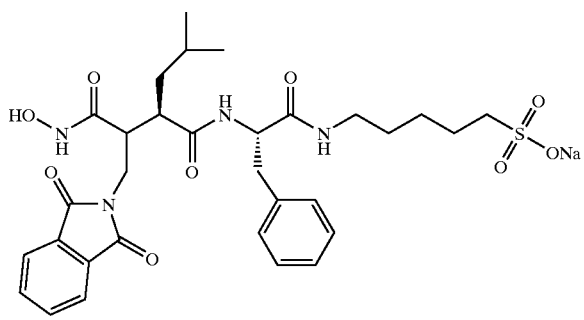

(1) 5-bromopentylsulfonic acid sodium salt

To a solution of 1,5-dibromopentane (23.2 g, 101 mmol), ethanol (40 mL) and water (40 mL) was dropwise added a solution of sodium sulfite (4.24 g, 33.6 mmol) in water (15 mL) under heating under reflux over 2 hr. After heating under reflux for 2 hr, the solvent was distilled away under reduced pressure and n-hexane/ethanol was added. The precipitated crystals were washed with n-hexane and dried in vacuo to give the title compound (3.81 g, 45%).

$^1$H-NMR (DMSO-$d_6$) δ 3.51 (t, J=6.6 Hz, 2H), 2.46 (t, J=7.5 Hz, 2H), 1.90–1.01 (m, 6H).

(2) 5-aminopentylsulfonic acid

Aqueous ammonia (50 mL) was added to the title compound (3.80 g, 15.0 mmol) of Example 22 (1). The mixture was stirred at room temperature for 4 days and dissolved in ethanol. The insoluble material was filtered off and the filtrate was concentrated under reduced pressure and dried in vacuo to give the title compound (3.53 g, quantitative determination).

$^1$H-NMR (DMSO-$d_6$) δ 7.90–7.55 (br, 2H), 2.76 (t, J=7.2 Hz, 2H), 2.39 (t, J=7.8 Hz, 2H), 1.71–1.05 (m, 6H).

(3) 5-methyl-3(R)-[2-phenyl-1(S)-(5-sulfopentylcarbamoyl)ethylcarbamoyl]-2(R or S)-phthalimidomethylhexanohydroxamic acid sodium salt Using the title compound of Example 15 (6) and the title compound of Example 22 (2), and in the same manner as in the method described in Example 15 (7)–(8), synthesis was performed.

$^1$H-NMR (DMSO-$d_6$) δ 10.32 (s, 1H), 8.60 (s, 1H), 8.37 (d, J=8.4 Hz, 1H), 7.85–7.81 (br s, 5H), 7.77–7.72 (m, 1H), 7.30–7.26 (m, 2H), 7.08–7.02 (m, 2H), 6.76–6.70 (s, 1H), 4.70–4.58 (m, 1H), 3.50–3.30 (m, 1H), 3.21–2.99 (m, 3H), 2.88–2.69 (m, 1H), 2.58–2.31 (m, 3H), 2.21–2.08 (m, 1H), 1.67–1.17 (m, 8H), 0.90–0.70 (m, 1H), 0.82 (d, J=6.3 Hz, 3H), 0.76 (d, J=6.6 Hz, 3H).

EXAMPLE 23

5-methyl-3(R)-[2-phenyl-1(S)-(4-sulfophenylcarbamoyl)ethylcarbamoyl]-2(R or S)-phthalimidomethylhexanohydroxamic acid sodium salt

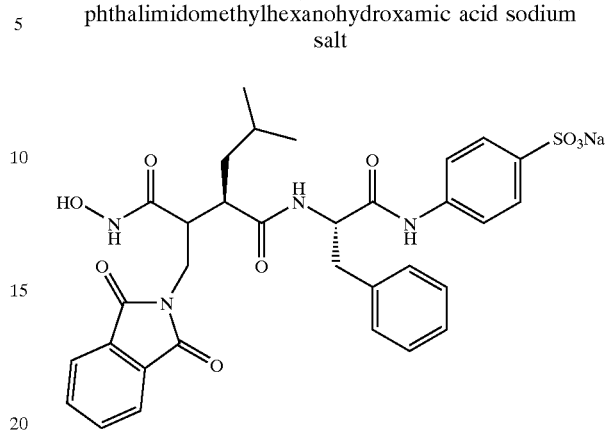

Using the title compound of Example 15 (6) and sulfanilic acid, and in the same manner as in the method described in Example 15 (7)–(8), synthesis was performed.

$^1$H-NMR (DMSO-$d_6$) δ 10.32 (br s, 1H), 10.15 (br s, 1H), 8.90–8.30 (br, 1H), 8.53 (d, J=8.4 Hz, 1H), 8.00–7.80 (m, 4H), 7.70–7.50 (m, 4H), 7.36 (d, J=7.5 Hz, 2H), 7.07 (t, J=7.5 Hz, 2H), 6.74 (t, J=7.4 Hz, 1H), 4.95–4.80 (m, 1H), 3.50–3.25 (m, 1H), 3.10 (dd, J=13.6, 4.5 Hz, 1H), 2.86 (dd, J=13.6, 11.1 Hz, 1H), 2.62–2.37 (m, 2H), 2.19 (dd, J=13.8, 3.8 Hz, 1H), 1.60–1.20 (m, 2H), 0.95–0.80 (m, 1H), 0.84 (d, J=6.3 Hz, 3H), 0.74 (d, J=6.3 Hz, 3H).

EXAMPLE 24

5-methyl-3(R)-[2-phenyl-1(R)-(4-sulfophenylcarbamoyl)ethylcarbamoyl]-2(R or S)-phthalimidomethylhexanohydroxamic acid sodium salt [One Kind of Diastereomer of Compound of Example 23]

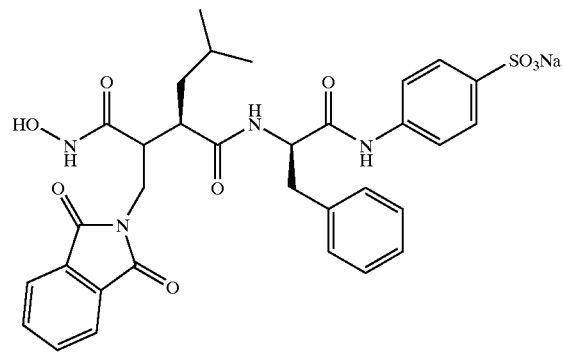

Using the title compound of Example 15 (6) and sulfanilic acid, and in the same manner as in the method described in Example 16 (1)–(2), synthesis was performed.

$^1$H-NMR (DMSO-$d_6$) δ 10.45 (br s, 1H), 10.16 (br s, 1H), 8.68 (br s, 1H), 8.61 (d, J=8.4 Hz, 1H), 7.90–7.70 (m, 4H), 7.60 (d, J=8.7 Hz, 2H), 7.49 (d, J=8.7 Hz, 2H), 7.34 (d, J=7.2 Hz, 2H), 7.27 (t, J=7.4 Hz, 2H), 7.19 (t, J=7.2 Hz, 1H), 4.85–4.65 (m, 1H), 4.04 (dd, J=13.3, 10.8 Hz, 1H), 3.42 (dd, J=13.3, 3.2 Hz, 1H), 3.18 (dd, J=13.5, 3.3 Hz, 1H), 2.83 (dd, J=13.5, 11.3 Hz, 1H), 2.80–2.40 (m, 2H), 1.50–1.30 (m, 1H), 0.95–0.65 (m, 2H), 0.61 (d, J=6.0 Hz, 3H), 0.59 (d, J=6.0 Hz, 3H).

EXAMPLE 25

5-methyl-2(R or S)-(2-naphthylmethyl)-3(R)-[2-phenyl-1(S)-(sulfomethylcarbamoyl)ethylcarbamoyl] hexanohydroxamic acid sodium salt

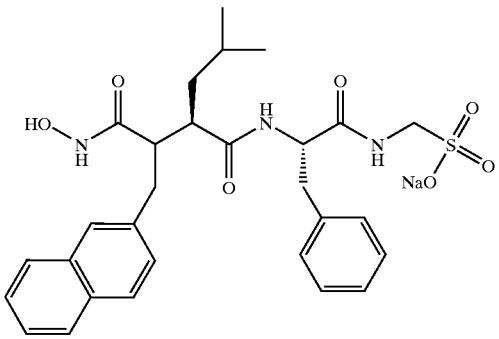

(1) 2-tetrahydropyranyl 5-methyl-3(R)-[1(S)-carboxy-2-phenylethylcarbamoyl]-2(R or S)-(2-naphthylmethyl)hexanohydroxamate sodium salt Using the title compound of Example 13 (1) and the title compound of Example 15 (2), and in the same manner as in the method described in Example 15 (3)–(6), synthesis was performed.

(2) 5-methyl-2(R or S)-(2-naphthylmethyl)-3(R)-[2-phenyl-1(S)-(sulfomethylcarbamoyl)ethylcarbamoyl] hexanohydroxamic acid sodium salt Using the title compound of Example 25 (1) and aminomethanesulfonic acid, and in the same manner as in the method described in Example 15 (7)–(8), synthesis was performed.

$^1$H-NMR (DMSO-$d_6$) δ 13.00–9.70 (br, 1H), 8.32 (d, J=8.4 Hz, 1H), 8.20–8.07 (br, 1H), 7.85–7.69 (m, 3H), 7.50–7.29 (m, 4H), 7.28–7.19 (m, 1H), 7.13–7.00 (s, 2H), 6.99–6.84 (m, 1H), 6.82–6.60 (m, 1H), 4.99–4.68 (m, 1H), 4.10–3.94 (m, 1H), 3.93–3.75 (m, 1H), 3.07–2.98 (m, 1H), 2.75–2.69 (m, 1H), 2.52–2.30 (m, 3H), 2.29–2.14 (m, 1H), 1.85–1.66 (m, 1H), 1.50–1.24 (m, 2H), 0.90–0.70 (m, 1H), 0.85 (d, J=6.3 Hz, 3H), 0.75 (d, J=6.3 Hz, 3H).

EXAMPLE 26

5-methyl-2(R or S)-(2-naphthylmethyl)-3(R)-[2-phenyl-1(S)-(2-sulfoethylcarbamoyl) ethylcarbamoyl]hexanohydroxamic acid sodium salt

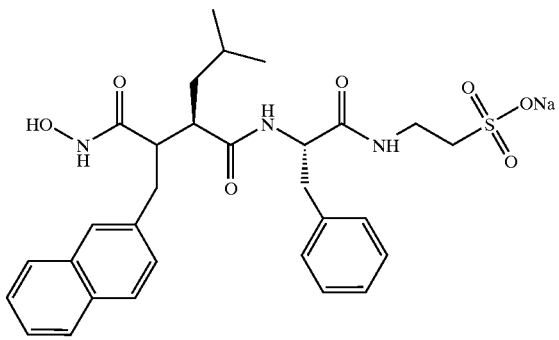

Using the title compound of Example 25 (1) and taurine, and in the same manner as in the method described in Example 15 (7)–(8), synthesis was performed.

$^1$H-NMR (DMSO-$d_6$) δ 10.15 (br s, 1H), 8.69–8.43 (br s, 1H), 8.38 (d, J=8.7 Hz, 1H), 7.94–7.69 (m, 4H), 7.50–7.37 (m, 2H), 7.36–7.24 (m, 3H), 7.18–7.03 (m, 2H), 7.02–6.98 (m, 1H), 6.89–6.78 (m, 1H), 4.70–4.56 (m, 1H), 3.50–2.78 (m, 3H), 3.18–2.92 (m, 1H), 2.91–2.85 (m, 1H), 2.58–2.41 (m, 3H), 2.39–2.10 (m, 1H), 2.00–1.87 (m, 1H), 1.50–1.28 (m, 2H), 0.90–0.70 (m, 1H), 0.85 (d, J=6.3 Hz, 3H), 0.77 (d, J=6.3 Hz, 3H).

EXPERIMENTAL EXAMPLE 1

Inhibitory Effect of Pharmaceutical Agent on LPS in E. coli Culture Supernatant One platinum loop of E. coli NIHJ JC-2 strain was inoculated into a test tube containing heart infusion broth (HIB, 5 mL) and cultured for about 24 hr. The bacterial culture broth was washed three times by centrifugation (3000 rpm, 15 min, 20° C., TOMY Seiko, RL-131) using 10 mL of fresh HIB medium for one cycle of washing. The washed bacteria were prepared to an about $10^7$ colony forming unit (CFU)/mL with a fresh HIB medium, and 0.2 mL of the prepared bacterial suspension was inoculated into an Erlenmeyer flask containing a fresh HIB medium (18.8 mL) (i.e., to final bacterial concentration of about $10^5$ CFU/mL). A solution (1 mL) of each compound prepared to a concentration of 2 mM (final concentration of compound 100 μM) was added to the culture broth containing the bacteria. Using a shaker (RGR-1 type, manufactured by IWASHIYA, Ltd.), shake culture was conducted at 37° C., and 2 mL of culture broth after 24 hr was sampled. The sampled culture broth was filtered (DISMIC, 0.45 μm, Advantech Toyo) and diluted $10^5$-fold with sterile distilled water. The resulting suspension (200 μL) was added to a limulus reagent (LAL ES, Wako Pure Chemical Industries) and LPS concentration was measured using Toxinometer MT-285 (Wako Pure Chemical Industries) preheated to 37° C.

The LPS inhibitory ratio of the compound was calculated as a ratio of the LPS concentration of the compound addition group relative to the LPS concentration of the compound non-addition group. As a result, the inhibitory ratio of the compound of Example 1 was 46.5–65.8%. The inhibitory ratio of each compound is shown in the following in Table 1 as a relative ratio to the inhibitory ratio of the compound of Example 1 as 1.0.

TABLE 1 inhibitory effect of compound on LPS in E. coli culture supernatant

|  | relative ratio |
| --- | --- |
| compound of Example 1 | 1.0 |
| compound of Example 3 | 0.70 |
| compound of Example 4 | 0.69 |
| compound of Example 5 | 0.80 |
| compound of Example 6 | 0.69 |
| compound of Example 7 | 0.79 |
| compound of Example 8 | 0.60 |
| compound of Example 9 | 0.51 |
| compound of Example 10 | 0.87 |
| compound of Example 11 | 0.74 |
| compound of Example 12 | 0.85 |
| compound of Example 13 | 0.87 |
| compound of Example 15 | 1.05 |
| compound of Example 17 | 0.78 |
| compound of Example 19 | 0.67 |
| compound of Example 21 | 0.79 |
| compound of Example 22 | 0.68 |
| compound of Example 25 | 0.33 |
| compound of Example 26 | 0.54 |

EXPERIMENTAL EXAMPLE 2

Inhibitory Effect of Pharmaceutical Agent on LPS that Increases in Rat Peritonitis Model Rat peritonitis (CLP; cecal ligation and puncture) model was prepared according to the method of Wichterman et al.

(J. Surg. Res. 29, 189–201 <1980>). That is, a rat fasted overnight was anesthetized with ether, and a midline laparotomy was performed and the cecum was exposed. The cecum was ligated with a 3-0 silk thread at its base and perforated two times with an 18 G injection needle. The cecum was gently squeezed to extrude feces, which were spread around the abdomen, and the sectioned part was sutured. The animal was fixed in a Borrmann cage, and physiological saline or drug solution (2 mg/mL) was continuously given from the tail vein at an administration rate of 2.5 mg/kg/hr with an infusion pump (22 M, Harvard, 5 mL/kg/hr as a dose).

After 6 hr of the CLP treatment, the animal was sacrificed with carbonic acid gas. The abdominal cavity was washed by injecting phosphate buffered saline (PBS; 37° C., 10 mL) and the abdominal cavity washing containing ascites (PLF; peritoneal lavage fluid) was recovered. The recovery weight of the obtained PLF was measured, and PLF was centrifuged (1500 rpm for 5 min, 4° C.) to recover supernatant. The blood taken from the heart was centrifuged (3000 rpm for 10 min, 4° C.) using a serum separation tube, and the serum was recovered. The concentration of LPS in the abdominal cavity and serum was measured using Toxinometer MT-285 (Waco Pure Chemical Industries) preheated to 37° C., after diluting the supernatant and serum of the recovered PLF $10^5$-fold and $10^2$-fold, respectively, with sterile distilled water, and adding 200 μL thereof to a limulus reagent (LAL ES, Waco Pure Chemical Industries). The amount of LPS per abdominal cavity was calculated from amount of recovered abdominal cavity washing (PLF)×LPS concentration of PLF.

The LPS inhibitory ratio of the compound was calculated as the ratio of LPS concentration of the compound administration group to LPS concentration of the physiological saline administration group. The LPS inhibitory ratio of each compound in blood and abdominal cavity was as shown in Table 2.

TABLE 2 inhibitory effect of compound against increase in LPS in rat peritonitis model

| | LPS inhibitory ratio (%) | |
|---|---|---|
| | in blood | in abdominal cavity |
| compound of Example 1 | 79.9 | 88.3 |
| compound of Example 10 | 81.4 | 88.1 |
| compound of Example 11 | 36.2 | 5.5 |
| compound of Example 13 | 74.2 | 44.7 |
| compound of Example 15 | 68.2 | 70.3 |
| compound of Example 17 | 59.1 | 14.4 |
| compound of Example 19 | 67.8 | 89.6 |
| compound of Example 21 | 55.9 | 57.1 |
| compound of Example 22 | 21.6 | 80.7 |

From the above-mentioned experimental results, it is clear that the sulfonic acid derivative of hydroxamic acid of the present invention has an LPS inhibitory action.

PREPARATION EXAMPLE 1

Tablets containing the following ingredients were prepared according to a conventional method.

| Ingredients | per tablet |
|---|---|
| Compound of Example 1 | 10 mg |
| Lactose | 125 mg |
| Cornstarch | 75 mg |
| Talc | 4 mg |

-continued

| Ingredients | per tablet |
|---|---|
| Magnesium stearate | 1 mg |
| Total amount | 215 mg |

PREPARATION EXAMPLE 2

Capsules containing the following ingredients were prepared according to a conventional method.

| Ingredients | per capsule |
|---|---|
| Compound of Example 1 | 10 mg |
| Lactose | 165 mg |
| Cornstarch | 20 mg |
| Talc | 5 mg |
| weight of one capsule | 200 mg |

PREPARATION EXAMPLE 3

Ointment containing the following ingredients was prepared according to a conventional method.

| Ingredients | dose |
|---|---|
| Compound of Example 1 | 0.2 g |
| white petrolatum | 97.8 g |
| liquid paraffin | 2 g |
| total weight | 100 g |

PREPARATION EXAMPLE 4

Injection containing the following ingredients was prepared according to a conventional method.

| Ingredients | dose |
|---|---|
| Compound of Example 1 | 0.2 g |
| sodium chloride | 0.9 g |
| distilled water for injection | suitable amount |
| total weight | 100 g |

PREPARATION EXAMPLE 5

Eye drop containing the following ingredients was prepared according to a conventional method.

| Ingredients | |
|---|---|
| Compound of Example 1 | 0.1 g |
| sodium chloride | 0.3 g |
| sterile purified water | suitable amount |
| total weight | 100 g |

INDUSTRIAL APPLICABILITY

The sulfonic acid derivative of hydroxamic acid and a pharmacologically acceptable salt thereof of the present invention have an LPS inhibitory action, and are useful for the prophylaxis or treatment of diseases such as sepsis, MOF, chronic articular rheumatism, Crohn's disease, cachexia, myasthenia gravis, systemic lupus erythematodes, asthma, type I diabetes, psoriasis, other autoimmune diseases, inflammatory diseases and the like.

This application is based on patent application Nos. 219245/2000 and 219034/2000 filed in Japan, the contents of which are hereby incorporated by reference. The references cited herein, including patents and patent applications, are hereby incorporated in their entireties by reference, to the extent that they have been disclosed herein.

What is claimed is:

1. A sulfonic acid compound of hydroxamic acid of the formula (I):

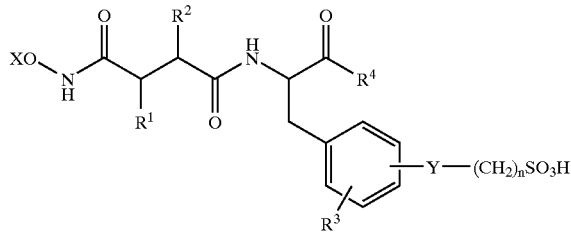

I wherein
X is hydrogen or a hydroxyl group-protecting group;
$R^1$ is phthalimidomethyl;
$R^2$ is hydrogen, alkyl, arylalkyl, heteroarylalkyl, cycloalkyl, cycloalkylalkyl or aryl;
Y is O, $NR^7$ wherein $R^7$ is as defined for $R^2$ or S;
n is an integer of any of 1 to 6;
$R^3$ is hydrogen, halogen, hydroxyl group, trifluoromethyl, cyano, nitro, amino, alkyl, alkoxy, acyloxy, carbamoyl, lower alkylamino or dilower alkylamino group;
$R_4$ is $OR^8$ wherein $R^8$ is hydrogen, lower alkyl, aryl, heteroaryl, arylalkyl or heteroarylalkyl or $NR^{10}R^{11}$ wherein $R^{10}$ and $R^{11}$ are the same or different and each is hydrogen, lower alkyl, arylalkyl, heteroaryl, heteroarylalkyl or aryl, or $R^{10}$ and $R^{11}$ optionally form an optionally substituted hetero ring together with the adjacent nitrogen atom; and
said arylalkyl, heteroarylalkyl, heteroarylalkylthioalkyl, heteroarylthioalkyl, arylthioalkyl, arylalkylthioalkyl, phthalimidomethyl, aryl and heteroaryl optionally have substituents, or a pharmacologically acceptable salt thereof.

2. The sulfonic acid compound of hydroxamic acid of claim 1, wherein $R^3$ is hydrogen, or a pharmacologically acceptable salt thereof.

3. The sulfonic acid compound of hydroxamic acid of claim 1, wherein $R^4$ is $NHCH_3$ or $NHC_6H_5$, or a pharmacologically acceptable salt thereof.

4. The sulfonic acid compound of hydroxamic acid of claim 1, wherein $R^2$ is isobutyl, or a pharmacologically acceptable salt thereof.

5. A sulfonic acid compound of hydroxamic acid selected from the group consisting of:

5-methyl-3(R)-[1 (S)-methylcarbamoyl-2-(4-sulfomethoxyphenyl1)ethylcarbamoyl]-2(R or S)-phthalimidomethylhexanohydroxamic acid, 5-methyl-3 (R)-{1(S)-methylcarbamoyl-2-[4-(2-sulfoethoxy)phenyl]ethylcarbamoyl}-2(R or S)-phthalimidomethylhexanohydroxamic acid, 5-methyl-3(R)-{1(S)-methylcarbamoyl-2-[4-(3-sulfopropoxy)phenyl]ethylcarbamoyl}-2(R or S)phthalimidomethylhexanohydroxamic acid, 5-methyl-3(R)-{1(S)-methylcarbamoyl-2-[4-(4-sulfobutoxy)phenyl]ethylcarbamoyl}-2(R or S)-phthalimidomethylhexanohydroxamic acid, 5-methyl-3(R)-{1(S)-methylcarbamoyl-2-[4-(5-sulfopentoxy)phenyl]ethylcarbamoyl}-2(R or S)-phthalimidomethylhexanohydroxamic acid, and 5-methyl-3(R)-{1(S)-phenylcarbamoyl-2-[4-(3-sulfopropoxy)phenyl]ethylcarbamoyl}-2(R or S)-phthalimidomethylhexanohydroxamic acid, or a pharmacologically acceptable salt thereof.

6. A pharmaceutical composition comprising the sulfonic acid compound of hydroxamic acid of claim 1 or a pharmacologically acceptable salt thereof, and a pharmacologically acceptable carrier.

7. A method of preventing sepsis, which comprises administering an effective amount of a sulfonic acid compound of hydroxamic acid or a pharmacologically acceptable salt thereof to a mammal in need thereof, wherein the sulfonic acid compound has the formula (I):

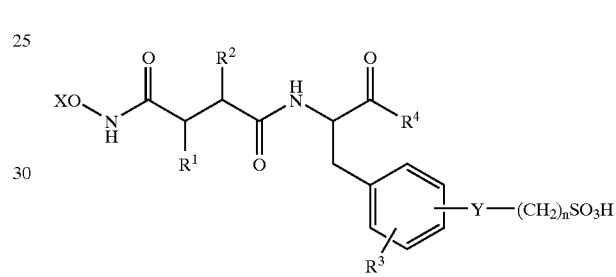

I wherein

X is hydrogen or a hydroxyl group-protecting group;
$R^1$ is phthalimidomethyl;
$R^2$ is hydrogen, alkyl, arylalkyl, heteroarylalkyl, cycloalkyl, cycloalkylalkyl or aryl;
Y is O, $NR^7$ wherein $R^7$ is as defined for $R^2$ or S;
n is an integer of any of 1 to 6;
$R^3$ is hydrogen, halogen, hydroxyl group, trifluoromethyl, cyano, nitro, amino, alkyl, alkoxy, acyloxy, carbamoyl, lower alkylamino or dilower alkylamino group;
$R^4$ is $OR^8$ wherein $R^8$ is hydrogen, lower alkyl, aryl, heteroaryl, arylalkyl or heteroarylalkyl or $NR^{10}R^{11}$ wherein $R^{10}$ and $R^{11}$ are the same or different and each is hydrogen, lower alkyl, arylalkyl, heteroaryl, heteroarylalkyl or aryl, or $R^{10}$ and $R^{11}$ optionally form an optionally substituted hetero ring together with the adjacent nitrogen atom; and said arylalkyl, heteroarylalkyl, heteroarylalkylthioalkyl, heteroarylthioalkyl, arylthioalkyl, arylalkylthioalkyl, phthalimidomethyl, aryl and heteroaryl optionally have substituents, or a pharmacologically acceptable salt thereof.

8. A method of treating sepsis, MOF, chronic articular rheumatism, Crohn's disease, cachexia, or asthma, which comprises administering an effective amount of a sulfonic acid compound of hydroxamic acid or a pharmacologically acceptable salt thereof to a mammal in need thereof, wherein the sulfonic acid compound has the formula (I):

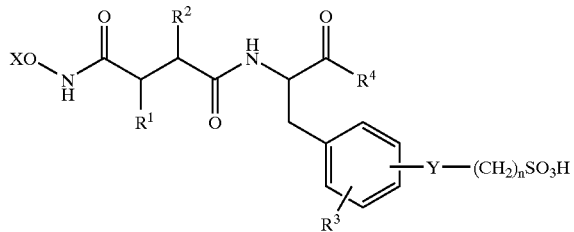

wherein
X is hydrogen or a hydroxyl group-protecting group;
$R^1$ is phthalimidomethyl;
$R^2$ is hydrogen, alkyl, arylalkyl, heteroarylalkyl, cycloalkyl, cycloalkylalkyl or aryl;
Y is O, $NR^7$ wherein $R^7$ is as defined for $R^2$ or S;

n is an integer of any of 1 to 6;
$R^3$ is hydrogen, halogen, hydroxyl group, trifluoromethyl, cyano, nitro, amino, alkyl, alkoxy, acyloxy, carbamoyl, lower alkenylamino or dilower alkylamino group;
$R^4$ is $OR^8$ wherein $R^8$ is hydrogen, lower alkyl, aryl, heteroaryl, arylalkyl or heteroarylalkyl or $NR^{10}R^{11}$ wherein $R^{10}$ and $R^{11}$ are the same or different and each is hydrogen, lower alkyl, arylalkyl, heteroaryl, heteroarylalkyl or aryl, or $R^{10}$ and $R^{11}$ optionally form an optionally substituted hetero ring together with the adjacent nitrogen atom; and
said arylalkyl, heteroarylalkyl, heteroarylalkylthioalkyl, heteroarylthioalkyl, arylthioalkyl, arylalkylthioalkyl, phthalimidomethyl, aryl and heteroaryl optionally have substituents, or a pharmacologically acceptable salt thereof.

* * * * *